(12) United States Patent
Dong et al.

(10) Patent No.: US 9,814,715 B2
(45) Date of Patent: *Nov. 14, 2017

(54) LIVER X RECEPTOR MODULATORS

(71) Applicant: Vitae Pharmaceuticals, Inc., Fort Washington, PA (US)

(72) Inventors: Chengguo Dong, Staten Island, NY (US); Yi Fan, Doylestown, PA (US); Katerina Leftheris, San Diego, CA (US); Stephen D. Lotesta, Burlington, NJ (US); Suresh B. Singh, Kendall Park, NJ (US); Colin M. Tice, Maple Glen, PA (US); Wei Zhao, North Potomac, MD (US); Yajun Zheng, Hockessin, DE (US); Linghang Zhuang, Chalfont, PA (US)

(73) Assignee: Vitae Pharamceuticals, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/182,749

(22) Filed: Jun. 15, 2016

(65) Prior Publication Data

US 2017/0136017 A1    May 18, 2017

Related U.S. Application Data

(63) Continuation of application No. 14/657,179, filed on Mar. 13, 2015, now Pat. No. 9,388,190, which is a continuation of application No. 14/385,688, filed as application No. PCT/US2013/031242 on Mar. 14, 2013, now Pat. No. 9,006,244.

(60) Provisional application No. 61/612,051, filed on Mar. 16, 2012.

(51) Int. Cl.
*A61K 31/506*    (2006.01)
*A61K 31/4985*   (2006.01)
*C07D 487/04*    (2006.01)

(52) U.S. Cl.
CPC ........ *A61K 31/506* (2013.01); *A61K 31/4985* (2013.01); *C07D 487/04* (2013.01)

(58) Field of Classification Search
CPC .......................... C07D 487/04; A61K 31/4985
USPC .................. 544/330, 332, 344, 346; 514/250
See application file for complete search history.

(56) References Cited

U.S. PATENT DOCUMENTS

| 4,748,247 | A  | 5/1988  | Abou-Gharbia |
| 5,356,862 | A  | 10/1994 | Zimmerman |
| 5,545,636 | A  | 8/1996  | Heath, Jr. et al. |
| 5,854,245 | A  | 12/1998 | Duggan et al. |
| 6,177,440 | B1 | 1/2001  | Bach et al. |
| 9,006,244 | B2 * | 4/2015 | Dong ................ A61K 31/4985 514/250 |
| 9,006,245 | B2 * | 4/2015 | Leftheris ........... A61K 31/4985 514/250 |
| 9,388,190 | B2 * | 7/2016 | Dong ................ A61K 31/4985 |
| 2004/0087601 | A1 | 5/2004 | Erickson et al. |
| 2006/0128713 | A1 | 6/2006 | Jolidon et al. |
| 2006/0276453 | A1 | 12/2006 | Goldberg et al. |
| 2007/0078138 | A1 | 4/2007 | Palladino et al. |
| 2007/0155761 | A1 | 7/2007 | Bissantz et al. |
| 2008/0221122 | A1 | 9/2008 | Palladino et al. |
| 2009/0186879 | A1 | 7/2009 | Aso et al. |
| 2009/0192147 | A1 | 7/2009 | Ayral-Kaloustian et al. |
| 2010/0137320 | A1 | 6/2010 | Huang et al. |

FOREIGN PATENT DOCUMENTS

| CN | 101456863 A  | 6/2009 |
| DE | 19802235 A1  | 7/1999 |
| EP | 572863 A1    | 12/1993 |
| EP | 950661 A1    | 10/1999 |
| FR | 2761073 A1   | 9/1998 |
| FR | 2829766 A1   | 3/2003 |
| JP | 2007-137810 A | 6/2007 |
| WO | 9110668 A1   | 7/1991 |
| WO | 9517182 A1   | 6/1995 |
| WO | 9612721 A1   | 5/1996 |
| WO | 9800134 A1   | 1/1998 |
| WO | 9800144 A1   | 1/1998 |
| WO | 9800401 A1   | 1/1998 |
| WO | 9842710 A1   | 10/1998 |
| WO | 00/68202 A1  | 11/2000 |
| WO | 01/09136 A1  | 2/2001 |
| WO | 01/30331 A2  | 5/2001 |
| WO | 01/49288 A1  | 7/2001 |
| WO | 02/10169 A1  | 2/2002 |
| WO | 0210169 A1   | 2/2002 |
| WO | 02/059082 A2 | 8/2002 |
| WO | 02/072584 A2 | 9/2002 |
| WO | 03/059353 A1 | 7/2003 |

(Continued)

OTHER PUBLICATIONS

U.S. Appl. No. 14/385,671, filed Sep. 16, 2014.
U.S. Appl. No. 14/721,262, filed May 26, 2015.
U.S. Appl. No. 14/657,179, filed Mar. 13, 2015.
International Search Report for International Application No. PCT/US2013/031242; International Filing Date: Mar. 4, 2013; dated Jun. 27, 2013; 11 pages.
Certified Indian Patent Application IN 2000MA00368, Oct. 2014.
Damasio, Alzheimer's Disease and Related Dementias, Cecil Textbook of Medicine, 20th Edition, vol. 2, pp. 1992-1996, 1996.
Layzer, "Degenerative Diseases of the Nervous System," Cecil Textbook of Medicine, 20th Edition, vol. 2, pp. 2050-2057, 1996.
Pearce, et al., "Failure Modes in Anticancer Drug Discovery and Development," Cancer Drug Design and Discovery, Edited by Stephen Neidle, Chapter 18, pp. 424-435, 2008.

(Continued)

*Primary Examiner* — Deepak Rao
(74) *Attorney, Agent, or Firm* — McCarter & English, LLP; Steven G. Davis; Michael J. DeGrazia

(57) ABSTRACT

Provided herein are novel compounds and pharmaceutically acceptable salts thereof that are liver X receptor modulators. Also provided are compositions comprising compounds of the invention and a carrier. Additionally, use of the compounds herein and methods for treating a disease or disorder associated with the liver X receptor are further described.

16 Claims, No Drawings

(56) References Cited

FOREIGN PATENT DOCUMENTS

| | | |
|---|---|---|
| WO | 2004/099212 A1 | 11/2004 |
| WO | 2005/077912 A1 | 8/2005 |
| WO | 2005/097108 A1 | 10/2005 |
| WO | 2005/105213 A2 | 11/2005 |
| WO | 2005/105805 A1 | 11/2005 |
| WO | 2005/113526 A2 | 12/2005 |
| WO | 2006/063709 A1 | 6/2006 |
| WO | 2006/072608 A2 | 7/2006 |
| WO | 2006/106423 A2 | 10/2006 |
| WO | 2007/006688 A1 | 1/2007 |
| WO | 2007/035841 A1 | 3/2007 |
| WO | 2007/048847 A2 | 5/2007 |
| WO | 2007/065820 A1 | 6/2007 |
| WO | 2007/088277 A1 | 8/2007 |
| WO | 2007/117180 A1 | 10/2007 |
| WO | 2008/122115 A1 | 10/2008 |
| WO | 2009/003003 A2 | 12/2008 |
| WO | 2009/042092 A1 | 4/2009 |
| WO | 2009/086129 A1 | 7/2009 |
| WO | 2009/118411 A2 | 10/2009 |
| WO | 2010/089084 A1 | 8/2010 |
| WO | 2010/142402 A1 | 12/2010 |
| WO | 2011/005295 A1 | 1/2011 |
| WO | 2011/031816 A2 | 3/2011 |
| WO | 2011/031818 A2 | 3/2011 |
| WO | 2011/071725 A1 | 6/2011 |
| WO | 2011/109237 A2 | 9/2011 |
| WO | 2013/138568 A1 | 9/2013 |

OTHER PUBLICATIONS

Simone, "Oncology: Introduction," Cecil Textbook of Medicine, 20th Edition, vol. 1, pp. 1004-1010, 1996.
Gura, et al., "Systems for Identifying New Drugs Are Often Faulty," Science, 278:1041-1042, 1997.
Johnson, et al., "Relationships Between Drug Activity in NCI Preclinical In Vitro and In Vivo Models and Early Clinical Trials," British Journal of Cancer, 84(10):1424-1431, 2001.
Jakobsson, et al., "Liver X Receptor Biology and Pharmacology: New Pathways, Challenges and Opportunities," Trends in Pharmacological Sciences, vol. 33, No. 7, pp. 394-404, 2012.

* cited by examiner

LIVER X RECEPTOR MODULATORS

REFERENCE TO RELATED APPLICATIONS

This application is a continuation of U.S. application Ser. No. 14/657,179, filed on Mar. 13, 2015, which is a continuation of U.S. application Ser. No. 14/385,688, now U.S. Pat. No. 9,006,244, filed on Sep. 16, 2014, which is a 35 U.S.C.§371 national stage filing of International Application No. PCT/US2013/031242, filed Mar. 14, 2013, which claims the benefit of the filing date of U.S. Provisional Application No. 61/612,051, filed on Mar. 16, 2012. The entire contents of the above applications are incorporated herein by reference.

FIELD OF THE INVENTION

The present invention relates to compounds that modulate the activity of liver X receptors.

BACKGROUND OF THE INVENTION

Atherosclerosis is the leading cause of death in the developed world, and atherosclerosis is predicted to be the leading cause of death in the developing world in the 21st century. Liver X receptors (LXRs) are ligand-activated transcription factors that play a crucial role in regulating the expression of genes involved in lipid metabolism and cellular cholesterol homeostasis. LXR agonists have been shown to enhance reverse cholesterol transport (RCT), facilitating cholesterol trafficking from the periphery back to the liver for processing and excretion. RCT occurs via upregulation of cholesterol transporters (ATP—Binding Cassettes: ABCA1 and ABCG1) in peripheral macrophages. Active RCT has the potential to inhibit the progression of atherosclerosis.

There are two isoforms of LXR, LXRα (NR1H3) and LXRβ (NR1H2) that are encoded by separate genes. LXRα expression is tissue-selective, detectable in liver, intestine, kidney, adipose tissue and adrenal glands, all of which are important for lipid homeostasis, whereas LXRβ is expressed ubiquitously. Both LXRs require the retinoid X receptor (RXR) as an obligate heterodimer partner to recognize and bind cooperatively to LXR response elements (LXREs) consisting of two direct repeats of a core hexameric sequence spaced by four nucleotides (DR4). The ligand binding domains of the two LXRs are fairly well conserved (~78% amino acid homology) and respond to endogenous ligands consisting of oxidized derivatives of cholesterol (oxysterols) that serve as intermediates in steroid hormone and bile acid synthesis. Among them, 22(R)-hydroxycholesterol, 24(S)-hydroxycholesterol, and 24(S), 25-epoxycholesterol are the most potent. These data suggested that LXRs are likely to play an important role in cholesterol regulation, which was later confirmed through gene knockout studies in mice. Non-steroidal ligands have also been identified, and, using these as chemical probes many LXR-regulated genes have been discovered. Several LXRE-containing genes are involved in cholesterol metabolism, reverse cholesterol transport (RCT) and lipogenesis. Other genes involved in inflammation and carbohydrate metabolism lack LXREs, but are repressed by LXRs in a ligand-dependent manner. Based on these discoveries, the liver X receptors have recently emerged as unprecedented targets acting as intracellular cholesterol sensors, providing the basis for the treatment of a variety of diseases, including atherosclerosis, diabetes, Alzheimer's disease, skin disorders, reproductive disorders and cancer (Viennois et al., 2011, Expert Opin. Ther. Targets, 15(2):219-232). Additionally, it has been determined that LXR agonists modulate intestinal and renal sodium phosphate (NaPi) transporters and, in turn, serum phosphate levels (Caldas et al., 2011, Kidney International, 80:535-544). Thus, LXR is also a target for kidney disorders, and particularly for the prevention of hyperphosphatemia and associated cardiovascular complications. Recently, LXRs have been identified as targets in the treatment of osteoporosis and related diseases (Kleyer et al., 2012, J. Bone Miner. Res., 27(12):2442-51).

Alzheimer's disease is one of the most common forms of dementia, characterized by the accumulation and deposition of amyloid-beta (Aβ) peptides in the brain, leading to the perturbation of synaptic function and neuronal loss in the brains of affected individuals. Neurons in the brain produce Aβ peptides via cleavage of amyloid precursor protein (APP), and Aβ peptides are normally cleared through efflux into the peripheral circulation and by degradation by proteinases within the brain.

Apolipoprotein E (apoE) is associated with age-related risk for Alzheimer's disease and plays critical roles in Aβ homeostasis. LXR increases the expression of apoE and increases the lipidation of apoE. Degradation of Aβ both intra- and extracellularly is enhanced by lipidated apoE. LXR agonist treatment stimulated proteolytic degradation of Aβ, reduced plaque pathology, and improved memory in APP-expressing transgenic mice (Jiang et al., 2008, Neuron, 58:681-693).

In skin, keratinocytes are a critical component of the epidermis. The outer layer, stratum corneum, is primarily responsible for the permeability barrier to water and electrolyte transit. Keratinocytes in the epidermis undergo differentiation which culminates in keratinocyte cornification ("the bricks") and in formation of the extracellular lipid-enriched lamellar membranes ("the mortar") in the stratum corneum. Both LXRα and LXRβ are expressed in keratinocytes, and LXR expression and activation promotes epidermis barrier function. Activation of LXR is involved in keratinocyte differentiation, formation of the lamellar membrane and overall improvement of epidermal barrier function. Thus, LXR activation is expected to result in increased keratinocyte differentiation, increased lipid secretion (via ABCA1, ABCA12), and increased lamellar body formation, leading to a healthy epidermis (smooth skin).

The potential therapeutic utility of LXR agonists has led to the development of several high affinity LXR ligands with potent agonism for both receptor subtypes. The therapeutic utility of LXR agonists is constrained by their potential to induce lipogenic genes including sterol response element binding protein-1c (SREBP1c) and fatty acid synthase (FAS). Preclinical studies have demonstrated that synthetic modulators of LXRs reduce lesion progression in murine models of atherosclerosis with limited increase in hepatic lipogenesis. There is a clear need for new LXR chemotypes that retain the anti-atherosclerotic efficacy of current LXR agonists but are devoid of lipogenic activity. Compounds exhibiting a pharmacological profile with positive effects on RCT while being neutral or suppressive on lipogenic genes will be valuable therapeutic agents in patients with atherosclerotic dyslipidemia.

The present invention provides compounds that are liver X receptor agonists and are useful as therapeutic agents for the promotion of reverse cholesterol transport and the suppression of hepatic lipogenesis, and for the prevention, amelioration or treatment of diseases or disorders including atherosclerosis, Alzheimer's disease, dermatitis, and dyslipidemia in a patient.

SUMMARY OF THE INVENTION

Disclosed are LXR modulators that are useful as therapeutic agents for the promotion of reverse cholesterol transport and the suppression of hepatic lipogenesis, and for the prevention, amelioration or treatment of diseases or disorders including atherosclerosis and dyslipidemia in a subject. The disclosed LXR modulators are selective for the LXRβ subtype over the LXRα subtype (see e.g., Example 2, isomer 1 and Example 4, isomer 1).

One embodiment of the invention is a compound represented by structural formula I:

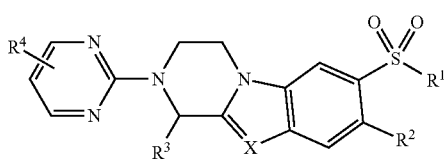

I or a pharmaceutically acceptable salt thereof.

X is N or $CR^c$.

$R^1$ is alkyl or $—NR^aR^b$.

$R^2$ is H; halogen; —CN; —NRC(O)R; —C(O)OR; —C(O)$NR^aR^b$; monocyclic heteroaromatic optionally substituted with one or more groups selected from alkyl, —CN, —NRC(O)R, —C(O)OR, —C(O)$NR^aR^b$ and halogen; monocyclic non-aromatic heterocycle optionally substituted with one or more groups selected from alkyl, halogen, —CN and =O; or alkyl optionally substituted by one or more groups selected from halogen, hydroxy, alkoxy, $—NR^aR^b$, —NRC(O)R, —NRC(O)O(alkyl), —NRC(O)N(R)$_2$, —C(O)OR, thiol, alkylthiol, nitro, —CN, =O, —OC(O)H, —OC(O)(alkyl), —OC(O)O(alkyl), —OC(O)N(R)$_2$ and —C(O)$NR^aR^b$.

$R^3$ is alkyl, haloalkyl, hydroxyalkyl, alkoxyalkyl, cycloalkyl, monocyclic non-aromatic heterocycle, monocyclic heteroaromatic or phenyl, wherein the phenyl, monocyclic non-aromatic heterocycle and monocyclic heteroaromatic group represented by $R^3$ are optionally substituted with one or more groups selected from alkyl, halogen, haloalkyl, alkoxy, haloalkoxy, nitro and —CN.

$R^4$ is halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R —SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl, monocyclic non-aromatic heterocycle, monocyclic heteroaromatic or alkyl, wherein the monocyclic non-aromatic heterocycle, monocyclic heteroaromatic and alkyl group represented by $R^4$ are optionally substituted with one or more group selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O (alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$.

Each R independently is H or alkyl.

$R^a$ and $R^b$ are independently H, alkyl or $R^a$ and $R^b$ can be taken together with the nitrogen to which they are attached to form a monocyclic non-aromatic heterocycle.

$R^c$ is H, alkyl, or halogen.

Another aspect of the invention is a pharmaceutical composition comprising a compound of the invention and a pharmaceutically acceptable carrier or diluent.

A further aspect of the present invention also provides for a method of treating a subject with a disease or disorder that is treatable by upregulating LXR activity. The method comprises administering an effective amount of a compound of the invention or a pharmaceutically acceptable salt thereof to the subject in need thereof.

Also provided in the invention is the use of a compound of the invention for the manufacture of a medicament for treating a subject with a disease or disorder that is treatable by upregulating LXR activity in a subject in need thereof.

Disclosed herein is also a compound of the invention for use in treating a disease or disorder that is treatable by upregulating LXR activity in a subject in need thereof

DETAILED DESCRIPTION OF THE INVENTION

A. Compounds

The compound(s) of the invention provided herein include both the neutral form and a pharmaceutically acceptable salt thereof.

In one embodiment, the compound is represented by structural formula II, III, IV, V, or VI, wherein the values for the variables are as defined for Formula I above.

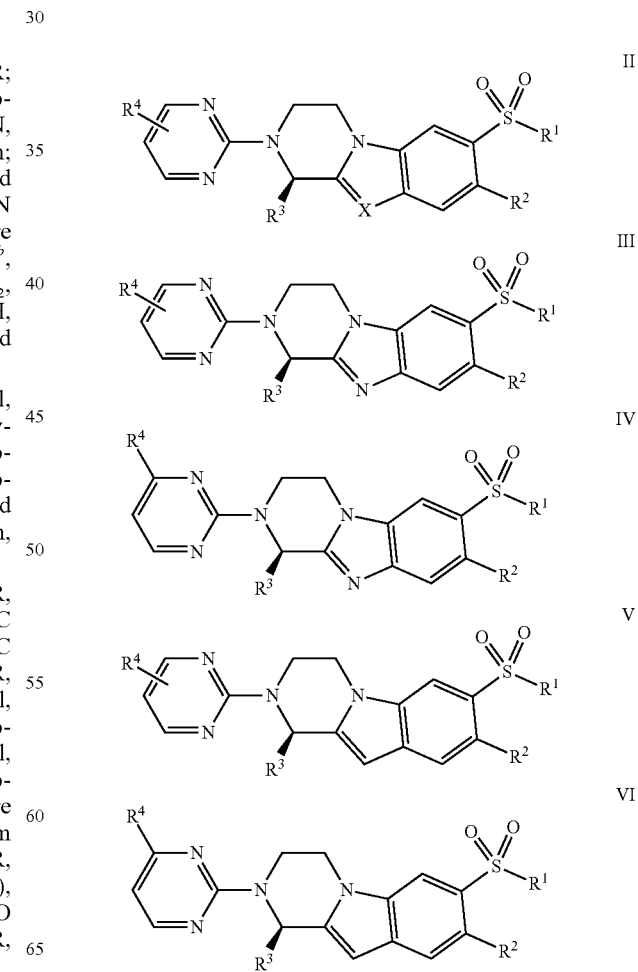

In a first alternative embodiment of any compound of formulas I through VI, the variables are defined as follows:

$R^3$ is alkyl, haloalkyl, hydroxyalkyl, alkoxyalkyl, cycloalkyl or phenyl, wherein the phenyl represented by $R^3$ is optionally substituted with one or more groups selected from alkyl, halogen, haloalkyl, alkoxy, haloalkoxy, nitro and —CN; and $R^4$ is halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl or alkyl, wherein the alkyl group represented by $R^4$ is optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$.

The values for the remaining variables are as defined for Formula I.

In a second alternative embodiment of any compound of formulas I through VI, the variables are defined as follows.

$R^1$ is methyl or —NH$_2$.

$R^2$ is H or methyl, wherein the methyl group represented by $R^2$ is optionally substituted with one or more groups selected from halogen hydroxyl, alkoxy, —NR$^a$R$^b$, —NRC(O)R, —NRC(O)O(alkyl), —NRC(O)N(R)$^2$, —C(O)OR, thiol, alkylthiol, nitro, —CN, =O, —OC(O)H, —OC(O)(alkyl), —OC(O)O(alkyl), —C(O)NR$^a$R$^b$ and —OC(O)N(R)$_2$. Preferably, $R^2$ is H or —CH$_2$OH.

$R^3$ is methyl, ethyl, propyl, isopropyl, tert-butyl, sec-butyl, iso-butyl, —CH$_2$CF$_3$, —CH(CH$_2$F)$_2$, —CH(CHF$_2$)$_2$, —CH(CF$_3$)$_2$, —CF(CH$_3$)$_2$, —CF$_3$, cyclopropyl, cyclobutyl, cyclopentyl, cyclohexyl, —C(OH)(CH$_3$)$_2$, —CH(OH)(CH$_3$), or phenyl, wherein the phenyl group represented by $R^3$ is optionally substituted with one or more groups selected from alkyl, halogen, haloalkyl, alkoxy, haloalkoxy, nitro and —CN.

$R^c$, where present, is H.

The values for the remaining variables are as defined for Formula I or in the first alternative embodiment.

In a third alternative embodiment of any compound of formulas I through VI, $R^1$ is methyl; $R^2$ is —CH$_2$OH; and $R^3$ is isopropyl. The values for the remaining variables are as defined for Formula I or for the first or second alternative embodiment.

In a fourth alternative embodiment of any compound of formulas I through VI, $R^4$ is halogen, hydroxy, alkyl, cycloalkyl, cycloalkoxy, alkoxy, haloalkoxy, haloalkyl, —N(R)$_2$, —C(O)OH, —C(O)O(alkyl), —C(O)O(haloalkyl), —C(O)(alkyl), —C(O)N(R)$_2$, —NRC(O)R, —SO$_2$N(R)$_2$, —OC(O)N(R)$_2$, —CN, hydroxyalkyl or dihydroxyalkyl. The values for the remaining variables are as defined for Formula I or for the first, second or third alternative embodiments.

In a fifth alternative embodiment of any compound of formulas I through VI, $R^4$ is alkyl, haloalkyl, cycloalkyl, alkoxy, or haloalkoxy. The values for the remaining variables are as defined for Formula I or for the first, second or third alternative embodiments.

In a sixth alternative embodiment of any compound of formulas I through VI, $R^4$ is methyl, ethyl, hydroxy, —CF$_3$, isopropyl, cyclopropyl, —CH$_2$OH, —CH(OH)(CH$_2$)(OH), —C(OH)(CH$_3$)$_2$, —CH(OH)(CH$_3$), —CH(OH)(CH$_2$)(CH$_3$), —CH(OH)(CH$_2$)$_2$(CH$_3$), —C(O)NH$_2$, —C(O)N(CH$_3$)$_2$, —C(O)OH, —C(O)NH(CH$_3$), —C(O)CH$_3$, —C(O)CH$_2$CH$_3$, —C(O)O(CH$_2$)(CH$_3$), —C(O)O(tert-butyl), —C(O)O(C)(CH$_3$)$_2$(CF$_3$), —NHC(O)CH$_3$, —OCHF$_2$, —OCF$_3$, —OCH$_2$CH$_3$, —OCH(CH$_3$)$_2$ or —OCH$_3$. Preferably, $R^5$ is —C(CH$_3$)$_2$OH. The values for the remaining variables are as defined for Formula I or for the first, second or third embodiments.

In a seventh alternative embodiment of any compound of formulas I through VI, $R^4$ is methyl, halogenated methyl, cyclopropyl, —OCHF$_2$ or —OCH$_3$. Preferably, $R^4$ is CF$_3$. The values for the remaining variables are as defined for Formula I or for the first, second or third alternative embodiments.

Another embodiment of the invention is a compound represented by formula I, II, III, IV, V or VI or a pharmaceutically acceptable salt thereof, wherein the variables are as defined for formula (I) or in the first, second or third alternative embodiments, provided that the compound comprises at least one group represented by —C(O)OR.

Another embodiment of the invention is a compound represented by formula I, II, III, IV V or VI or a pharmaceutically acceptable salt thereof, wherein the variables are as defined for formula (I) or in the first, second, third, fourth, fifth, sixth or seventh alternative embodiment, provided that the compound comprises no groups represented by —C(O)OR.

The compounds of the invention contain at least one chiral center and, therefore, exist as enantiomers. When compounds of the invention are depicted or named without indicating the stereochemistry, it is to be understood that enantiomerically pure forms and mixtures of enantiomers, including racemic mixtures, are encompassed.

When a compound is designated by a name or structure that indicates a single enantiomer, unless indicated otherwise, the compound is at least 50%, 60%, 70%, 80%, 90%, 95%, 99%, 99.5% or 99.9% optically pure (also referred to as "enantiomerically pure"). Optical purity is the weight in the mixture of the named or depicted enantiomer divided by the total weight in the mixture of both enantiomers.

In a seventh alternative embodiment, a compound of the invention is depicted by a compound in Table 1 or a pharmaceutically acceptable salt thereof.

TABLE 1

| Compound No. | Example No. | Structure |
|---|---|---|
| E1 | Example 1 | 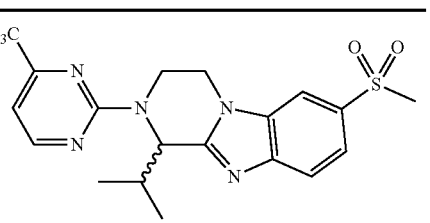 |

TABLE 1-continued

| Compound No. | Example No. | Structure |
|---|---|---|
| E2a | Example 2, isomer 1 | 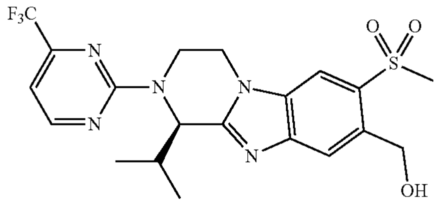 |
| E2b | Example 2, isomer 2 | 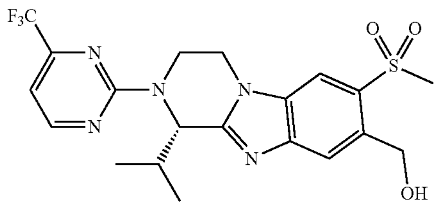 |
| E3a | Example 3, isomer 1 | 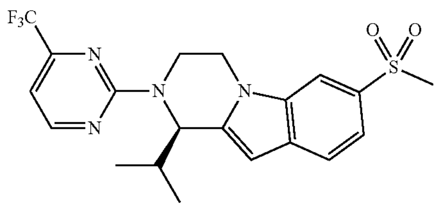 [SMILES: CC(C)[C@@H]1c2cc3ccc(S(C)(=O)=O)cc3n2CCN1c1nccc(C(F)(F)F)n1] |
| E3b | Example 3, isomer 2 | 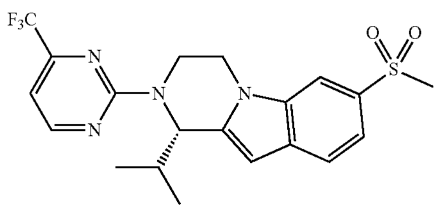 [SMILES: CC(C)[C@H]1c2cc3ccc(S(C)(=O)=O)cc3n2CCN1c1nccc(C(F)(F)F)n1] |
| E4a | Example 4, isomer 1 | 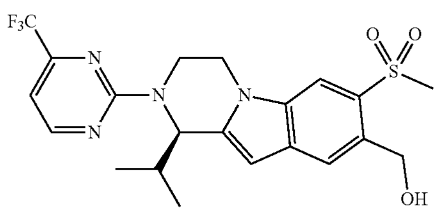 [SMILES: CC(C)[C@@H]1c2cc3cc(CO)c(S(C)(=O)=O)cc3n2CCN1c1nccc(C(F)(F)F)n1] |
| E4b | Example 4, isomer 2 | 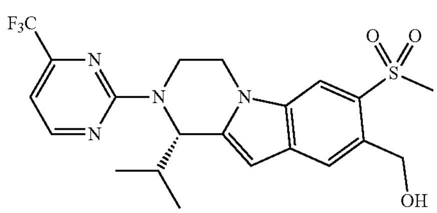 [SMILES: CC(C)[C@H]1c2cc3cc(CO)c(S(C)(=O)=O)cc3n2CCN1c1nccc(C(F)(F)F)n1] |

B. Definitions

Unless otherwise specified, the below terms used herein are defined as follows.

"Subject", "patient" and "mammal" are used interchangeably herein. In one embodiment, the subject is a non-human animal such as a non-human primate (e.g., a monkey, chimpanzee), a farm animal (e.g., a horse, cow, pig, chicken, or sheep), a laboratory animal (e.g., a rat or mouse), or a companion animal (e.g., dog, cat, guinea pig or rabbit). In a preferred embodiment, the subject is a human.

"Compound(s) of the invention" refers to compounds represented by Structural Formula I, II, III, VI, V, VI; a compound depicted in Table 1; a compound named or depicted in the examples herein as the final compound(s) of the examples; or a pharmaceutically acceptable salt thereof. "Compound(s) of the invention" also includes the neutral form of the compounds as depicted herein.

"Pharmaceutically acceptable" refers to a component that is, within the scope of sound medical judgment, suitable for use in contact with the tissues of the subject, such as humans and other mammals, without undue toxicity, irritation, allergic response and the like, and are commensurate with a reasonable benefit/risk ratio.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Lists of suitable salts are found in Remington's Pharmaceutical Sciences, 18th ed., Mack Publishing Company, Easton, Pa., 1990, p 1445, the disclosure of which is hereby incorporated by reference.

"Liver X receptors or LXRs" includes both the $\alpha$ and $\beta$ subtypes of the liver X receptor. In one embodiment, the disclosed compounds selectively bind and upregulate the activity of the LXR$\beta$ subtype over the LXR$\alpha$ subtype. To "modulate" a receptor means that there is a change or alteration in the activity of a molecule of interest, e.g., the biological activity of liver X receptor. Modulation may be an upregulation (increase) or a downregulation (decrease) in the magnitude of a certain activity or function of the molecule of interest. Exemplary activities and functions of a molecule include, but are not limited to, binding characteristics, enzymatic activity, cell receptor activation, transcriptional activity, and signal transduction. In an embodiment, the compounds of the invention are LXR agonists that, for example, upregulate or downregulate genes which are transcriptional targets of LXR (i.e., "LXR target genes").

"Treat" or "treating" include both therapeutic and prophylactic treatments and mean to ameliorate, decrease, suppress, attenuate, diminish, arrest, or stabilize the development or progression of a disease (e.g., a disease or disorder delineated herein), lessen the severity of the disease or improve the symptoms associated with the disease.

"Disease" or "disorder" means any condition that is modulated or otherwise affected by LXR activity or in which LXR activity is implicated. The diseases or disorders include those which are associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

"Effective amount" is the quantity of the compound which is sufficient to treat (therapeutically or prophylactically) the target disorder or in which a beneficial clinical outcome is achieved when the compound is administered to a subject in a proper dosing regimen. Effective doses will also vary, as recognized by one of ordinary skill in the art, depending on the disease being treated, the severity of the disease, the route of administration, the sex, age and general health condition of the patient, excipient usage, the possibility of co-usage with other therapeutic treatments such as use of other agents and the judgment of the treating physician or other medical provider. For example, an effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment. When a compound of the invention is administered to a subject with a disorder such as atherosclerosis, a "beneficial clinical outcome" includes reduction in the severity or number of symptoms associated with the disorder, lower cholesterol, or increase in the longevity of the subject compared with the absence of the treatment. The recommended dosages of agents currently used for the treatment of a disorder can be obtained from various references in the art including, but not limited to, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) 57th Ed., 2003, Medical Economics Co., Inc., Montvale, N.J., each of which is incorporated herein by reference in its entirety. In certain embodiments, an effective amount of a compound of this invention is in the range of from 0.5 mg to 2000 mg, or from 0.5 mg to 1000 mg, or from 0.5 mg to 500 mg, or from 0.5 mg to 100 mg, or from 100 mg to 1000 mg, or from 20 mg to 2000 mg per treatment. Treatment typically is administered from one to three times daily.

"Halo" or "halogen" means chloro, bromo, fluoro, or iodo. In one embodiment, halo is fluoro.

"Alkyl" means a straight or branched hydrocarbon group having 1 to 15 carbon atoms in the chain. In one embodiment, alkyl groups have 1 to 12 carbon atoms in the chain. In another embodiment, alkyl groups have 1 to 6 carbon atoms. Exemplary alkyl groups include, but are not limited to, methyl, ethyl, n-propyl, isopropyl, n-butyl, tert-butyl, sec-butyl, n-pentyl, 3-pentyl, heptyl, octyl, nonyl, decyl, and dodecyl.

"Alkoxy" is an alkyl group which is attached to another moiety via an oxygen linker (—O(alkyl)). Non-limiting examples include methoxy, ethoxy, propoxy, and butoxy.

"Haloalkyl" or "halogenated alkyl" means an alkyl group in which one or more, including all, of the hydrogen radicals are replaced by a halo group, wherein each halo group is independently selected from —F, —Cl, —Br, and —I. For example, the term "halomethyl" or "halogenated methyl" means a methyl in which one to three hydrogen radical(s) have been replaced by a halo group. Representative haloalkyl groups include fluoromethyl, difluoromethyl, trifluoromethyl, bromomethyl, 1,2-dichloroethyl, 4-iodobutyl, 2-fluoropentyl, and the like. Other examples include groups such as but are not limited to —$CH_2CF_3$, —$CH(CH_2F)_2$, —$CH(CHF_2)_2$, —$CH(CF_3)_2$, —$CF(CH_3)_2$, —$CF_3$.

"Haloalkoxy" is a haloalkyl group which is attached to another moiety via an oxygen linker such as but are not limited to —$OCHCF_2$ or —$OCF_3$.

"Alkoxyalkyl" is an alkoxy group which is attached to another moiety via an alkyl linker. "Hydroxyalkyl" or "dihydroxyalkyl" is one or two hydroxy groups, respectively, which are attached to another moiety via an alkyl linker. Representative "hydroxyalkyl" or "dihydroxyalkyl" include —$CH_2OH$, —$CH(OH)(CH_2)(OH)$, —$C(OH)(CH_3)_2$, —$CH(OH)(CH_3)$, —$CH(OH)(CH_2)(CH_3)$, —$CH(OH)(CH_2)_2(CH_3)$, —$C(CH_3)_2(OH)$, and the like.

"Cycloalkyl" means a non-aromatic monocyclic ring system of 3 to 10 carbon atoms. In one embodiment, the cycloalkyl group has 3 to 6 carbon atoms. Exemplary cycloalkyl rings include cyclopropyl, cyclobutyl, cyclopentyl, and cyclohexyl.

"Cycloalkoxy" means a cycloalkyl group which is attached to another moiety via an oxygen linker (—O(cycloalkyl)).

"Monocyclic non-aromatic heterocycle" means a single saturated heterocyclic ring, typically having 3- to 10-members and more typically 3 to 7-members in the ring, wherein at least one atom in the ring is a heteroatom such as, for example, nitrogen, oxygen, sulfur, including sulfoxide and sulfone. A 3- to 4-membered monocyclic non-aromatic heterocycle can contain up to 2 heteroatoms; a 5-6 membered monocyclic heterocycle can contain up to 3 heteroatoms and a 7- to 10-membered monocyclic non-aromatic heterocycle can contain up to 4 heteroatoms. The monocyclic non-aromatic heterocycle may be attached to another group via any heteroatom or carbon atom of the monocyclic non-aromatic heterocycle. Representative monocyclic non-aromatic heterocycles include morpholinyl, thiomorpholinyl, pyrrolidinonyl, pyrrolidinyl, piperidinyl, piperazinyl, imidazolidinyl, pyrazolidinyl, oxazolidinyl, isothiazolidinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. In one embodiment, a monocyclic non-aromatic heterocycle is a heterocyclic ring of 4, 5, 6, or 7 members.

"Monocyclic heteroaromatic" comprises carbon atom ring members and one or more heteroatom ring members. Each heteroatom is independently selected from nitrogen, oxygen, and sulfur, including sulfoxide and sulfone. The point of attachment of a monocyclic heteroaromatic ring to another group may be at either a carbon atom or a heteroatom of the heteroaromatic. In one embodiment, the monocyclic heteroaromatic ring is selected from 5 to 8 membered monocyclic heteroaromatic rings. Representative monocyclic heteroaromatic groups include pyridyl, 1-oxo-pyridyl, furanyl, thienyl, pyrrolyl, oxazolyl, imidazolyl, thiazolyl, isoxazolyl, pyrazolyl, isothiazolyl, pyridazinyl, pyrimidinyl, pyrazinyl, a triazinyl, triazolyl, thiadiazolyl, and tetrazolyl.

C. Pharmaceutical Compositions, Formulations and Dosages

In one embodiment, provided herein is a pharmaceutical composition comprising a compound of the invention and a pharmaceutically acceptable carrier or diluent.

In the pharmaceutical compositions of the invention, the compound of the invention is present in an effective amount. The interrelationship of dosages for animals and humans (based on milligrams per meter squared of body surface) is described in Freireich et al., Cancer Chemother. Rep, 1966, 50:219. Body surface area may be determined approximately from height and weight of the patient. See, e.g., Scientific Tables, Geigy Pharmaceuticals, Ardsley, N.Y., 1970, 537.

The LXR modulators herein (e.g., compound(s) of the invention) can be formulated as pharmaceutical compositions and administered to a subject, such as a human, in a variety of forms adapted to the chosen route of administration. Typical routes of administering such pharmaceutical compositions include, without limitation, oral, topical, buccal, transdermal, inhalation, parenteral, sublingual, rectal, vaginal, and intranasal. The term parenteral as used herein includes subcutaneous injections, intravenous, intramuscular, intrathecal, intrasternal injection or infusion techniques.

Methods of formulating pharmaceutical compositions are well known in the art, for example, as disclosed in "Remington: The Science and Practice of Pharmacy," University of the Sciences in Philadelphia, ed., 21st edition, 2005, Lippincott, Williams & Wilkins, Philadelphia, Pa. Each of the LXR modulators may be used alone or in combination as a part of a pharmaceutical composition of the invention.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Thus, the present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like.

Suitable tablets may be obtained, for example, by mixing one or more compounds of the invention with known excipients, for example inert diluents, carriers, disintegrants, adjuvants, surfactants, binders and/or lubricants. The tablets may also consist of several layers.

The compounds of the invention can be suitably formulated into pharmaceutical compositions for administration to a subject. The pharmaceutical compositions of the invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the invention may be incorporated with excipient and used in the form of ingestible tablets, buccal tablets, troches, capsules, elixirs, suspensions, syrups, wafers, and the like.

Typically for parenteral administration, solutions of a compound of the invention can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the invention for the extemporaneous preparation of sterile injectable solutions or dispersions.

For nasal administration, the compounds of the invention can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer For buccal or sublingual administration, the compounds of the invention can be formulated with a carrier such as sugar, acacia, tragacanth, or gelatin and glycerine, as tablets, lozenges or pastilles.

For rectal administration, the compounds of the invention can be formulated in the form of suppositories containing a conventional suppository base such as cocoa butter.

Topical and/or local administration of the compounds of the invention can be achieved in a variety of ways including but not limited to ointments, lotions, pastes, creams, gels, powders, drops, sprays, solutions, inhalants, patches, suppositories, retention enemas, chewable or suckable tablets or pellets and aerosols. Topical and/or local administration may also involve the use of transdermal administration such as transdermal patches or iontophoresis devices. For topical and/or local administration, the compounds of the invention can be formulated as ointments, creams, milks, salves, powders, impregnated pads, syndets, solutions, gels, sprays, foams, suspensions, lotions, sticks, shampoos or washing bases. Compounds of the invention may also be administered in the form of suspensions of lipid or polymer vesicles or nanospheres or microspheres or polymer patches and hydrogels for controlled release.

D. Methods of Treatment and Use of the LXR Modulators

Provided herein is a method of treating a subject with a disease or disorder that is treatable by modulation of LXR. In one embodiment, LXR is modulated by upregulating LXR activity. The method comprises administering an effective amount of the compound of the invention. Moreover, provided herein is the use of a compound of the invention for the manufacture of a medicament for treating a subject with a disease or disorder that is treatable by upregulating LXR activity in a subject in need thereof.

The methods provided herein may be useful for disorders treatable with LXR modulation, in particular LXR agonism.

Compounds of the invention are useful for the treatment or prevention of diseases or disorders associated with altered cholesterol transport, reverse cholesterol transport, fatty acid metabolism, cholesterol absorption, cholesterol re-absorption, cholesterol secretion, cholesterol excretion, or cholesterol metabolism. Representative diseases or disorders include, but are not limited to, a lipid disorder; cancer, particularly hormone-dependent cancers, including ovarian, breast and prostate cancer; acneiform skin condition; skin inflammatory disease; immunological disorder; condition characterized by a perturbed epidermal barrier function; condition of disturbed differentiation or excess proliferation of the epidermis or mucous membrane; cardiovascular disease; reproductive tract disorders; optic nerve and retinal pathology; degenerative neuropathy occurring in a disease; autoimmune disease; traumatic damage to the central or peripheral nervous system; neurodegenerative disease; a degenerative process due to aging; diseases or disorders of the kidney; and osteoporosis and related diseases.

In another embodiment, the disease or disorder is hyperlipidemia, hypercholesterolemia, hyperlipoproteinemia, hypertriglyceridemia, lipodystrophy, hepatic steatosis, nonalcoholic steatohepatitis (NASH), nonalcoholic fatty liver disease (NAFLD), hyperglycemia, insulin resistance, diabetes mellitus, dyslipidemia, atherosclerosis, gallstone disease, acne vulgaris, dermatitis (including but not limited to, psoriasis, contact dermatitis, atopic dermatitis, and eczema), skin wounds, skin aging, photoaging, wrinkling, diabetes, Niemann-Pick disease type C, Parkinson's disease, Alzheimer's disease, inflammation, xanthoma, obesity, metabolic syndrome, syndrome X, stroke, peripheral occlusive disease, memory loss, diabetic neuropathies, proteinuria, glomerulopathies (including but not limited to, diabetic nephropathy, hypertensive nephropathy, IGA nephropathy, focal segmental glomerulosclerosis), hyperphosphatemia, cardiovascular complications of hyperphosphatemia, cancer, multiple sclerosis, or osteoporosis.

In another embodiment, the disease or disorder is common acne; comedones; polymorphs; rosacea; nodulocystic acne; acne conglobate; senile acne; secondary acne, including but not limited to solar, medicinal and occupational acne; ichthyosis; ichthyosiform conditions; Darier's disease; palmoplantar keratoderma; leukoplakia; leukoplakiform conditions; cutaneous or mucous (oral) lichen; dermatological conditions or afflictions with an inflammatory immunoallergic component, with or without a cellular proliferation disorder, including but not limited to cutaneous psoriasis, mucous psoriasis, ungual psoriasis, psoriatic rheumatism, cutaneous atopy, including eczema, respiratory atopy and gingival hypertrophy; benign or malignant dermal or epidermal proliferations, of viral or non-viral origin, including but not limited to common warts, flat warts, epidermodysplasia verruciformis, oral or florid papillomatoses, and T lymphoma or cutaneous T-cell lymphoma; proliferations that may be induced by ultraviolet light, including but not limited to basocellular epithelioma and spinocellular epithelioma; precancerous skin lesions, including but not limited to keratoacanthomas; immune dermatitides, including but not limited to lupus erythematosus; bullous immune diseases; collagen diseases, including but not limited to scleroderma; dermatological or systemic conditions or afflictions with an immunological component; skin disorders due to exposure to UV radiation; photo-induced or chronological aging of the skin; actinic pigmentations; keratosis; pathology associated with chronological or actinic aging, including but not limited to xerosis; sebaceous function disorders, including but not limited to hyperseborrhea of acne, simple seborrhea and seborrhoeic dermatitis; cicatrization disorders, including but not limited to stretch marks; pigmentation disorders, including but not limited to hyperpigmentation, melasma, hypopigmentation, and vitiligo; and alopecia, including but not limited to chemotherapy-associated alopecia and radiation-associated alopecia.

In an embodiment, the disease or disorder is hypercholesterolemia, atherosclerosis or dyslipidemia. In another embodiment, the disease or disorder is atherosclerosis or dyslipidemia. In yet another embodiment, the disease or disorder is atherosclerosis, Alzheimer's disease or dermatitis.

The present invention also provides a method for increasing reverse cholesterol transport and/or for inhibiting the progression of or promoting the regression of atherosclerosis.

The present invention also provides a method of treating diseases or disorders associated with a need for increasing high density lipoprotein (HDL)-cholesterol levels comprising the administration of an effective amount of a compound of the invention to a mammal (particularly a human) in need thereof.

The present invention also provides a method of treating a disease or disorder associated with a need for decreasing low density lipoprotein (LDL)-cholesterol levels comprising the administration of an effective amount of a compound of the invention to a mammal (particularly a human) in need thereof.

Additionally, provided herein is a method of increasing the expression of an ATP-Binding Cassette protein in a subject's cells, thereby increasing reverse cholesterol transport in a subject using the compounds of the invention and compositions provided herein.

Standard physiological, pharmacological and biochemical procedures are known to the art and are available for evaluating compounds of the present invention for the ability to modulate LXR activity. Such assays include, for example, binding assays, fluorescence polarization assays, FRET based co-activator recruitment assays, and cell-based co-transfection assays. Compounds of the present invention can be evaluated for their ability to modulate the expression of genes known to be modulated by LXR. Established animal models can be used to study the profiles of compounds of the present invention in relation to parameters directly relevant to diseases or disorders, including atherosclerosis, Alzheimer's disease, and skin conditions. Thus, compounds of the present invention can be tested in vivo in animal models by a variety of routes of administration, for example, oral gavage. Typically, in vivo compound exposure can be examined in plasma and in tissues of interest. LXR activity (as detected by gene expression of LXR-responsive genes) can be examined in whole blood and tissues of interest. Lipids can be quantified in the plasma and the liver.

In particular, compounds of the present invention can be tested for their activity on ATP-Binding Cassette (ABC) cholesterol transporters, such as ABCA1 and ABCG1, and on lipogenic markers, such as SREBP1c at the gene and protein expression level. The functional consequences of ABC transporter induction can be examined in cellular models for cholesterol efflux and in animal models for the reverse cholesterol pathway and atherosclerosis. Lipogenic markers can be examined in animal models by measuring plasma and liver triglyceride levels.

The compounds of the present invention can be used alone (i.e., as a monotherapy) or in combination with one or more other therapeutic agent effective for treating any of the above indications. The pharmaceutical compositions can comprise the disclosed compounds alone as the only pharmaceutically active agent or can comprise one or more additional pharmaceutically active agents.

The present invention also provides combination therapy for treating or ameliorating a disease or a disorder described herein. In some embodiments, the combination therapy comprises administering at least one compound represented by Structural Formula I, II, III, IV, V, or VI in combination with one or more agents for treating or ameliorating a disease or a disorder described herein. In some embodiments, the combination therapy comprises administering at least one compound represented by Structural Formula I, II, III, IV, V, or VI in combination with one or more agents for the treatment of diseases including hyperlipidemia, hypercholesterolemia, hyperlipoproteinemia, hypertriglyceridemia, lipodystrophy, hepatic steatosis, NASH, NAFLD, hyperglycemia, insulin resistance, diabetes mellitus, dyslipidemia, atherosclerosis, gallstone disease, acne vulgaris, dermatitis (including but not limited to, psoriasis, contact dermatitis, atopic dermatitis, and eczema), skin wounds, skin aging, photoaging, wrinkling, diabetes, Niemann-Pick disease type C, Parkinson's disease, Alzheimer's disease, inflammation, xanthoma, obesity, metabolic syndrome, syndrome X, stroke, peripheral occlusive disease, memory loss, diabetic neuropathies, proteinuria, glomerulopathies (including but not limited to, diabetic nephropathy, hypertensive nephropathy, IGA nephropathy, focal segmental glomerulosclerosis), hyperphosphatemia, cardiovascular complications of hyperphosphatemia, cancer, multiple sclerosis or osteoporosis.

In some embodiments, the compounds of the invention are used in combination with one or more additional agents for the treatment of diabetes, dyslipidemia, cardiovascular disease, hypertension, or obesity. Agents for the treatment of diabetes include insulins, such as Humulin® (Eli Lilly), Lantus® (Sanofi Aventis), Novolin® (Novo Nordisk), and Exubera® (Pfizer); PPAR gamma agonists, such as Avandia® (rosiglitazone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophage®/Glucophage XR® (metformin HCl, Bristol Myers Squibb) and Glumetza® (metformin HCl extended release tablets, Depomed); thiazolidinediones; amylin analogs, GLP-1 analogs or agonists (including Byetta® (exenatide, Amylin/Eli Lilly) and Victoza® (recombinant liraglutide, Novo Nordisk)); DPP-IV inhibitors including Tradjenta™ (Eli Lilly/Boehringer Ingelheim), Januvia® (Merck), Galvus® (Novartis), and Onglyza® (Bristol-Myers Squibb/AstraZeneca); PTB-1 B inhibitors; protein kinase inhibitors (including AMP-activated protein kinase inhibitors); glucagon antagonists, glycogen synthase kinase-3 beta inhibitors; glucose-6-phosphatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimibe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists. Agents for the treatment of obesity include orlistat, phentermine, sibutramine and rimonabant.

An embodiment of the invention includes administering an LXR modulator compound of the invention or composition thereof in a combination therapy with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

In some embodiments, the combination therapy comprises administering at least one compound of the invention in combination with one or more compound selected from the group of, for example, beta secretase (BACE1) inhibitors; gamma-secretase inhibitors; amyloid aggregation inhibitors (e.g., ELND-005); directly or indirectly acting neuroprotective and/or disease-modifying substances; anti-oxidants (e.g., vitamin E or ginkgolide); anti-inflammatory substances (e.g., Cox inhibitors, NSAIDs); HMG-CoA reductase inhibitors (statins); acetylcholinesterase inhibitors (e.g., donepezil, rivastigmine, tacrine, galantamine, memantine; tacrine); NMDA receptor antagonists (e.g., memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocycline or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antipsychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies for the treatment of a disease or disorder disclosed herein.

Combination therapy includes co-administration of a compound of the invention and one or more other agent, sequential administration of a compound of the invention and one or more other agent, administration of a composition containing a compound of the invention and one or more other agent, or simultaneous administration of separate compositions containing a compound of the invention and one or more other agent.

E. Exemplary Synthesis

General Description of Synthetic Methods

The compounds of the present invention can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. In these reactions, it is also possible to make use of variants which are themselves known to those of ordinary skill in this art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below X, $R^1$, $R^2$, $R^3$ and $R^4$ have the meanings indicated above unless otherwise indicated. The abbreviations used in these experimental details are listed below and additional ones should be known to a person skilled in the art of synthesis. In addition one can refer to the following references for suitable methods of synthesis as described in March, *Advanced Organic Chemistry*, 3rd edition, John Wiley & Sons, 1985, Greene and Wuts, *Protective Groups in Organic Synthesis*, $2^{nd}$ edition, John Wiley & Sons, 1991, and Richard Larock, *Comprehensive Organic Transformations*, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

LC-MS data were obtained by utilizing one or more of the following chromatographic conditions:

Method 1 (10-80, 2 min)

| Column | Xtimate ™ C18 2.1*30 mm, 3 µm |
|---|---|
| Mobile Phase | A: water (4 L) + TFA (1.5 mL) |
| | B: acetonitrile (4 L) + TFA (0.75 mL) |

| TIME(min) | A % | B % |
|---|---|---|
| 0 | 90 | 10 |
| 0.9 | 20 | 80 |
| 1.5 | 20 | 80 |
| 1.51 | 90 | 10 |
| 2 | 90 | 10 |

| Flow Rate | 1.2 mL/min |
|---|---|
| wavelength | UV 220 nm |
| Oven Temp | 50° C. |
| MS ionization | ESI |

Method 2 (30-90, 2 min)

| Column | Xtimate ™ C18 2.1*30 mm, 3 µm |
|---|---|
| Mobile Phase | A: water (4 L) + TFA (1.5 mL) |
| | B: acetonitrile (4 L) + TFA (0.75 mL) |

| TIME(min) | A % | B % |
|---|---|---|
| 0 | 70 | 30 |
| 0.9 | 10 | 90 |
| 1.5 | 10 | 90 |
| 1.51 | 70 | 30 |
| 2 | 70 | 30 |

| Flow Rate | 1.2 mL/min |
|---|---|
| wavelength | UV 220 nm |
| Oven Temp | 50° C. |
| MS ionization | ESI |

Method 3 (0-60, 2 min)

| Column | Xtimate ™ C18 2.1*30 mm, 3 μm |
|---|---|
| Mobile Phase | A: water (4 L) + TFA (1.5 mL) |
| | B: acetonitrile (4 L) + TFA (0.75 mL) |

| TIME(min) | A % | B % |
|---|---|---|
| 0 | 100 | 0 |
| 0.9 | 40 | 60 |
| 1.5 | 40 | 60 |
| 1.51 | 100 | 0 |
| 2 | 100 | 0 |

| Flow Rate | 1.2 mL/min |
|---|---|
| wavelength | UV 220 nm |
| Oven Temp | 50° C. |
| MS ionization | ESI |

Method 4:

HPLC System: Waters ACQUITY; Column: Waters ACQUITY CSH™ C18 1.7 μM

Guard column: Waters Assy. Frit, 0.2 μM, 2.1 mm; Column tem: 40° C.

Mobile Phase: A: TFA: Water (1:1000, v:v) Mobile phase B: TFA:ACN (1:1000, v:v); Flow Rate: 0.65 mL/min; Injection Volume: 2 μL; Acquisition time: approximately 1.5 minute.

Gradient Program:

| Time (min) | B % |
|---|---|
| 0 | 10 |
| 0.8 | 90 |
| 1.20 | 90 |
| 1.21 | 10 |

Mass Spectrometer Parameters

Mass Spectrometer: Waters SQD; Ionization: Positive Electrospray Ionization (ESI); Mode Scan (100-1400 m/z in every 0.2 second); ES Capillary Voltage: 3.5 kv; ES Cone Voltage: 25 v Source Temperature: 120° C.; Desolvation Temperature: 500° C.; Desolvation Gas Flow: Nitrogen Setting 650 (L/hr); Cone Gas Flow: Nitrogen Setting 50 (L/hr).

SFC separation of compounds of the invention were carried out under the following methods.

Method A:

Instrument: Thar SFC 80; Column: AD 250 mm*30 mm, 5 μm; Mobile phase: A: Supercritical $CO_2$, B: IPA (0.05% DEA), A: B=80:20 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

Method B:

Instrument: SFC MG2; Column: OJ 250 mm*30 mm, 5 μm; Mobile phase: A: Supercritical $CO_2$, B: MeOH (0.05% DEA), A:B=90:10 at 70 ml/min; Column Temp: 38° C.; Nozzle Pressure: 100 Bar Nozzle Temp: 60° C.; Evaporator Temp: 20° C.; Trimmer Temp: 25° C.; Wavelength: 220 nm.

The chiral purity of compounds of the invention was determined by analytical chiral HPLC, which was carried out using Chiralcel® or Chiralpak® columns, using $CO_2$, together with from 5% to 40% methanol, ethanol or isopropanol, containing 0.05% DEA as eluents.

Analytical Chiral HPLC

| Method | Detailed information |
|---|---|
| OJ-H_3_5_40_2.35ML | Column: Chiralcel ® OJ-H 250 × 4.6 mm I.D., 5 μm Mobile phase: methanol (0.05% DEA) in $CO_2$ from 5% to 40% Flow rate: 2.35 mL/min Wavelength: 220 nm |
| OJ-H_3_5_40_2.5ML | Column: Chiralcel ® OJ-H 250 × 4.6 mm I.D., 5 μm Mobile phase: methanol (0.05% DEA) in $CO_2$ from 5% to 40% Flow rate: 2.5 mL/min Wavelength: 220 nm |
| AS-H_3_5_40_2.35ML | Column: Chiralpak ® AS-H 250 × 4.6 mm I.D., 5 μm Mobile phase: methanol (0.05% DEA) in $CO_2$ from 5% to 40% Flow rate: 2.35 mL/min Wavelength: 220 nm |
| AS-H_4_5_40_2.5ML | Column: Chiralpak ® AS-H 250 × 4.6 mm I.D., 5 μm Mobile phase: iso-propanol (0.05% DEA) in CO2 from 5% to 40% Flow rate: 2.5 mL/min Wavelength: 220 nm |
| AS-H_5_5_40_2.35ML | Column: Chiralpak ® AS-H 250 × 4.6 mm I.D., 5 μm Mobile phase: ethanol (0.05% DEA) in $CO_2$ from 5% to 40% Flow rate: 2.35 mL/min Wavelength: 220 nm |
| AS-H_3_5_40_2.5ML | Column: Chiralpak ® AS-H 250 × 4.6 mm I.D., 5 μm Mobile phase: methanol (0.05% DEA) in CO2 from 5% to 40% Flow rate: 2.5 mL/min Wavelength: 220 nm |
| AD-H_3_5_40_2.35ML | Column: Chiralpak ® AD-H 250 × 4.6 mm I.D., 5 μm Mobile phase: methanol (0.05% DEA) in $CO_2$ from 5% to 40% Flow rate: 2.35 mL/min Wavelength: 220 nm |
| AD-H_5_5_40_2.35ML | Column: Chiralpak ® AD-H 250 × 4.6 mm I.D., 5 μm Mobile phase: ethanol (0.05% DEA) in $CO_2$ from 5% to 40% Flow rate: 2.35 mL/min Wavelength: 220 nm |
| OD-3_3_5_40_2.5ML | Column: Chiralcel ® OD-3 150 × 4.6 mm I.D., 3 μm Mobile phase: methanol (0.05% DEA) in $CO_2$ from 5% to 40% Flow rate: 2.5 mL/min Wavelength: 220 nm |
| OD-3_4_5_40_2.5ML | Column: Chiralcel ® OD-3 150 × 4.6 mm I.D., 3 μm Mobile phase: iso-propanol (0.05% DEA) in $CO_2$ from 5% to 40% Flow rate: 2.5 mL/min Wavelength: 220 nm |
| OD-3_5_5_40_2.5ML | Column: Chiralcel ® OD-3 150 × 4.6 mm I.D., 3 μm Mobile phase: ethanol (0.05% DEA) in $CO_2$ from 5% to 40% Flow rate: 2.5 mL/min Wavelength: 220 nm |

-continued

| Method | Detailed information |
|---|---|
| AD-3_3_5_40_2.5ML | Column: Chiralpak ® AD-3 150 × 4.6 mm I.D., 3 μm Mobile phase: methanol (0.05% DEA) in $CO_2$ from 5% to 40% Flow rate: 2.5 mL/min Wavelength: 220 nm |
| AD-3_4_5_40_2.5ML | Column: Chiralpak ® AD-3 150 × 4.6 mm I.D., 3 μm Mobile phase: iso-propanol (0.05% DEA) in $CO_2$ from 5% to 40% Flow rate: 2.5 mL/min Wavelength: 220 nm |
| AD-3_5_5_40_2.5ML | Column: Chiralpak ® AD-3 150 × 4.6 mm I.D., 3 μm Mobile phase: ethanol (0.05% DEA) in $CO_2$ from 5% to 40% Flow rate: 2.5 mL/min Wavelength: 220 nm |
| OD-H_3_5_40_2.35ML | Column: Chiralcel ® OD-H 250 × 4.6 mm I.D., 5 μm Mobile phase: methanol (0.05% DEA) in $CO_2$ from 5% to 40% Flow rate: 2.35 mL/min Wavelength: 220 nm |
| OD-H_5_5_40_2.35ML | Column: Chiralcel ® OD-H 250 × 4.6 mm I.D., 5 μm Mobile phase: ethanol (0.05% DEA) in $CO_2$ from 5% to 40% Flow rate: 2.35 mL/min Wavelength: 220 nm |

The invention is illustrated by way of the following examples, in which the following abbreviations may be employed:

| Abbreviation | Meaning |
|---|---|
| ACN, MeCN, $CH_3CN$ | acetonitrile |
| Aq | aqueous |
| Boc | tert-butoxy carbonyl or t-butoxy carbonyl |
| brine | saturated aqueous NaCl |
| Cbz | benzyloxy carbonyl |
| $CeCl_3$ | ceric chloride |
| $Cs_2CO_3$ | cesium carbonate |
| CuI | cuprous iodide |
| DCM or $CH_2Cl_2$ | methylene chloride |
| DIEA | diisopropyl ethyl amine |
| DMF | dimethyl formamide |
| DMS/Me2S | dimethyl sulfide |
| DMSO | dimethyl sulfoxide |
| EDCI | 1-(3-dimethylaminopropyl)-3-ethylcarbodiiimide hydrochloride |
| EtI | ethyl iodide |
| Et | ethyl |
| $Et_2O$ | ethyl ether |
| $Et_3SiH$ | triethylsilane |
| $Et_3N$ | triethylamine |
| EtOAc, EA, AcOEt | ethyl acetate |
| EtOH | ethanol |
| $FeCl_3$ | ferric chloride |
| h, hr | hour(s) |
| HATU | O-(7-azabenzotriazol-1-yl)-N,N,N',N'-tetramethyluronium-hexafluorophosphate |
| HBTU | O-Benzotriazole-1-yl-N,N,N',N'-tetramethyluronium-hexafluorophosphate |
| HCl | hydrochloric acid |
| $H_2O$ | water |
| $H_2O_2$ | hydrogen peroxide |
| HPLC | high performance liquid chromatography |
| i-BuOCOCl | iso-butoxycarbonyl chloride |
| ICl | iodochloride |
| $K_2CO_3$ | potassium carbonate |
| $K_3PO_4$ | tripotassium phosphate |
| LC-MS | liquid chromatography-mass spectrometry |
| LDA | lithium diisopropylamide |
| LiCl | lithium chloride |
| LiOH | lithium hydroxide |
| MCPBA, m-CPBA | meta-chloroperoxybenzoic acid |
| MeOH | methanol |
| MeI | methyl iodide |
| Me | methyl |
| mg | milligram |
| $Mg_2SO_4$ | magnesium sulfate (anhydrous) |
| min | minute(s) |
| mL | milliliters |
| mmol | millimoles |
| mp, m.p. | melting point |
| MS | mass spectrometry |
| MW | microwave |
| $NaBH_4$ | sodium borohydride |
| $NaBH_3CN$ | sodium cyanoborohydride |
| NaH | sodium hydride |
| $NaHCO_3$ | sodium bicarbonate |
| NaOH | sodium hydroxide |
| NaOMe | sodium methoxide |
| $Na_2S_2O_3$ | sodium thiosulfate |
| $Na_2S_2O_5$ | sodium dithionate |
| $Na_2SO_4$ | sodium sulfate |
| $NH_4OH$ | ammonium hydroxide |
| $(NH_4)_2CO_3$ | ammonium carbonate |
| $NH_4Cl$ | ammonium chloride |
| $Na_2CO_3$ | sodium carbonate |
| $NaHCO_3$ | sodium bicarbonate |
| NaH | sodium hydride |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| $PdCl_2dppf$ | [1,1-bis(diphenylphosphino)ferrocene]dichloropalladium(ii) |
| $Pd_2(dba)_3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| $Ti(OEt)_4$ | titanium tetra ethoxide |
| Zn | zinc |
| $Zn(CN)_2$ | zinc cyanide |

In the first process, a compound of Formula I can be prepared by $S_NAr$ or palladium catalyzed reactions of reagents of 1, where $G^1$ is Cl, Br, I, OTf or OTs, with intermediates of Formula 2. Reagents 1 are either commercially available or can be prepared readily from commercially available precursors based on literature precedents.

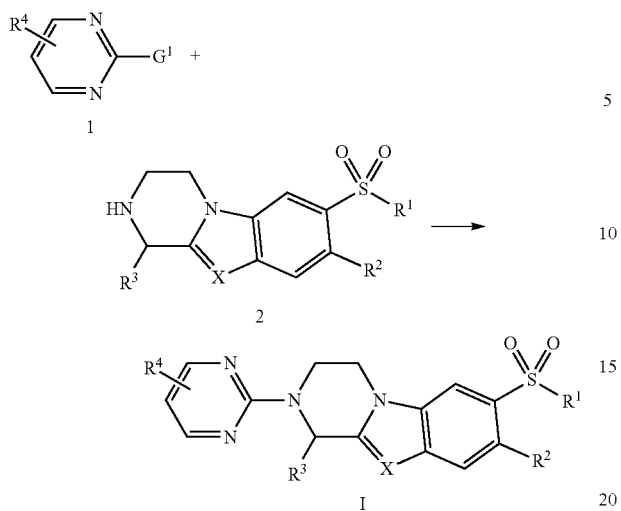

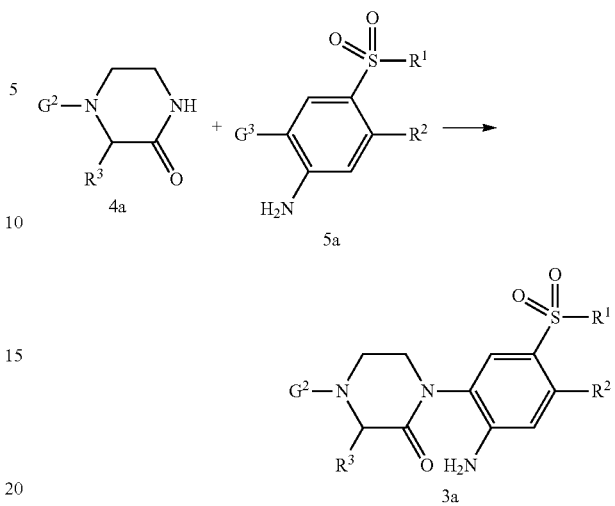

Intermediates 2 can be prepared by one of the several different methods depicted below.

When X=N, intermediates of Formula 2 can be prepared by cyclization of intermediates of Formula 3a followed by removal of $G^2$ when $G^2$ is not hydrogen. $G^2$ is an amine protecting group, such as Boc, Cbz and trifluoroacetamide, etc.

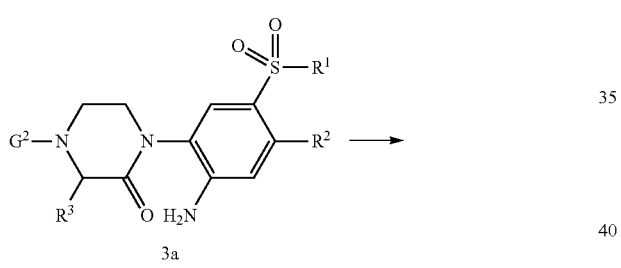

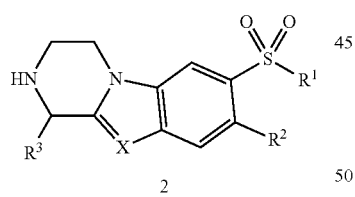

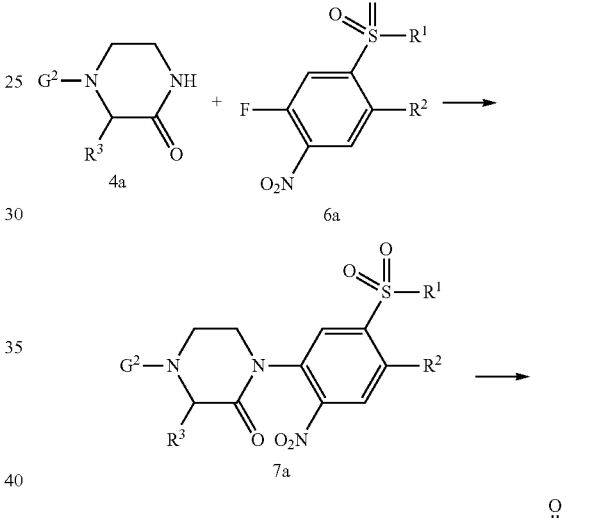

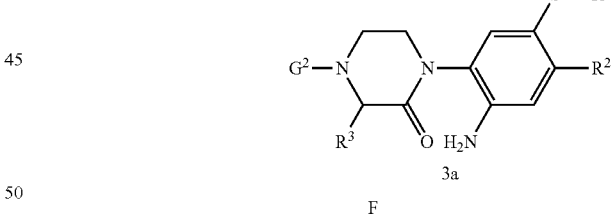

Intermediates of Formula 3a can be prepared by one of the two methods: 1) copper mediated coupling of piperazinone 4a and aniline 5a, where $G^3$ is Br, I, Cl or OTf; 2) $S_NAr$ reaction between 4a and fluorinated nitrobenzene 6a to give intermediate of Formula 7a followed by reduction of the nitro group. The intermediate 7a can also be prepared from an intermediate of Formula 8a by displacement of fluorine with either sodium alkanesulfinate ($R^1SO_2Na$) or sodium alkylsulfide ($R^1SNa$) followed by oxidation of the resulting thioether. The intermediate 8a in turn can be prepared from piperazinone 4a and difluoro nitrobenzene 9a, which are either commercially available or can be readily prepared from commercial precursors based on literature procedures, well known to those of ordinary skill in the art.

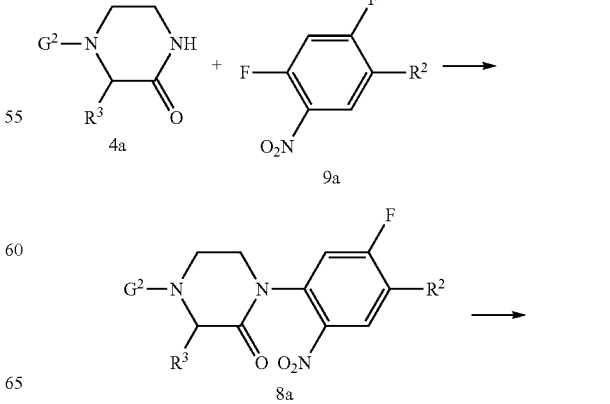

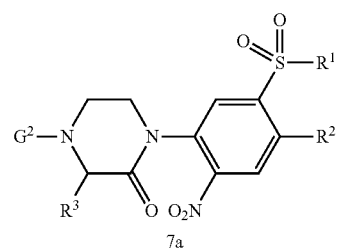

For example, when R³=isopropyl, piperazinone 4a can be prepared by one of the methods presented below.

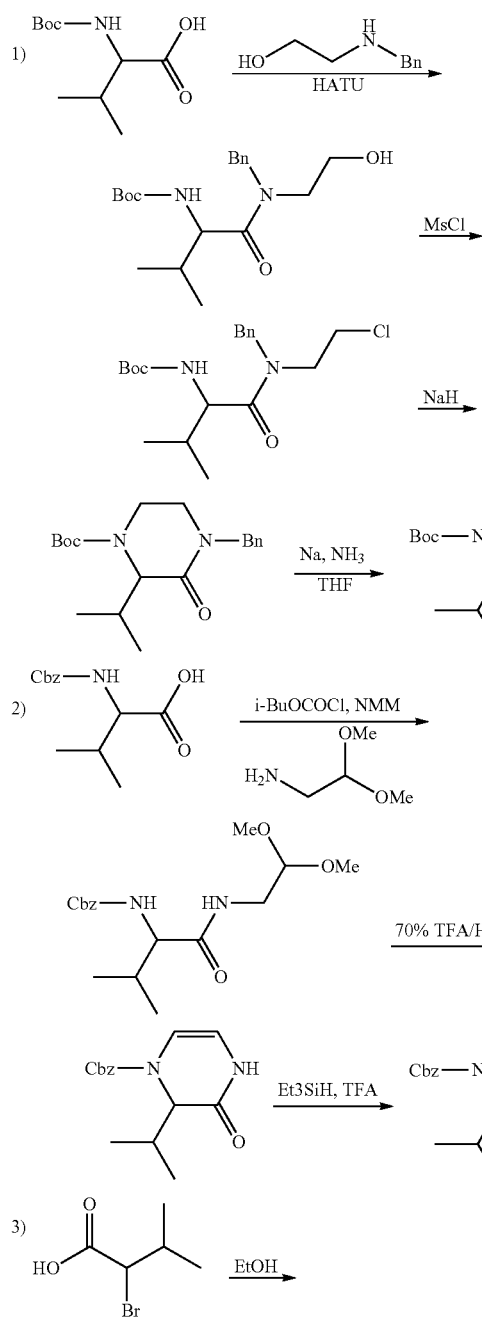

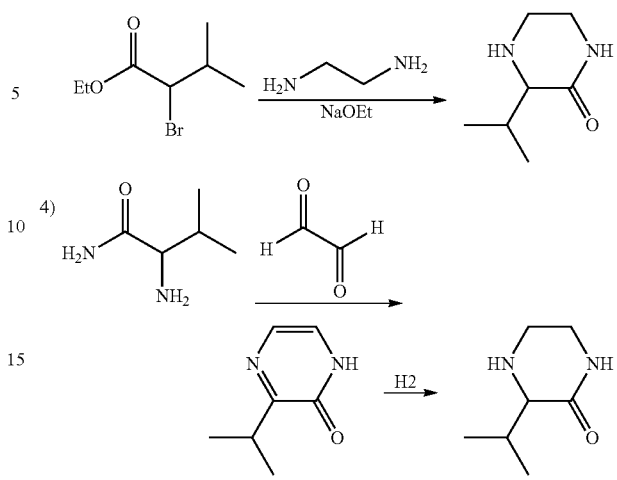

When X=CH, intermediates of Formula 2 can be prepared from intermediates of Formula 3b by deprotection of G² followed by reductive amination. G² are amine protecting groups, such as Boc, Cbz and trifluoroacetamide etc.

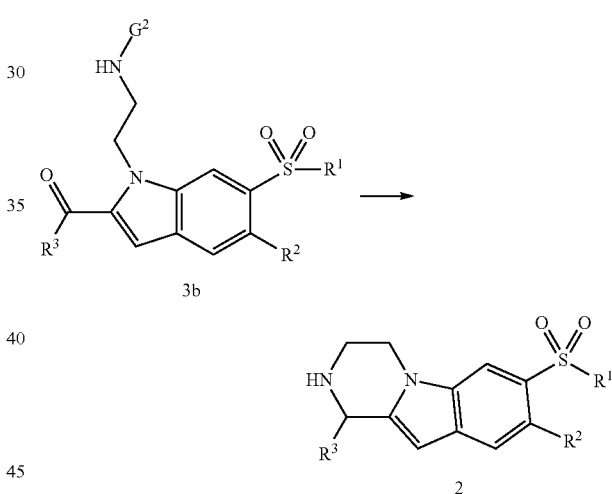

Intermediates of Formula 3b can be prepared by N-alkylation of indole 4b with commercially available alkyl halide 5b, where G³ is Br or I. Intermediates of Formula 4b can be prepared by removal of G⁴ from intermediates of Formula 6b, where G⁴ is methanesulfonate or phenylsulfonate.

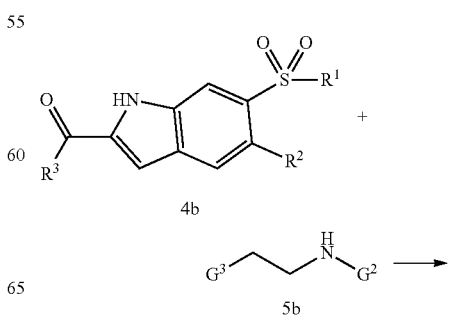

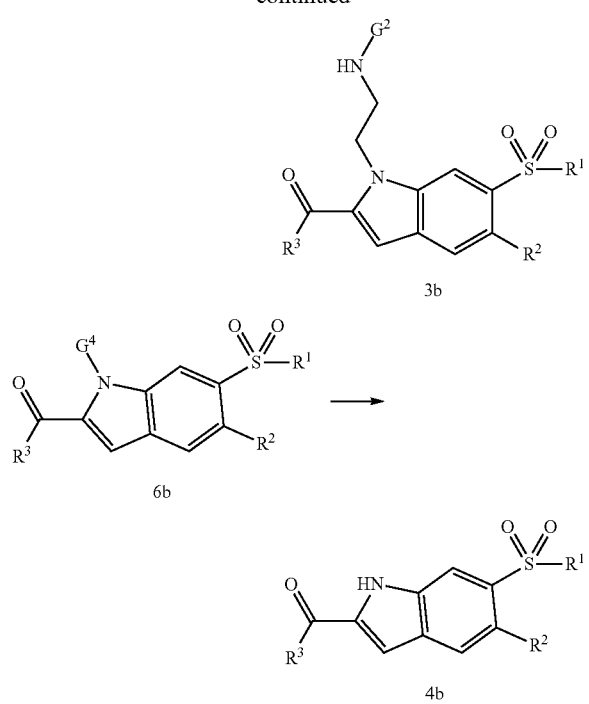

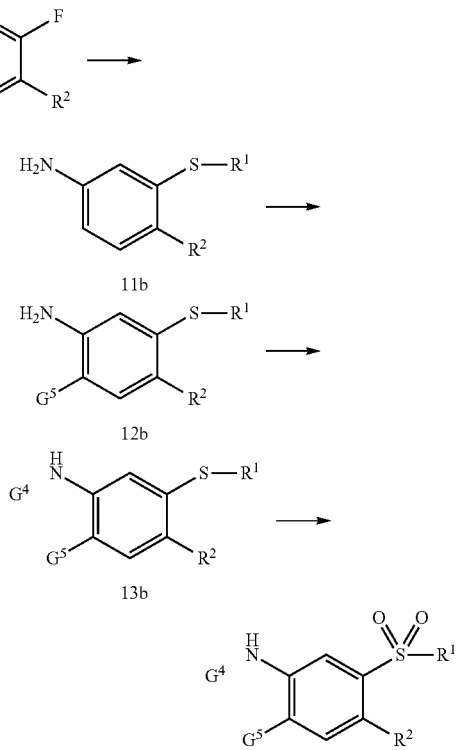

Intermediates of Formula 6b can be prepared by sequential Sonogashira coupling reaction between aryl halides 7b (where G⁵ is Br or I) and propargyl alcohols 8b, followed by cyclization, to give intermediates of Formula 9b, followed by oxidation of the alcohol.

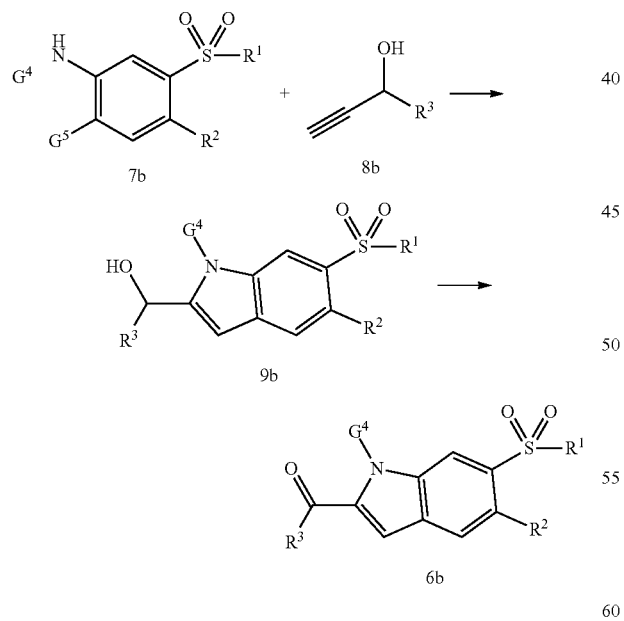

Intermediates of Formula 7b can be prepared from commercially available aniline 10b via the following transformations: 1) Displacement of fluorine with sodium alkyl sulfide $R^1SNa$ (yielding 11b); 2) Halogenation (yielding 12b); 3) Protection of aniline (yielding 13b); 4) Oxidation of sulfide (yielding 7b).

In the second process, a compound of Formula I, where $R^1$=alkyl, $R^2$=H and X=CH, can be prepared by oxidation of the thioether group in intermediates of Formula 1c. Intermediate 1c in turn can be prepared from coupling of reagents 1 and intermediates of Formula 2c via $S_NAr$ or palladium catalyzed reactions.

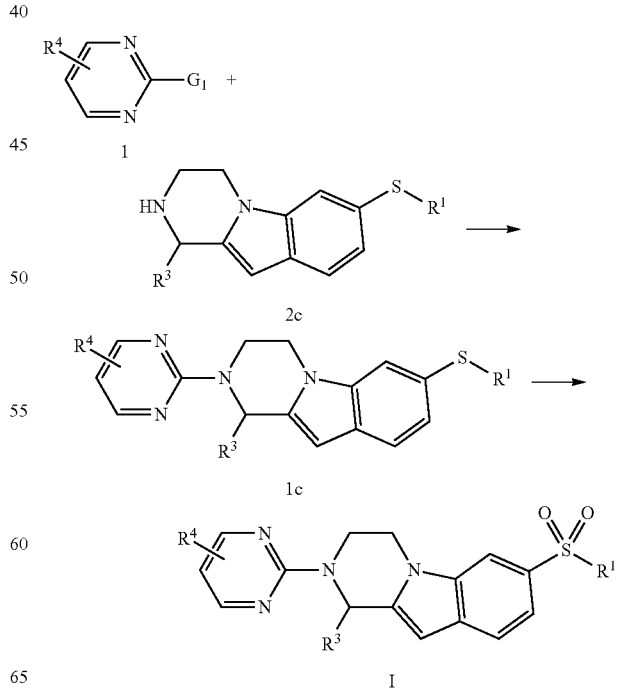

Intermediates 2c can be prepared according to following scheme.

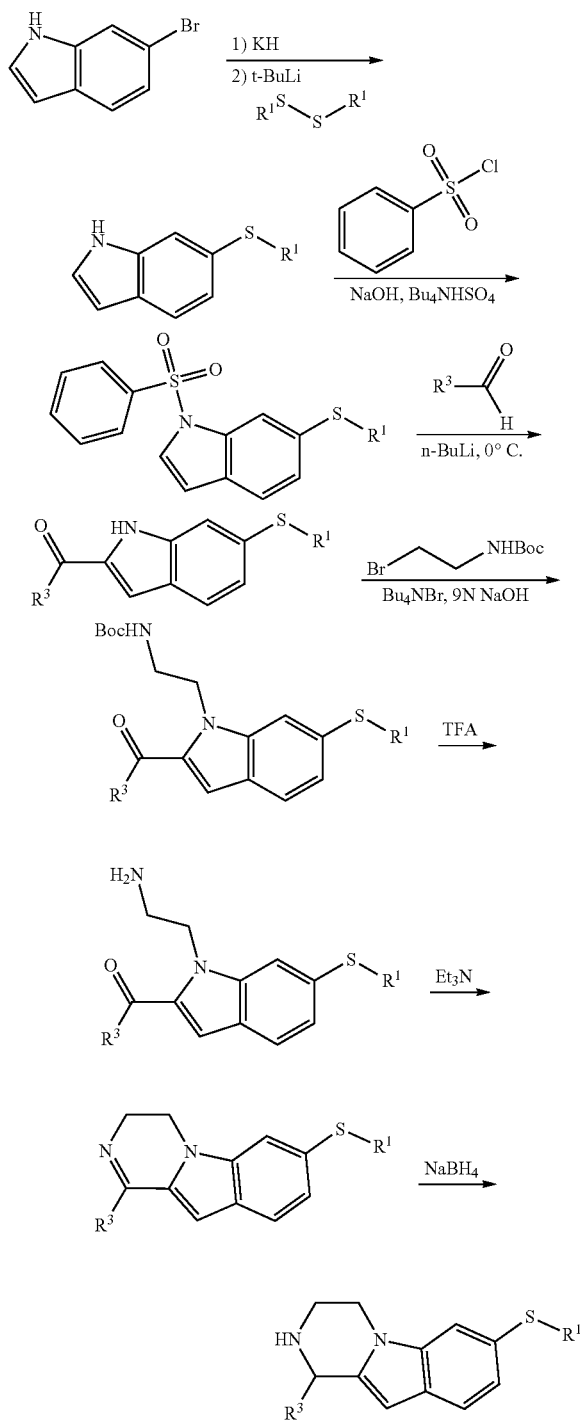

All patents, patent applications, books and literature cited in the specification are hereby incorporated by reference in their entirety. In the case of any inconsistencies, the present disclosure, including any definitions therein will prevail.

The invention will be further described by reference to the following detailed examples, which are given for illustration of the invention, and are not intended to be limiting thereof.

EXAMPLE 1

1-isopropyl-7-(methylsulfonyl)-2-(4-(trifluoromethyl)pyrimidin-2-yl)-1,2,3,4-tetrahydrobenzo[4,5]imidazo[1,2-a]pyrazine

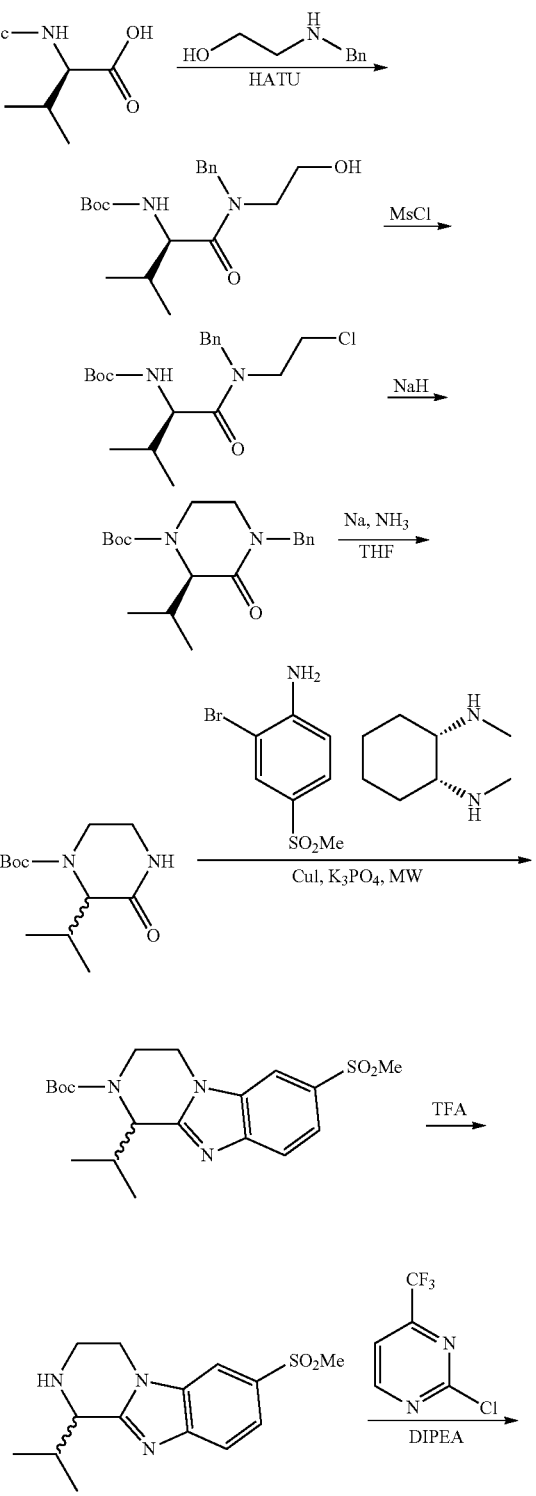

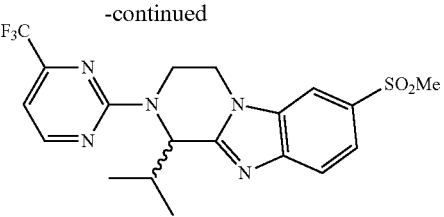

Racemization occurred during the course of synthesis

Step 1:

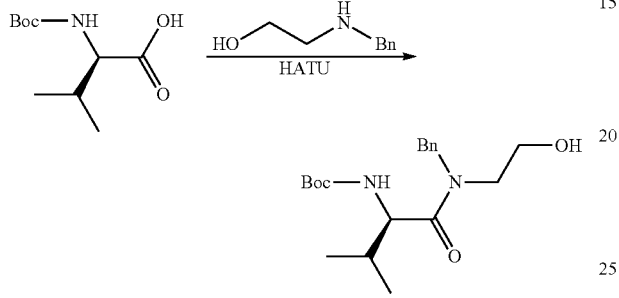

To a solution of (R)-2-((tert-butoxycarbonyl)amino)-3-methylbutanoic acid (2.0 g, 9.20 mmol) in CH$_2$Cl$_2$ (40 mL) were added 2-(benzylamino)ethanol (1.3 g, 8.80 mmol), HATU (5.30 g, 13.8 mmol) and Et$_3$N (2.80 g, 27.6 mmol) under N$_2$. The mixture was stirred at rt overnight. The mixture was added water (20 mL) and extracted with EtOAc (3×30 mL). The combined organic layers were washed with brine (20 mL), dried over anhydrous Na$_2$SO$_4$, filtered, concentrated and then purified by column chromatography on silica gel to afford (R)-tert-butyl (1-(benzyl(2-hydroxyethyl)amino)-3-methyl-1-oxobutan-2-yl)carbamate (2.80 g, 88% yield) as a white solid. LC-MS m/z 351.2 [M+H]$^+$.

Step 2:

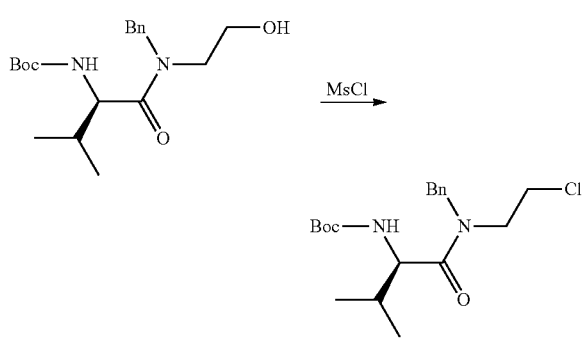

To a solution of (R)-tert-butyl (1-(benzyl(2-hydroxyethyl)amino)-3-methyl-1-oxobutan-2-yl)carbamate (2.80 g, 8.0 mmol) in CH$_2$Cl$_2$ (20 mL) was added Et$_3$N (1.60 g, 16 mmol) and MsCl (1.40 g, 12.0 mmol) dropwise at −10° C. under N$_2$. The mixture was stirred at rt overnight. The mixture was quenched with water (20 mL) and extracted with CH$_2$Cl$_2$ (3×20 mL). The combined organic layers were washed with brine (20 mL) and dried over anhydrous Na$_2$SO$_4$, filtered, concentrated to afford (R)-tert-butyl (1-(benzyl(2-chloroethyl)amino)-3-methyl-1-oxobutan-2-yl)carbamate (3.0 g, 100% yield) as a yellow solid, which was used for the next step without further purification. LC-MS m/z 369.2 [M+H]$^+$. $^1$H NMR (CDCl$_3$ 400 MHz): δ 7.37-7.28 (m, 3H), 7.22-7.20 (m, 2H), 5.27-5.18 (m, 1H), 4.93-4.86 (m, 1H), 4.64-4.39 (m, 2H), 3.85-3.66 (m, 2H), 3.61-3.39 (m, 2H), 2.03-1.97 (m, 1H), 1.45 (s, 9H), 0.98 (d, J=6.8 Hz, 3H), 0.93 (d, J=6.8 Hz, 3H).

Step 3:

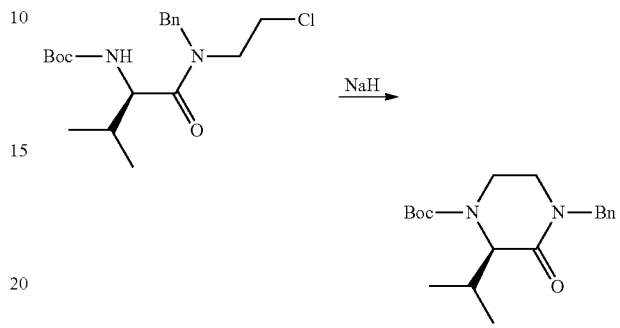

To a solution of (R)-tert-butyl (1-(benzyl(2-chloroethyl)amino)-3-methyl-1-oxobutan-2-yl)carbamate (2.0 g, 5.40 mmol) in DMF (30 mL) was added NaH (1.0 g, 27.0 mmol, 60% in mineral oil) at 0° C. under N$_2$. The mixture was stirred at rt for 2 h. The mixture was quenched with water (20 mL) and extracted with EtOAc (3×20 mL). The combined organic layers were washed with brine (20 mL) and dried over anhydrous Na$_2$SO$_4$, filtered, concentrated and purified by column chromatography to afford (R)-tert-butyl 4-benzyl-2-isopropyl-3-oxopiperazine-1-carboxylate (1.13 g, 63% yield) as a white solid. LC-MS m/z 277.1 [M-56+H]$^+$. $^1$H NMR (CDCl$_3$ 400 MHz): δ 7.38-7.29 (m, 3H), 7.29-7.22 (m, 2H), 5.02-4.86 (m, 1H), 4.49-4.39 (m, 1H), 4.31-4.06 (m, 2H), 3.41-3.18 (m, 3H), 2.42-2.31 (m, 1H), 1.46 (s, 9H), 1.12 (d, J=6.8 Hz, 3H), 1.00 (d, J=6.8 Hz, 3H).

Step 4:

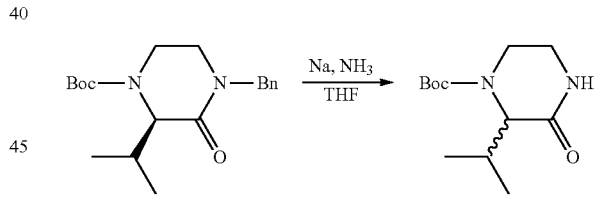

To a three-necked bottle containing THF (10 mL) was bubbled with NH$_3$ (gas) at −78° C. for 5 mins. Then Na (300 mg, 13.0 mmol) was added to the mixture slowly at −78° C. After stirring for 30 min, (R)-tert-butyl 4-benzyl-2-isopropyl-3-oxopiperazine-1-carboxylate (700 mg, 2.11 mmol) was added dropwise at −78° C. The mixture was stirred at −78° C. for 30 min The mixture was quenched with sat. aq. NH$_4$Cl (10 mL) and extracted with EtOAc (3×10 mL). The combined organic layers were washed with brine (10 mL), dried over anhydrous Na$_2$SO$_4$, filtered, concentrated and purified by preparative TLC with petroleum ether/EtOAc 1/1 to afford tert-butyl 2-isopropyl-3-oxopiperazine-1-carboxylate (300 mg, 59% yield) as a white solid. The product was found to be a racemic mixture. The cause of racemization was not investigated. LC-MS m/z 187.1 [M-56+H]$^+$, 265.1 [M+Na]$^+$. $^1$H NMR (CDCl$_3$ 400 MHz): δ 6.29 (s, 1H), 4.55-3.99 (m, 2H), 3.51-3.36 (m, 1H), 3.32-3.12 (m, 2H), 2.34-2.29 (m, 1H), 1.46 (s, 9H), 1.09 (d, J=6.8 Hz, 3H), 0.99 (d, J=7.2 Hz, 3H).

Step 5:

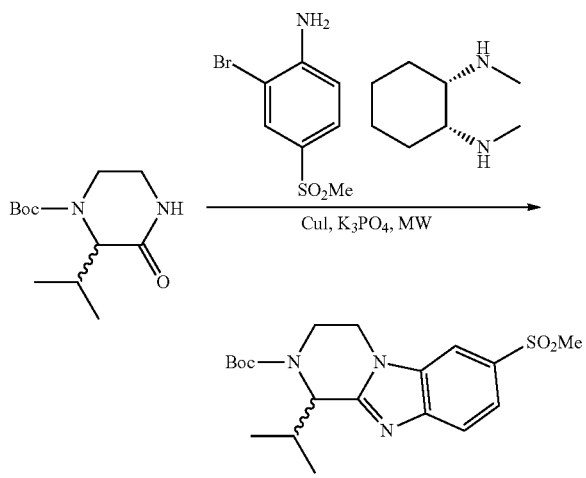

To a solution of tert-butyl 2-isopropyl-3-oxopiperazine-1-carboxylate (200 mg, 0.83 mmol) in NMP (3 mL) were added 2-bromo-4-(methylsulfonyl)aniline (207 mg, 0.83 mmol), (1R,2S)—N1,N2-dimethylcyclohexane-1,2-diamine (12.0 mg, 0.08 mmol), $K_3PO_4 \cdot 3H_2O$ (660 mg, 2.48 mmol) and CuI (16 mg, 0.08 mmol). The mixture was stirred at 150° C. for 1 h in a microwave oven. The mixture was diluted with water (10 mL) and extracted with EtOAc (3×10 mL). The combined organic layers were washed with brine (10 mL), dried over anhydrous $Na_2SO_4$, filtered, concentrated and purified by preparative TLC with $CH_2Cl_2$/MeOH 35/1 to afford tert-butyl 1-isopropyl-7-(methylsulfonyl)-3,4-dihydrobenzo[4,5]imidazo[1,2-a]pyrazine-2(1H)-carboxylate (110 mg, 34% yield) as a white solid. LC-MS m/z 394.1 [M+H]$^+$. $^1$H NMR (CDCl$_3$ 400 MHz): δ 7.94 (s, 1H), 7.83-7.76 (m, 2H), 5.35-5.17 (m, 1H), 4.73-4.42 (m, 1H), 4.22-4.12 (m, 1H), 4.11-3.99 (m, 1H), 3.53-3.37 (m, 1H), 3.03 (s, 3H), 2.38-2.27 (m, 1H), 1.42 (s, 9H), 1.19 (d, J=6.8 Hz, 3H), 0.97 (d, J=6.8 Hz, 3H).

Step 6:

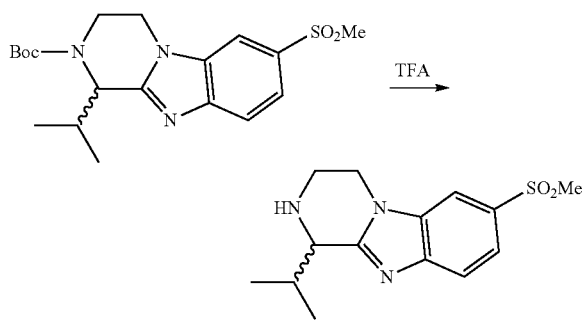

To a solution of tert-butyl 1-isopropyl-7-(methylsulfonyl)-3,4-dihydrobenzo[4,5]imidazo[1,2-a]pyrazine-2(1H)-carboxylate (20 mg, 0.05 mmol) in $CH_2Cl_2$ (1 mL) was added TFA (0.3 mL) under $N_2$. The mixture was stirred at rt for 1 h. The mixture was concentrated to afford 1-isopropyl-7-(methylsulfonyl)-1,2,3,4-tetrahydrobenzo[4,5]imidazo[1,2-a]pyrazine (20 mg, TFA salt, 100% yield) as a yellow solid, which was used for the next step without further purification. LC-MS m/z 352.1 [M+H]$^+$.

Step 7:

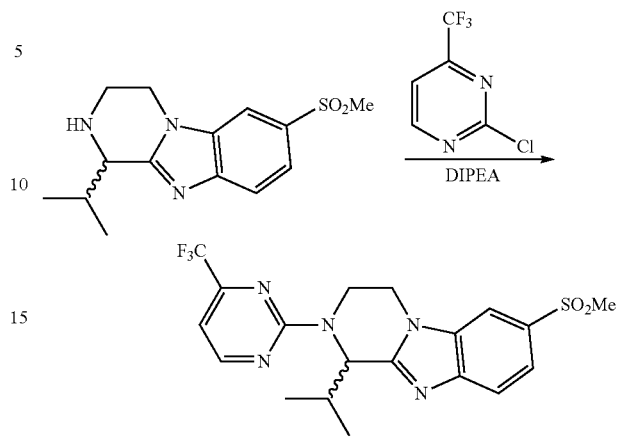

To a solution of 1-isopropyl-7-(methylsulfonyl)-1,2,3,4-tetrahydrobenzo[4,5]imidazo[1,2-a]pyrazine (15 mg, 0.05 mmol) in DMSO (3 mL) was added 2-chloro-4-(trifluoromethyl)pyrimidine (19 mg, 0.10 mmol) and DIEA (20 mg, 0.15 mmol) under $N_2$. The mixture was stirred at 100° C. for 2 h. Water (10 mL) was added and the mixture was extracted with EtOAc (3×10 mL). The combined organic layers were washed with brine (10 mL), dried over anhydrous $Na_2SO_4$, filtered, concentrated and then purified by preparative TLC to afford 1-isopropyl-7-(methylsulfonyl)-2-(4-(trifluoromethyl)pyrimidin-2-yl)-1,2,3,4-tetrahydrobenzo[4,5]imidazo[1,2-a]pyrazine (5.10 mg, 23% yield) as a white solid. LC-MS m/z 440.2 (MH$^+$). $^1$H NMR (CDCl$_3$ 400 MHz): δ 8.58 (d, J=4.8 Hz, 1H), 8.01 (d, J=0.8 Hz, 1H), 7.90-7.81 (m, 2H), 6.89 (d, J=4.8 Hz, 1H), 6.12 (d, J=8.0 Hz, 1H), 5.39 (dd, J=4.0 and 14.0 Hz, 1H), 4.34-4.30 (m, 1H), 4.23-4.16 (m, 1H), 3.83-3.75 (m, 1H), 3.09 (s, 3H), 2.55-2.49 (m, 1H), 1.33 (d, J=6.8 Hz, 3H), 1.09 (d, J=6.8 Hz, 3H).

EXAMPLE 2

(R)-(1-isopropyl-7-(methylsulfonyl)-2-(4-(trifluoromethyl)pyrimidin-2-yl)-1,2,3,4-tetrahydrobenzo[4,5]imidazo[1,2-a]pyrazin-8-yl)methanol and (S)-(1-isopropyl-7-(methylsulfonyl)-2-(4-(trifluoromethyl)pyrimidin-2-yl)-1,2,3,4-tetrahydrobenzo[4,5]imidazo[1,2-a]pyrazin-8-yl)methanol

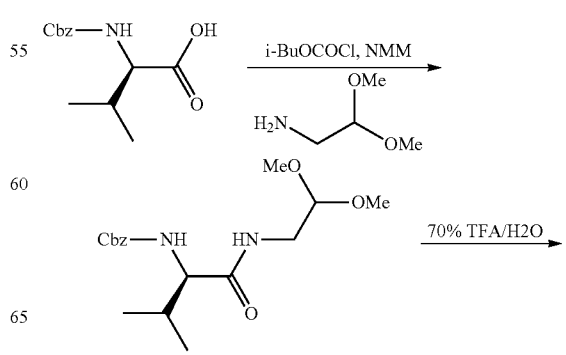

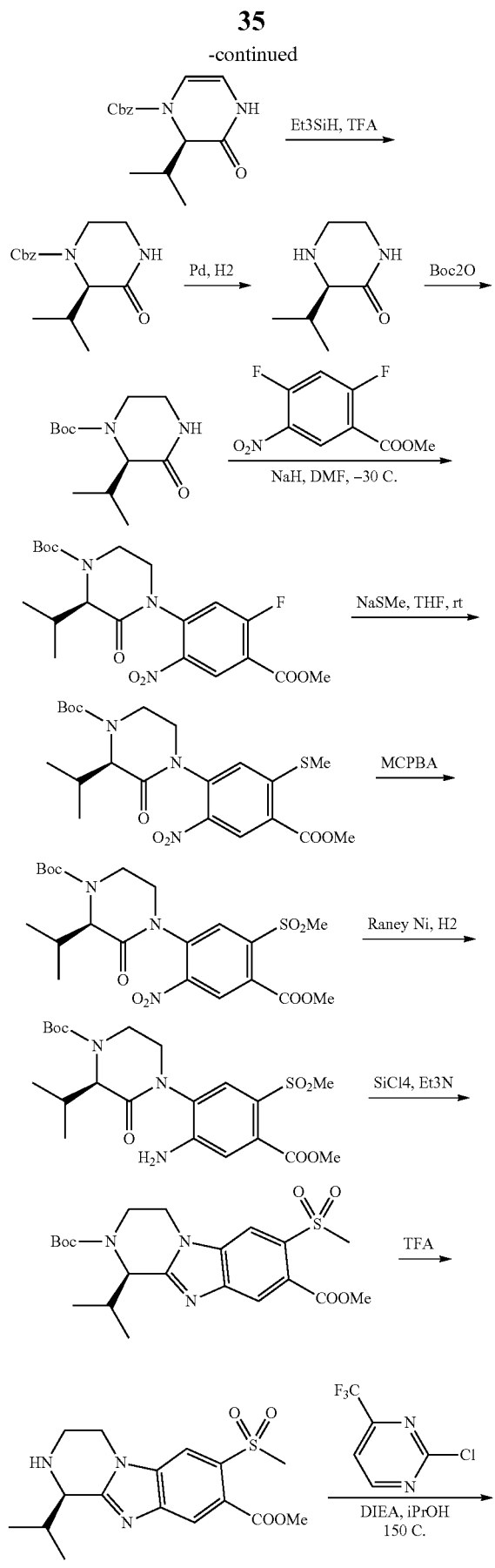

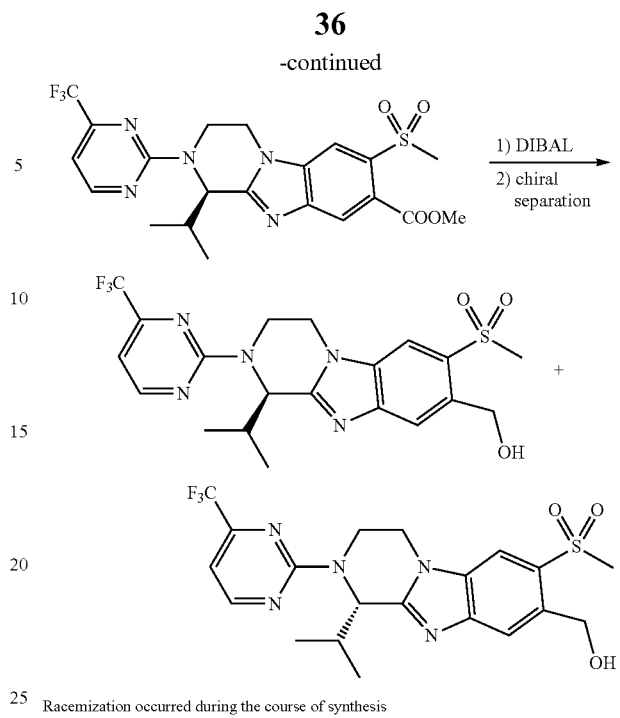

Racemization occurred during the course of synthesis

Step 1:

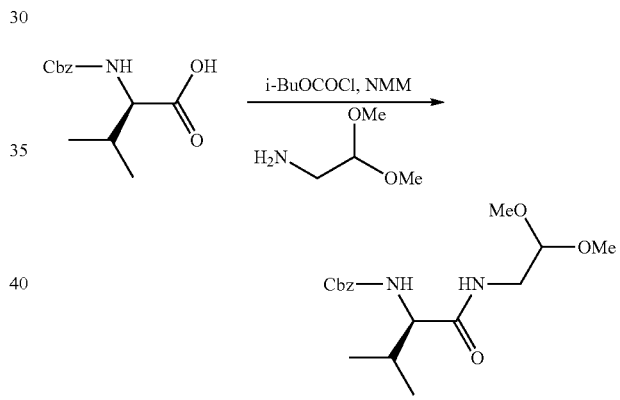

A solution of Cbz-D-Valine (500 g, 1.99 mol) and N-methylmorpholine (201.8 g, 1.99 mol) in anhydrous THF (8 L) was cooled to −15 °C. and i-butyl chloroformate (299 g, 2.19 mol) was added dropwise under stirring. After 30 min, a solution of 1-amino-2,2-dimethoxyethane (209.5 g, 1.99 mol) in THF (1 L) was added slowly and the temperature was maintained at −15 °C. for 2 h. The reaction mixture was washed with brine (2 L) and the organic phase was concentrated to remove the THF. The residue was diluted with EtOAc (4 L), washed with 1N aq HCl (2×2 L), sat. aq. NaHCO$_3$ (2 L) and sat. aq. Na$_2$CO$_3$ (2 L) and brine (1.5 L). After drying over Na$_2$SO$_4$, the organic solvent was removed under reduce pressure to afford (R)-benzyl (1-((2,2-dimethoxyethyl)amino)-3-methyl-1-oxobutan-2-yl)carbamate as a white solid (670 g, yield 99.5%), which was used for next step without further purification. LC-MS m/z 360.9 [M+Na]$^+$.

$^1$H NMR (CD$_3$OD 300 MHz): δ 7.35-7.30 (m, 5H), 5.08 (s, 2H), 4.45-4.35 (m, 1H), 3.95-3.85 (m, 1H), 3.34-3.25 (m, 8H), 2.10-1.90 (m, 1H), 0.94-0.91 (m, 6H).

Step 2:

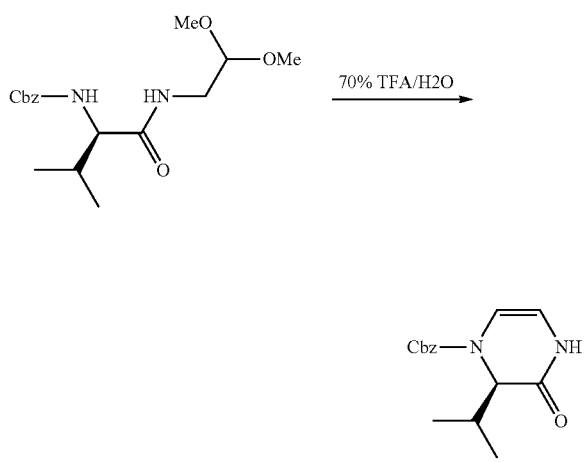

(R)-benzyl (1-((2,2-dimethoxyethyl)amino)-3-methyl-1-oxobutan-2-yl)carbamate (335 g, 0.99 mol) was added in portions to a cooled TFA-H$_2$O (temperature <5° C., V$_{TFA}$/V$_{H2O}$=7/3, 2 L), and the solution was stirred at rt for 12 h. The solution was added slowly into stirring cooled sat. aq. Na$_2$CO$_3$ (2.5 L) to keep the pH >8. The mixture was extracted with EtOAc (5×2 L). The combined organic layers were washed with brine (2 L), dried over anhydrous Na$_2$SO$_4$, filtered and evaporated in vacuo to give (R)-benzyl 2-isopropyl-3-oxo-3,4-dihydropyrazine-1(2H)-carboxylate as a white solid (259 g, 95.4%), which was used for next step without further purification. LC-MS m/z 274.9 [M+H]$^+$. $^1$H NMR (CD$_3$OD 300 MHz): δ 7.36-7.34 (m, 5H), 6.33-6.30 (m, 1H), 5.79-5.68 (m, 1H), 5.26-5.13 (m, 2H), 4.38-4.29 (m, 1H), 2.01-1.96 (m, 1H), 1.00-0.84 (m, 6H).

Step 3:

To a stirring solution of (R)-benzyl 2-isopropyl-3-oxo-3,4-dihydropyrazine-1(2H)-carboxylate (400 g, 1.46 mol) in DCE (2 L) was added Et$_3$SiH (424 g, 3.65 mol) and TFA (665 g, 5.8 mol) at rt. The reaction was stirred under reflux for 36 h. After cooling to rt, the solution was concentrated to remove the solvent. The residue was diluted with EtOAc (2 L), and added slowly into stirring cooled sat. aq. NaHCO$_3$ (2 L) to make sure that the pH>8. The mixture was extracted with EtOAc (2×2.5 L). The combined organic layers were washed with brine, dried over anhydrous Na$_2$SO$_4$, filtered and concentrated to give (R)-benzyl 2-isopropyl-3-oxopiperazine-1-carboxylate (402 g, yield 99.75%), which was used for next step without further purification. LC-MS m/z 276.9 [M+H]$^+$. $^1$H NMR (DMSO-d$_6$ 400 MHz): δ 7.93 (s, 1H), 7.39-7.31 (m, 5H), 5.09 (s, 2H), 4.06-4.01 (m, 1H), 3.99-3.92 (m, 1H), 3.23-3.14 (m, 3H), 2.20-2.12 (m, 1H), 0.96-0.94 (m, 3H), 0.85 (d, J=6.0 Hz, 3H).

Step 4:

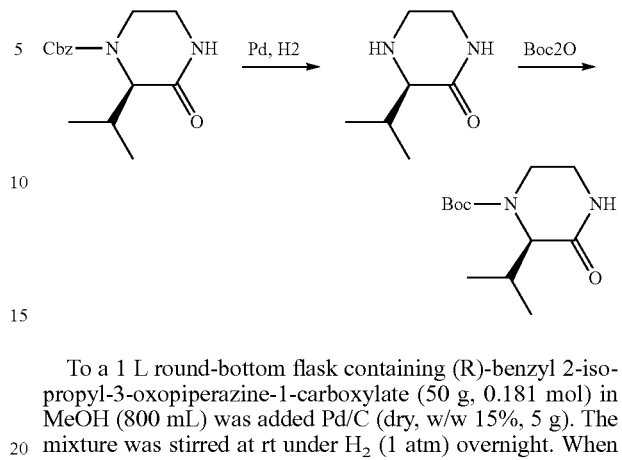

To a 1 L round-bottom flask containing (R)-benzyl 2-isopropyl-3-oxopiperazine-1-carboxylate (50 g, 0.181 mol) in MeOH (800 mL) was added Pd/C (dry, w/w 15%, 5 g). The mixture was stirred at rt under H$_2$ (1 atm) overnight. When TLC and LC-MS showed that the starting material was consumed, (Boc)$_2$O (76.74 g, 0.352 mol) was added to the reaction mixture, and the mixture was stirred at rt overnight until the intermediate (R)-3-isopropylpiperazin-2-one was consumed. The mixture was filtered and concentrated under vacuum. The residue was purified by column chromatography on silica gel (eluting with petroleum:EtOAc=3:1) to give (R)-tert-butyl 2-isopropyl-3-oxopiperazine-1-carboxylate as a white solid (26 g, yield 61%).

For (R)-3-isopropyl-piperazin-2-one:
LC-MS m/z 143.2 [M+H]$^+$. $^1$H NMR (HCl salt, CD$_3$OD 400 MHz): δ 3.95 (d, J=3.6 Hz, 1H), 3.65-3.39 (m, 4H), 2.63-2.54 (m, 1H), 1.15 (d, J=6.8 Hz, 3H), 1.09 (d, J=7.2 Hz, 3H).

For (R)-tert-butyl 2-isopropyl-3-oxopiperazine-1-carboxylate:
LC-MS m/z 186.9 [M-56+H]$^+$. $^1$H NMR (DMSO-d$_6$ 400 MHz): δ 7.93 (s, 1H), 4.02-3.82 (m, 2H), 3.17-3.15 (m, 3H), 2.16 (s, 1H), 1.41 (s, 9H), 0.98 (d, J=6.8 Hz, 3H), 0.89 (d, J=6.4 Hz, 3H).

Step 5:

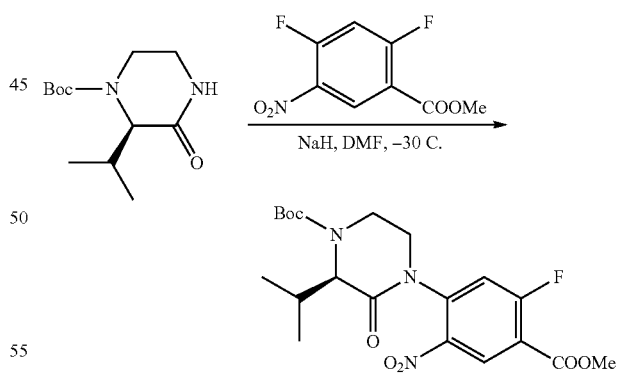

Under N$_2$ atmosphere, NaH (8.8 g, 0.22 mol, 60% in mineral oil, 1.1 eq.) was added in portions at −10° C. to a 1 L three-neck flask containing (R)-tert-butyl 2-isopropyl-3-oxopiperazine-1-carboxylate (26.66 g, 0.11 mol) in DMF (300 mL). The mixture was stirred at −10° C. for 30 min. Then the mixture was added dropwise to a 1 L three-neck flask containing methyl 2,4-difluoro-5-nitrobenzoate (26.3 g, 0.121 mol, 1.1 eq.) in DMF (200 mL) at −20° C. over 10 min After addition, the resulting mixture was stirred between −20° C. and −30° C. for another 10 min. The reaction was quenched with sat. aq. NH₄Cl (200 mL) and then water (800 mL). The aqueous layer was extracted with EtOAc (3×1 L). The combined organic layers were washed with water (3×1 L) and brine, and dried over anhydrous Na₂SO₄. The mixture was filtered and the filtrate was evaporated under vacuum. The residue was purified by column chromatography on silica gel eluting with petroleum ether:EtOAc 8:1~4:1 to give (R)-tert-butyl 4-(5-fluoro-4-(methoxycarbonyl)-2-nitrophenyl)-2-isopropyl-3-oxopiperazine-1-carboxylate (32 g, 66.3% yield) as a yellow solid. LC-MS MS (ESI) m/z 384.1 [M-56+H]⁺, 462.1[M+Na]⁺. ¹H NMR (CDCl₃ 300 MHz): δ 8.63 (d, J=6.9 Hz, 1H), 7.16 (d, J=10.2 Hz, 1H), 4.61-4.30 (m, 2H), 3.97-3.89 (m, 4H), 3.62-3.48 (m, 2H), 2.40-2.34 (m, 1H), 1.49 (s, 9H), 1.08 (d, J=6.9 Hz, 3H), 1.01 (d, J=6.9 Hz, 3H).

Step 6:

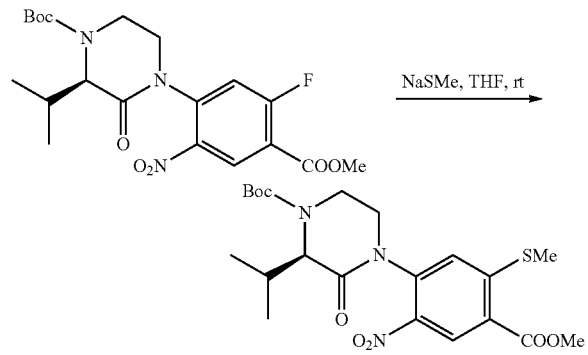

To a 1 L round-bottom flask containing (R)-tert-butyl 4-(5-fluoro-4-(methoxycarbonyl)-2-nitrophenyl)-2-isopropyl-3-oxopiperazine-1-carboxylate was added NaSMe (14.3 g, 0.204 mmol, 3 eq.). The mixture was stirred at rt for 1 h. Water (500 mL) was added and the mixture was concentrated under vacuum to remove THF. The aqueous layer was extracted with EtOAc (3×800 mL). The combined organic layers were washed with brine, dried over anhydrous Na₂SO₄, filtered and concentrated under vacuum to give (R)-tert-butyl 2-isopropyl-4-(4-(methoxycarbonyl)-5-(methylthio)-2-nitrophenyl)-3-oxopiperazine-1-carboxylate (31.9 g, 100% yield) as a yellow solid. The residue was used directly for the next step without further purification. LC-MS MS (ESI) m/z 412.1 [M-56+H]⁺, 490.2 [M+Na]⁺.

Step 7:

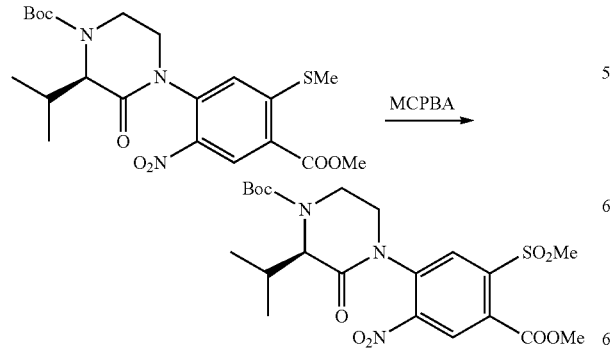

To a 2 L round-bottom flask containing (R)-tert-butyl 2-isopropyl-4-(4-(methoxycarbonyl)-5-(methylthio)-2-nitrophenyl)-3-oxopiperazine-1-carboxylate (crude 91.7 g, 0.196 mol) in CH₂Cl₂ (1 L) was added m-CPBA (84.6 g, 0.49 mmol, 2.5 eq). The mixture was stirred at rt overnight. Sat. Na₂S₂O₃ solution was added slowly to quench the reaction. The mixture was extracted with CH₂Cl₂ (4×3 L). The combined organic layers were washed successively with Na₂S₂O₃ solution (500 mL), NaHCO₃ solution (500 mL) and brine, dried over anhydrous Na₂SO₄, filtered and concentrated under vacuum. The residue was purified by column chromatography on silica gel eluting with dichloromethane to give (R)-tert-butyl 2-isopropyl-4-(4-(methoxycarbonyl)-5-(methylsulfonyl)-2-nitrophenyl)-3-oxopiperazine-1-carboxylate (83.7 g, 85.4% yield) as a yellow solid. LC-MS MS (ESI) m/z 444.0 [M-56+H]⁺, 522.1 [M+Na]⁺. ¹H NMR (CDCl₃ 300 MHz): δ 8.29 (s, 1H), 8.12 (s, 1H), 4.61-4.17 (m, 2H), 4.00-3.94 (m, 4H), 3.70-3.60 (m, 1H), 3.51-3.43 (m, 4H), 2.39-2.32 (m, 1H), 1.50 (s, 9H), 1.07 (d, J=6.9 Hz, 3H), 1.01 (d, J=6.9 Hz, 3H).

Step 8:

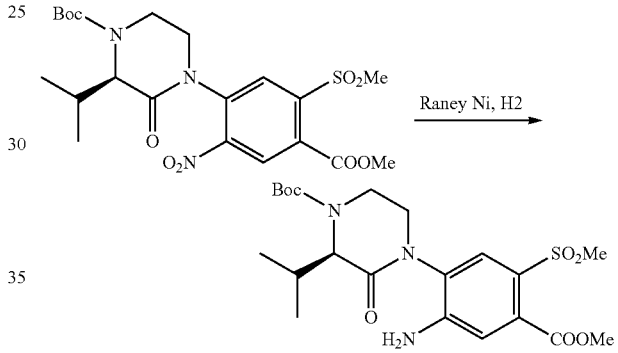

To a 1 L round-bottom flask containing (R)-tert-butyl 2-isopropyl-4-(4-(methoxycarbonyl)-5-(methylsulfonyl)-2-nitrophenyl)-3-oxopiperazine-1-carboxylate (26.3 g, 0.0526 mol) in THF (200 mL) and methanol (200 mL) was added Raney Nickel (in H₂O, 4 g). The mixture was stirred under H₂ (30 psi) at rt overnight. The mixture was filtered and concentrated under vacuum to give (R)-tert-butyl 4-(2-amino-4-(methoxycarbonyl)-5-(methylsulfonyl)phenyl)-2-isopropyl-3-oxopiperazine-1-carboxylate (24.7 g, 100% yield) as a yellow solid. The residue was used directly for the next step without further purification. LC-MS MS (ESI) m/z 414.0 [M-56+H]⁺, 492.0 [M+Na]⁺. ¹H NMR (CDCl₃ 300 MHz): δ 7.77 (brs, 1H), 7.04 (s, 1H), 4.68-4.45 (m, 1H), 4.45-4.38 (m, 2H), 3.92 (s, 3H), 3.70-3.58 (m, 1H), 3.58-3.41 (m, 1H), 3.30 (s, 3H), 2.49-2.25 (m, 1H), 1.50 (s, 9H), 1.12 (d, J=6.9 Hz, 3H), 1.05 (d, J=6.9 Hz, 3H).

Step 9:

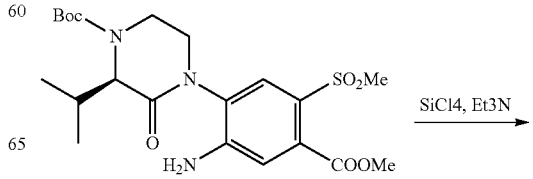

-continued

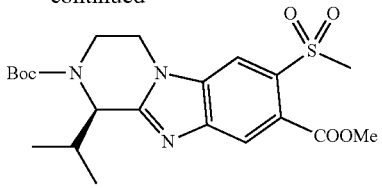

To a 1 L round-bottom flask containing (R)-tert-butyl 4-(2-amino-4-(methoxycarbonyl)-5-(methylsulfonyl)phenyl)-2-isopropyl-3-oxopiperazine-1-carboxylate (25 g, 0.0532 mol) in dichloromethane (500 mL) were added Et₃N (64.5 g, 0.638 mol, 12 eq.) and SiCl₄ (27.1 g, 0.160 mol, 3 eq.). The mixture was stirred at rt overnight. The mixture was added dropwise to aq. NaHCO₃ solution (54.1 g in 1 L of water, 0.644 mol, 12.1 eq.) at 0° C. slowly and adjusted to pH=8. The mixture was filtered and the aqueous layer was extracted with dichloromethane (3×600 mL). The combined organic layers were washed with brine, and then dried over anhydrous Na₂SO₄. The mixture was filtered and concentrated under vacuum to give the residue. The residue was purified by column chromatography on silica gel eluting with petroleum ether:EtOAc 2:1 to give (R)-2-tert-butyl 8-methyl 1-isopropyl-7-(methylsulfonyl)-3,4-dihydrobenzo[4,5]imidazo[1,2-a]pyrazine-2,8(1H)-dicarboxylate (13.2 g, 55% yield) as a pale yellow solid. Analytical chiral HPLC: $t_R$=9.03 min in 15 min chromatography (Method: OD-3_3_5_40_2.5 ML). LC-MS MS (ESI) m/z 452.2 [M+H]⁺. ¹H NMR (CD₃OD 400 MHz): δ 8.31 (s, 1H), 8.01 (s, 1H), 5.30-5.18 (m, 1H), 4.70-4.52 (m, 1H), 4.47 (dd, J=3.2 and 12.4 Hz, 1H), 4.18 (dt, J=5.2 and 11.6 Hz, 1H), 3.98 (s, 3H), 3.70-3.52 (m, 1H), 3.44 (s, 3H), 2.50-2.38 (m, 1H), 1.53 (s, 9H), 1.25 (d, J=6.8 Hz, 3H), 1.06 (d, J=6.8 Hz, 3H).

Step 10:

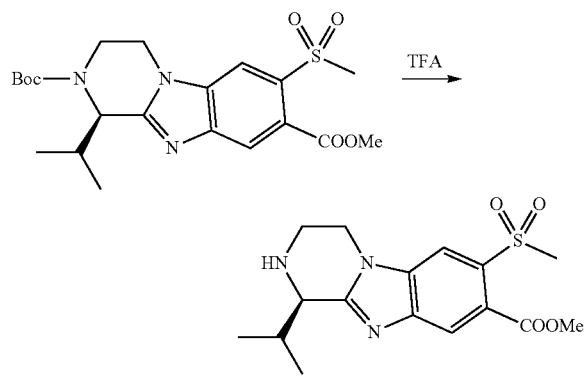

TFA (4 mL) was added dropwise to a solution of containing (R)-2-tert-butyl 8-methyl 1-isopropyl-7-(methylsulfonyl)-3,4-dihydrobenzo[4,5]imidazo[1,2-a]pyrazine-2,8(1H)-dicarboxylate (2.0 g, 4.4 mmol) in DCM (20 mL) at rt over 2 min. The mixture was stirred at rt for 3 h. TLC showed the starting material was consumed completely. The solvent was removed in vacuo at 30° C., and then DCM (10 mL) was added. The mixture was neutralized with sat. aq. NaHCO₃ to pH=7. The mixture was extracted with DCM (3×20 mL) and the combined organic layers were dried over anhydrous Na₂SO₄, filtered and concentrated under vacuum to afford (R)-methyl 1-isopropyl-7-(methylsulfonyl)-1,2,3,4-tetrahydrobenzo[4,5]imidazo[1,2-a]pyrazine-8-carboxylate (1.5 g, 96.4% yield) as a white solid. LC-MS m/z 351.9 [M+H]⁺, 374.0 [M+Na]⁺. ¹H NMR (CDCl₃ 300 MHz): δ 8.15 (s, 1H), 8.07 (s, 1H), 4.26-4.05 (m, 3H), 3.97 (s, 3H), 3.63-3.50 (m, 1H), 3.44 (s, 3H), 3.32-3.16 (m, 1H), 2.85-2.66 (m, 1H), 1.16 (d, J=6.9 Hz, 3H), 0.88 (d, J=6.6 Hz, 3H).

Step 11:

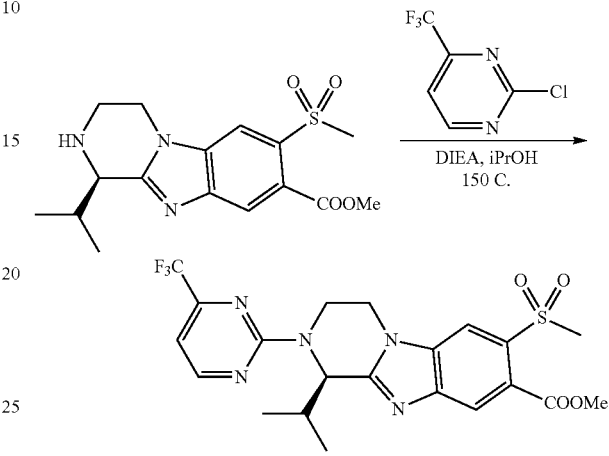

A mixture of (R)-methyl 1-isopropyl-7-(methylsulfonyl)-1,2,3,4-tetrahydrobenzo[4,5]imidazo[1,2-a]pyrazine-8-carboxylate (0.9 g, 2.56 mmol), 2-chloro-4-(trifluoromethyl)pyrimidine (1.0 g, 5.1 mmol, 2 eq.) and DIEA (1.0 g, 7.7 mmol, 3 eq.) in i-PrOH (6 mL) was stirred in a microwave oven at 150° C. for 2 h. TLC showed the starting material was consumed completely (PE:EtOAc=3:1). The solvent was removed in vacuo at 40° C., and the residue was purified by column chromatography on silica gel eluting with PE/EtOAc=6/1 to give (R)-methyl 1-isopropyl-7-(methylsulfonyl)-2-(4-(trifluoromethyl)pyrimidin-2-yl)-1,2,3,4-tetrahydrobenzo[4,5]imidazo[1,2-a]pyrazine-8-carboxylate (1.0 g, 78% yield) as a white solid. LC-MS m/z 498.1 [M+H]⁺. ¹H NMR (CDCl₃ 300 MHz): δ 8.52 (d, J=4.8 Hz, 1H), 8.13 (s, 1H), 8.06 (s, 1H), 6.83 (d, J=4.8 Hz, 1H), 6.06 (d, J=7.8 Hz, 1H), 5.39-5.28 (m, 1H), 4.33-4.24 (m, 1H), 4.20-4.12 (m, 1H), 3.93 (s, 3H), 3.77-3.65 (m, 1H), 3.39 (s, 3H), 2.52-2.38 (m, 1H), 1.25 (d, J=6.9 Hz, 3H), 1.02 (d, J=6.6 Hz, 3H).

Step 12:

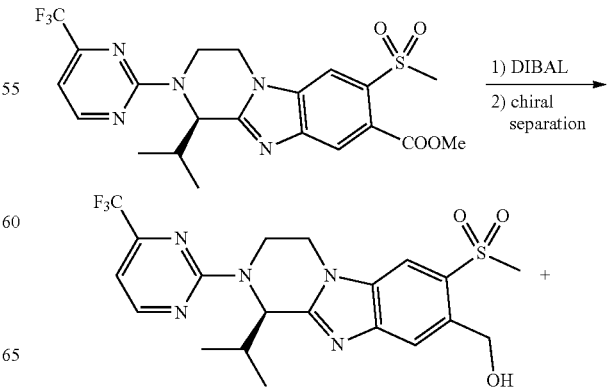

-continued

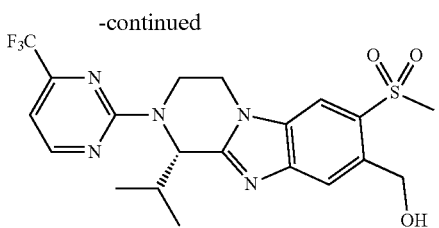

To a solution of (R)-methyl 1-isopropyl-7-(methylsulfonyl)-2-(4-(trifluoromethyl)pyrimidin-2-yl)-1,2,3,4-tetrahydrobenzo[4,5]imidazo[1,2-a]pyrazine-8-carboxylate (1.3 g, 2.6 mmol) in DCM (15 mL) was added DIBAL-H (1M in toluene, 10.4 mL, 10.4 mmol, 4 eq.) at −78° C. The mixture was stirred at −78° C. for 2 h. Sat. aq NH$_4$Cl (25 mL) was added and the mixture was filtered. The aqueous layer was extracted with DCM (3×20 mL). The combined organic layers were washed with brine, dried over anhydrous Na$_2$SO$_4$, filtered and concentrated under vacuum. The residue was purified by column chromatography on silica gel eluting with DCM/MeOH=30/1 to give a partially racemized mixture (1.1 g, 91.6% yield) as a white solid. The racemized mixture was purified by SFC separation on a chiral column to give (R)-(1-isopropyl-7-(methylsulfonyl)-2-(4-(trifluoromethyl)pyrimidin-2-yl)-1,2,3,4-tetrahydrobenzo[4,5]imidazo[1,2-a]pyrazin-8-yl)methanol (Isomer 1) (0.65 g, 54.1% yield) as a white solid and (S)-(1-isopropyl-7-(methylsulfonyl)-2-(4-(trifluoromethyl)pyrimidin-2-yl)-1,2,3,4-tetrahydrobenzo[4,5]imidazo[1,2-a]pyrazin-8-yl)methanol (Isomer 2) (0.15 g, 12.5% yield) as a white solid.

Isomer 1: (R)-(1-isopropyl-7-(methylsulfonyl)-2-(4-(trifluoromethyl)pyrimidin-2-yl)-1,2,3,4-tetrahydrobenzo[4,5]imidazo[1,2-a]pyrazin-8-yl)methanol Analytical chiral HPLC: t$_R$=8.768 min in 15 min chromatography (Method: AD-H_5_5_40_2.35 ML). LC-MS m/z 470.1 [M+H]$^+$. $^1$H NMR (CDCl$_3$ 400 MHz): δ 8.58 (d, J=4.8 Hz, 1H), 8.13 (s, 1H), 7.89 (s, 1H), 6.89 (d, J=4.8 Hz, 1H), 6.12 (d, J=8.0 Hz, 1H), 5.40-5.36 (m, 1H), 5.06-5.03 (m, 2H), 4.35-4.31 (m, 1H), 4.21-4.16 (m, 1H), 3.82-3.76 (m, 1H), 3.23 (s, 3H), 3.09 (t, J=6.8 Hz, 1H), 2.52-2.50 (m, 1H), 1.32 (d, J=6.8 Hz, 3H), 1.08 (d, J=6.8 Hz, 3H). $^1$H NMR (CD$_3$OD 400 MHz): δ 8.69 (d, J=4.8 Hz, 1H), 8.22 (s, 1H), 7.94 (s, 1H), 7.02 (d, J=4.8 Hz, 1H), 6.05 (d, J=8.0 Hz, 1H), 5.34 (d, J=10.0 Hz, 1H), 5.10 (s, 2H), 4.50 (dd, J$_1$=12.0 Hz, J$_2$=3.6 Hz, 1H), 4.22 (td, J$_1$=12.0 Hz, J$_2$=5.2 Hz, 1H), 3.88 (dddd, J$_1$=14.4 Hz, J$_2$=10.0 Hz, J$_3$=4.4 Hz, 1H), 3.26 (s, 3H), 2.60-2.52 (m, 1H), 1.28 (d, J=6.8 Hz, 3H), 1.06 (d, J=6.8 Hz, 3H).

Isomer 1 was recrystallized as a crystalline solid by following procedure:

(R)-(1-isopropyl-7-(methylsulfonyl)-2-(4-(trifluoromethyl)pyrimidin-2-yl)-1,2,3,4-tetrahydrobenzo[4,5]imidazo[1,2-a]pyrazin-8-yl)methanol (470 mg) was dissolved into EtOAc (3.0 mL) followed by slow addition of hexanes (ca. 5 mL) until the solution turns cloudy. Several drops of EtOAc were added to cause the cloudiness to disappear. The solution was allowed to stand at rt until crystals formed. The crystalline solid was collected by filtration. m.p. 188-189° C.

Isomer 2: (S)-(1-isopropyl-7-(methylsulfonyl)-2-(4-(trifluoromethyl)pyrimidin-2-yl)-1,2,3,4-tetrahydrobenzo[4,5]imidazo[1,2-a]pyrazin-8-yl)methanol Analytical chiral HPLC: t$_R$=7.780 min in 15 min chromatography (Method: AD-H_5_5_40_2.35 ML). LC-MS m/z 470.1 [M+H]$^+$. $^1$H NMR (CDCl$_3$ 400 MHz): δ 8.58 (d, J=5.2 Hz, 1H), 8.12 (s, 1H), 7.88 (s, 1H), 6.89 (d, J=4.8 Hz, 1H), 6.11 (d, J=8.0 Hz, 1H), 5.40-5.35 (m, 1H), 5.04-5.00 (m, 2H), 4.34-4.31 (m, 1H), 4.21-4.16 (m, 1H), 3.82-3.75 (m, 1H), 3.22 (s, 3H), 2.52-2.50 (m, 1H), 1.31 (d, J=6.8 Hz, 3H), 1.08 (d, J=6.8 Hz, 3H).

Alternatively, a racemic mixture of methyl 1-isopropyl-7-(methylsulfonyl)-2-(4-(trifluoromethyl)pyrimidin-2-yl)-1,2,3,4-tetrahydrobenzo[4,5]imidazo[1,2-a]pyrazine-8-carboxylate was prepared by the following method.

(rac)-methyl 1-isopropyl-7-(methylsulfonyl)-2-(4-(trifluoromethyl)pyrimidin-2-yl)-1,2,3,4-tetrahydrobenzo[4,5]imidazo[1,2-a]pyrazine-8-carboxylate

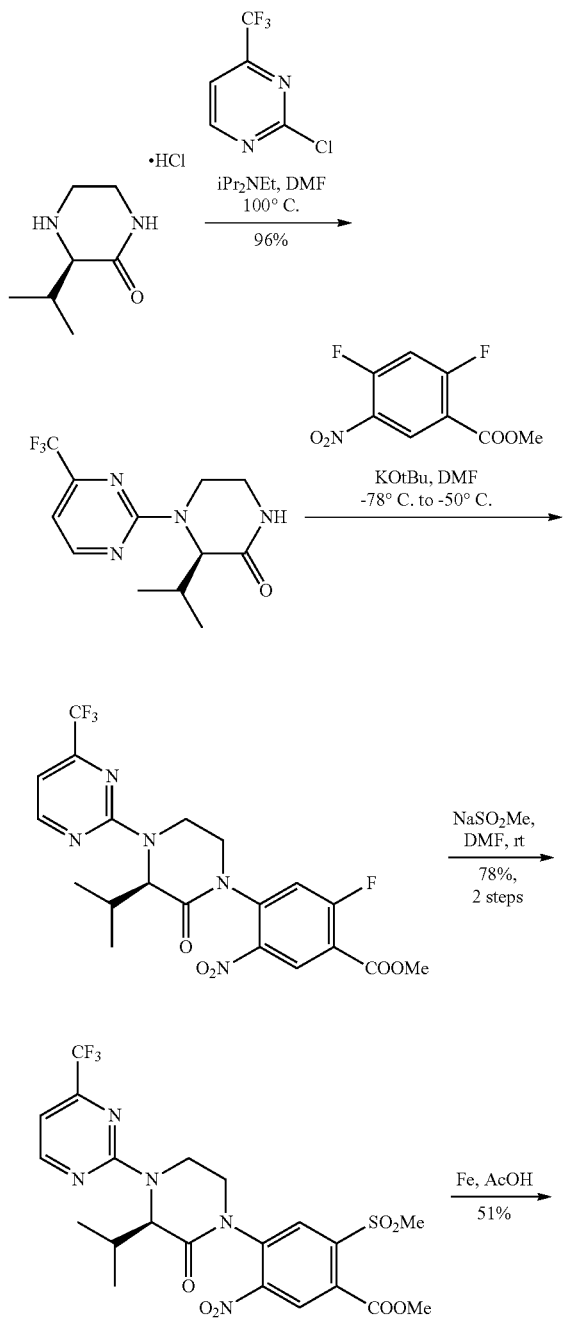

-continued

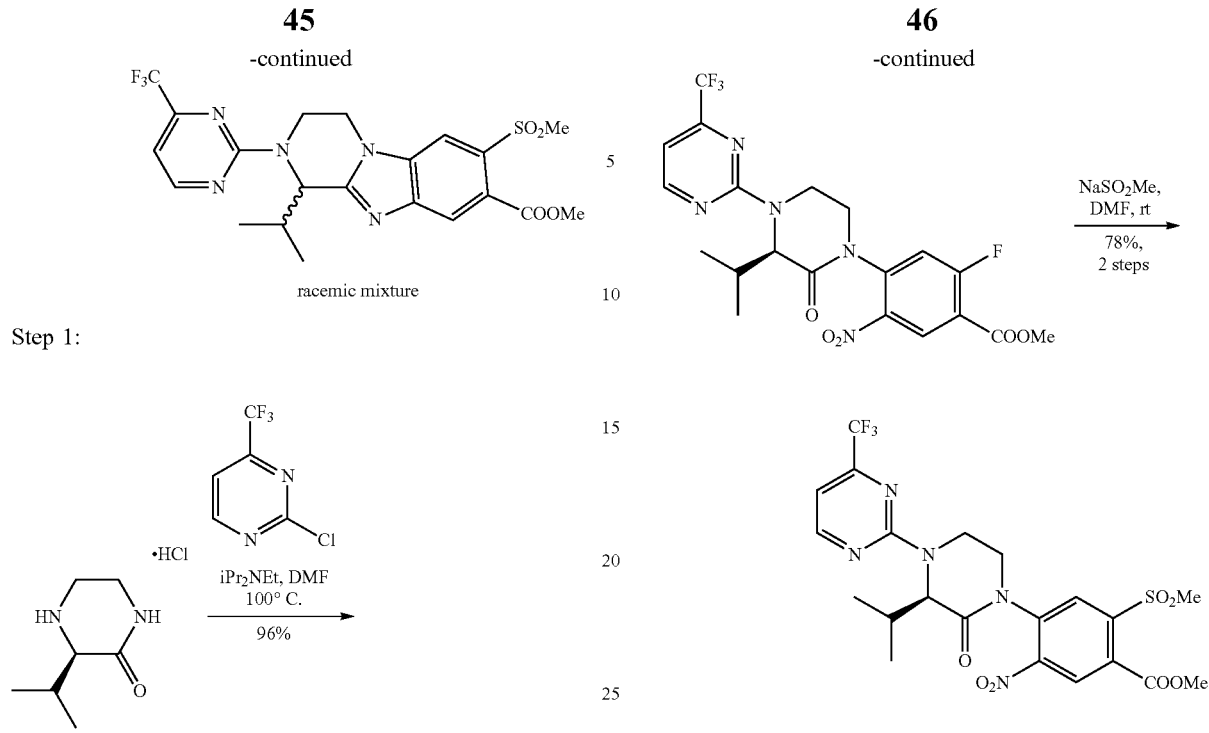

racemic mixture

Step 1:

To a solution of (R)-3-isopropylpiperazin-2-one hydrochloride (2.61 g, 14.62 mmol) and iPr$_2$NEt (7.60 mL, 43.86 mmol) in DMF (20 mL) was added a solution of 2-chloro-4-(trifluoromethyl)pyrimidine (3.47 g, 19.00 mmol) in DMF (2 mL). The resulting solution was stirred at 100° C. under N$_2$ for 3 h at which point the reaction was deemed complete by LC-MS. Sat. aq. NH$_4$Cl (30 mL) was added to quench the reaction, followed by addition of EtOAc (30 mL). The EtOAc layer was separated and the aqueous layer was extracted with EtOAc (3×20 mL). The EtOAc layers were combined, dried using Na$_2$SO$_4$ and evaporated to give nearly pure crude product. Purification on a silica cartridge using CISCO FCC eluting with 100% EtOAc gave 4.03 grams of (R)-3-isopropyl-4-(4-(trifluoromethyl)pyrimidin-2-yepiperazin-2-one (96%) as a slightly orange thick oil. LC-MS m/z 289.17 [M+H ]$^+$. $^1$H NMR (CDCl$_3$, 400 MHz): δ 8.52 (d, J=4.8 Hz, 1H), 6.82 (d, J=4.4 Hz, 1H), 6.56 (br, 1H), 5.20 (d, J=6.8 Hz, 1H), 4.83-4.77 (m, 1H), 3.55-3.37 (m, 3H), 2.49-2.41 (m, 1H), 1.15 (d, J=6.8 Hz, 3H), 1.04 (d, J=6.8 Hz, 3H).

Steps 2 and 3:

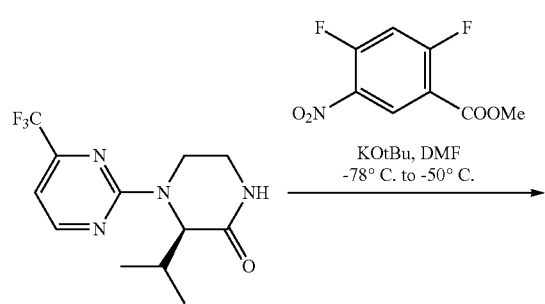

To a solution of (R)-3-isopropyl-4-(4-(trifluoromethyl)pyrimidin-2-yl)piperazin-2-one (986 mg, 3.42 mmol) in DMF (5 mL) was added a 2 M solution of KOtBu in THF (2.14 mL, 4.28 mmol) dropwise at 0° C. The reaction stirred for 1 h at 0° C. and was then cooled to −78° C. In a separate flask, a solution of methyl 2,4-difluoro-5-nitrobenzoate (928 mg, 4.28 mmol) in DMF (15 mL) was cooled to −78° C. To this solution was added a solution of the above anion via cannula at −78° C. over a 5 min period. The reaction was allowed to warm to −50° C. and stirred at this temperature for 2 h. Sat. aq. NH$_4$Cl (20 mL) was added to quench the reaction, followed by EtOAc (30 mL). The EtOAc layer was separated and the aqueous layer was extracted with EtOAc (3×15 mL). The EtOAc layers were combined, dried and evaporated to give crude (R)-methyl-2-fluoro-4-(3-isopropyl-2-oxo-4-(4-(trifluoromethyl)pyrimidin-2-yl)piperazin-1-yl)-5-nitrobenzoate which was taken on directly for the next step without further purification.

LC-MS m/z 486.20 [M+H]$^+$.

To a solution of the above crude (R)-methyl 2-fluoro-4-(3-isopropyl-2-oxo-4-(4-(trifluoromethyl)pyrimidin-2-yl) piperazin-1-yl)-5-nitrobenzoate in DMF (15 mL) was added NaSO$_2$Me (1.05 g, 10.30 mmol) in one portion at rt. After stirring for 3 h, the reaction was deemed complete by LC-MS analysis. Water (100 mL) was added and the mixture stirred vigorously for 20 minutes before filtering off the solid material. To this solid material was added 20% EtOAc in Hexanes and the mixture stirred vigorously for 10 minutes. The EtOAc/Hexanes filtrate was collected and evaporated to give 1.45 g of (R)-methyl 4-(3-isopropyl-2-oxo-4-(4-(trifluoromethyl)pyrimidin-2-yl)piperazin-1-yl)-2-(methylsulfonyl)-5-nitrobenzoate as an off-white solid (78%, 2 steps). LC-MS m/z 546.27 [M+H]$^+$. $^1$H NMR (CDCl$_3$, 400 MHz): δ 8.59 (d, J=4.4 Hz, 1H), 8.32 (s, 1H), 8.14 (s, 1H), 6.92 (d, J=5.2 Hz, 1H), 5.32 (d, J=6.8 Hz, 1H), 5.04-5.00 (m, 1H), 4.12-4.02 (m, 1H), 4.03 (s, 3H), 3.88-3.80 (m, 2H), 3.44 (s, 3H), 2.55-2.50 (m, 1H), 1.15 (d, J=6.8 Hz, 3H), 1.06 (d, J=6.8 Hz, 3H).

Step 4:

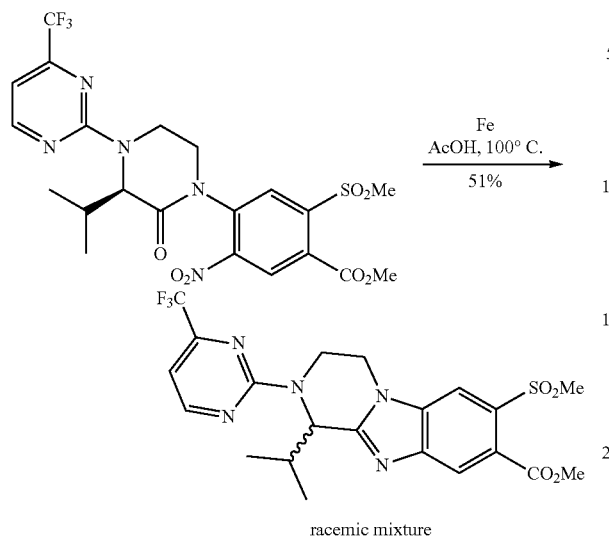

racemic mixture

To a solution of (R)-methyl-4-(3-isopropyl-2-oxo-4-(4-(trifluoromethyl)pyrimidin-2-yl)piperazin-1-yl)-2-(methylsulfonyl)-5-nitrobenzoate (1.45 g, 2.66 mmol) in glacial acetic acid (17 mL) was added iron powder (445 mg, 7.97 mmol). The mixture was heated to 100° C. After 5 min, the suspended iron dissolved into solution. The mixture was stirred at 100° C. for 48 h, at which point the flask was cooled to rt and the contents were poured into ice. The mixture was extracted with EtOAc (2×75 mL), then the combined organic layers were washed with water (2×50 mL) and brine (50 mL). The solution was dried over $MgSO_4$, filtered through cotton, and concentrated in vacuo. The residue was purified on a silica cartridge (0% EtOAc in hexanes, then 50%) to yield 680 mg of methyl-1-isopropyl-7-(methylsulfonyl)-2-(4-(trifluoromethyl)pyrimidin-2-yl)-1,2,3,4-tetrahydrobenzo[4,5]imidazo[1,2-a]pyrazine-8-carboxylate as a racemic mixture (51%). LC-MS: m/z 498.32 $(M+H)^+$. $^1$H NMR ($CDCl_3$, 400 MHz): δ 8.58 (d, J=4.8 Hz, 1H), 8.20 (s, 1H), 8.12 (s, 1H), 6.90 (d, J=4.8 Hz, 1H), 6.13 (d, J=8.4 Hz, 1H), 5.39 (dd, J=4.8 Hz, 14.4 Hz, 1H), 4.35 (ddd, J=1.2 Hz, 4.4 Hz, 12.0 Hz, 1H), 4.21 (dt, J=4.8 Hz, 12.0 Hz, 1H), 4.00 (s, 3H), 3.78 (ddd, J=4.4 Hz, 11.6 Hz, 14.4 Hz, 1H), 3.45 (s, 3H), 2.48 (sept, J=7.2 Hz, 1H), 1.32 (d, J=6.4 Hz, 3H), 1.08 (d, J=6.8 Hz, 3H).

Example 3

(R)-1-isopropyl-7-(methylsulfonyl)-2-(4-(trifluoromethyl)pyrimidin-2-yl)-1,2,3,4-tetrahydropyrazino[1,2-a]indole and (S)-1-isopropyl-7-(methylsulfonyl)-2-(4-(trifluoromethyl)pyrimidin-2-yl)-1,2,3,4-tetrahydropyrazino[1,2-a]indole

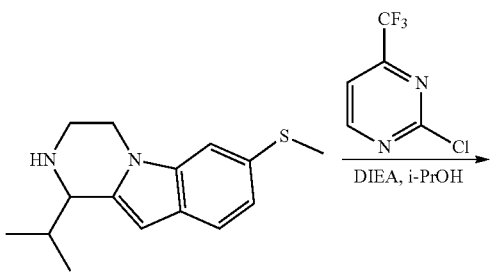

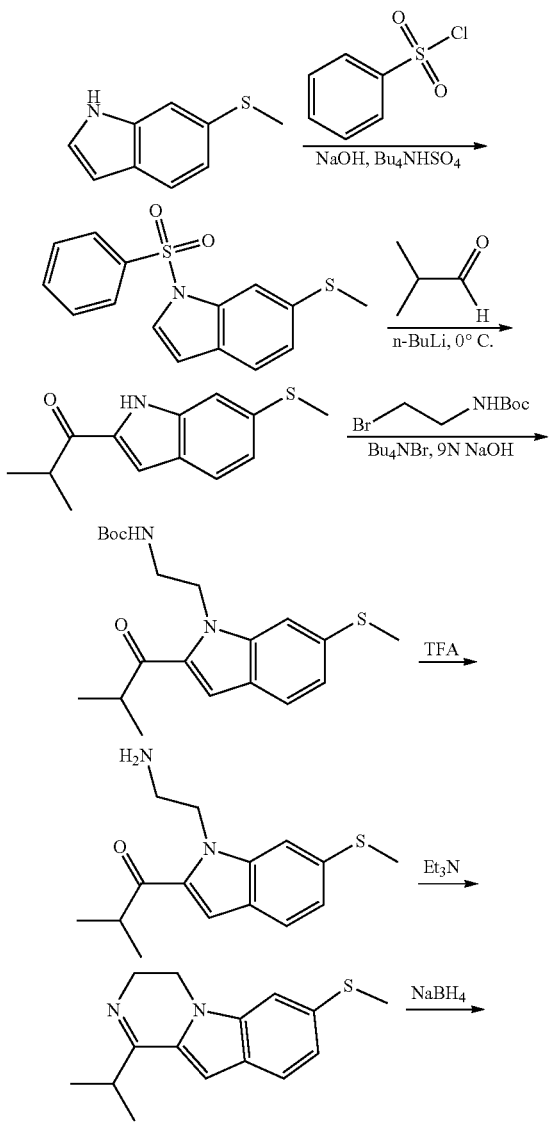

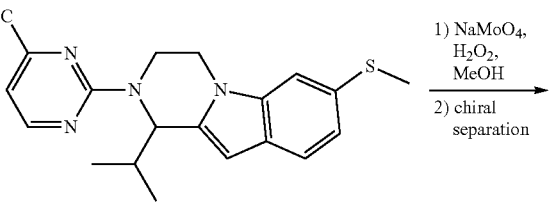

-continued

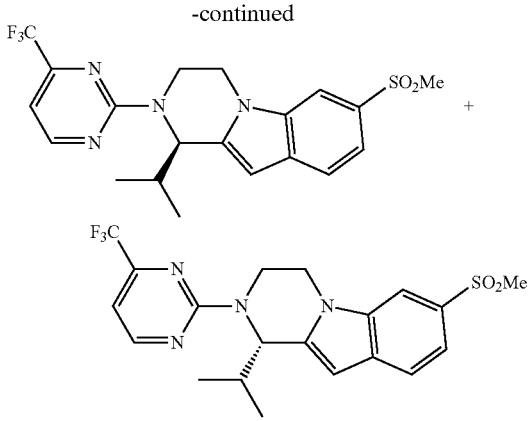

Step 1:

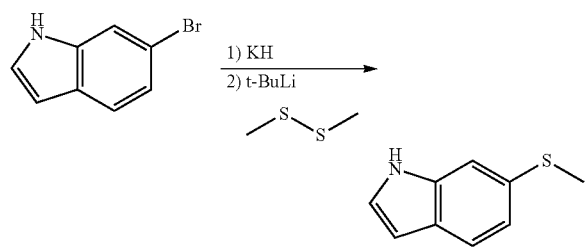

To a solution of 6-bromo-1H-indole (5 g, 25.50 mmol) in anhydrous THF (60 mL) at 0° C. was added KH (6.80 g, 51.00 mmol, 30% wt in mineral oil). After stirring for 30 min, the mixture was cooled to −78° C. and t-BuLi (39.23 mL, 51.0 mmol, 1.3 M) was added under nitrogen. After 30 min, 1,2-dimethyldisulfane (4.80 g, 51.0 mmol) was added to the mixture. The reaction mixture was stirred at −78° C. for 1 h and quenched with sat. aq NH$_4$Cl (30 mL) at −78° C. slowly (Caution: flame), adjusted pH=7 with 1 N aqueous phosphoric acid and extracted with EtOAc (50 mL×3). The combined organic layers were dried over anhydrous Na$_2$SO$_4$, filtered, concentrated and purified by column chromatography on silica gel eluted with (petroleum ether/EtOAc 10:1) to give 6-(methylthio)-1H-indole (3.9 g, 93.67% yield) as a grey solid. LC-MS MS (ESI) m/z 164.1 [M+H]$^+$. $^1$H NMR (CDCl$_3$ 400 MHz): δ 8.14 (brs, 1H), 7.56 (d, J=8.0 Hz, 1H), 7.37 (s, 1H), 7.18-7.11 (m, 1H), 6.56-6.51 (m, 1H), 2.52 (s, 3H).

Step 2:

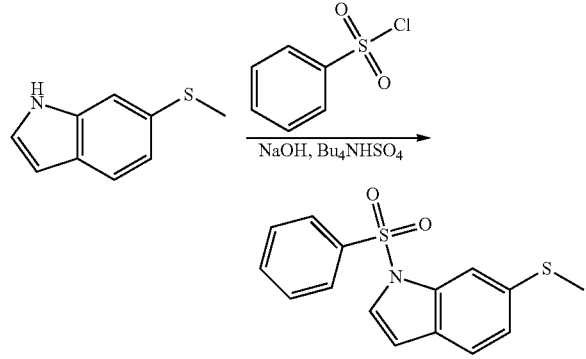

To a solution of 6-(methylthio)-1H-indole (1 g, 6.13 mmol), NaOH (4.90 g, 122.6 mmol) and Bu$_4$NHSO$_4$ (207.8 mg, 0.613 mmol) in dichloromethane (20 mL) was added benzenesulfonyl chloride (1.29 g, 7.36 mmol). The reaction mixture was stirred at rt overnight. The mixture was quenched with water (30 mL) and extracted with CH$_2$Cl$_2$ (30 mL×3). The combined organic layers were dried over anhydrous Na$_2$SO$_4$, filtered, concentrated and purified by column chromatography on silica gel eluted with (petroleum ether/EtOAc 10:1) to afford 6-(methylthio)-1-(phenylsulfonyl)-1H-indole (1.1 g, 59.18% yield) as a white solid. LC-MS MS (ESI) m/z 304.0 [M+H]$^+$. $^1$H NMR (CDCl$_3$ 400 MHz): δ 7.93-7.75 (m, 3H), 7.58-7.41 (m, 5H), 7.17 (dd, J$_1$=8.0 Hz, J$_2$=1.6 Hz, 1H), 6.63-6.60 (m, 1H), 2.53 (s, 3H).

Step 3:

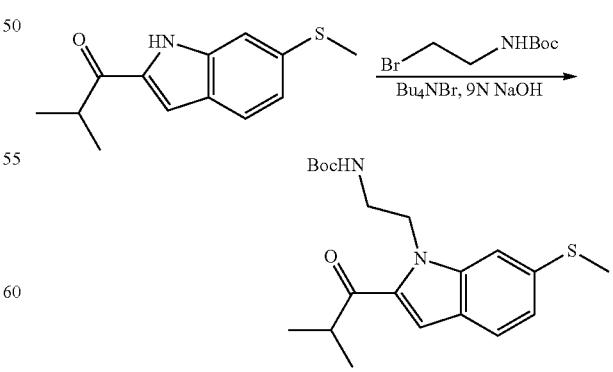

To a solution of 6-(methylthio)-1-(phenylsulfonyl)-1H-indole (890 mg, 2.93 mmol) in anhydrous THF (10 mL) at 0° C. under nitrogen was added n-BuLi (5.86 mL, 14.65 mmol, 2.5 M). After stirring for 30 min, isobutyraldehyde (1.05 g, 14.65 mmol) was added. The reaction mixture was stirred at 0° C. for 1 h and quenched with sat. aq NH$_4$Cl (10 mL) at 0° C. and extracted with EtOAc (20 mL×3). The combined organic layers were dried over anhydrous sodium sulfate, filtered, concentrated and purified by column chromatography on silica gel eluted with (petroleum ether/EtOAc 20:1) to give 2-methyl-1-(6-(methylthio)-1H-indol-2-yl)propan-1-one (440 mg, 64.28% yield) as a colorless oil.

LC-MS MS (ESI) m/z 234.1 [M+H]$^+$. $^1$H NMR (CDCl$_3$ 400 MHz): δ 8.86 (brs, 1H), 7.52 (d, J=8.4 Hz, 1H), 7.19 (s, 1H), 7.14-7.11 (m, 1H), 7.01 (dd, J$_1$=8.4 Hz, J$_2$=1.6, 1H), 3.42-3.38 (m, 1H), 2.47 (s, 3H), 1.20 (d, J=6.8 Hz, 6H).

Step 4:

To a solution of 2-methyl-1-(6-(methylthio)-1H-indol-2-yl)propan-1-one (600 mg, 2.57 mmol) and Bu$_4$NBr (4.12 g, 12.85 mmol) in 9 N NaOH (10 mL, cooled) was added tert-butyl (2-bromoethyl)carbamate (2.87 g, 12.85 mmol). The reaction mixture was stirred at rt for 72 h. The mixture was diluted with water (20 mL) at 0° C. and extracted with EtOAc (20 mL×3). The combined organic layers were dried over anhydrous Na₂SO₄, filtered, concentrated and purified by column chromatography on silica gel eluting with (petroleum ether/EtOAc 10:1) to afford tert-butyl (2-(2-isobutyryl-6-(methylthio)-1H-indol-1-yl)ethyl)carbamate (200 mg, 20.66% yield) as a colorless oil. LC-MS MS (ESI) m/z 321.1 [M-56+H]⁺, 277.1 [M-100+H]⁺. ¹H NMR (CDCl₃ 400 MHz): δ 7.57 (d, J=8.4 Hz, 1H), 7.38 (s, 1H), 7.29 (s, 1H), 7.10 (d, J=8.4 Hz, 1H), 4.80 (brs, 1H), 4.62 (t, J=6.4 Hz, 2H), 3.58-3.42 (m, 3H), 2.58 (s, 3H), 1.38 (s, 9H), 1.24 (d, J=6.8 Hz, 6H).

Step 5:

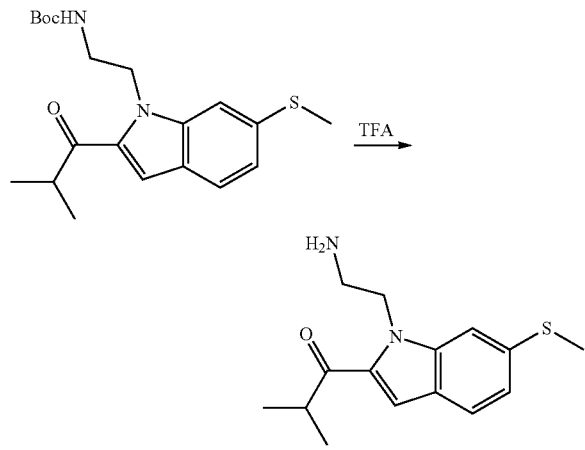

To a solution of tert-butyl (2-(2-isobutyryl-6-(methylthio)-1H-indol-1-yl)ethyl)carbamate (200 mg, 0.53 mmol) in CH₂Cl₂ (9 mL) at 0° C. was added TFA (1 mL). The reaction mixture was stirred at rt for 1 h. The mixture was concentrated (T<25° C.), treated with water (5 mL), adjusted to pH=1 with sat. NaHCO₃ and extracted with EtOAc (20 mL×3). The combined organic layers were dried over anhydrous Na₂SO₄, filtered, concentrated to afford 1-(1-(2-aminoethyl)-6-(methylthio)-1H-indol-2-yl)-2-methylpropan-1-one (210 mg, 100% yield) as a colorless oil. LC-MS MS (ESI) m/z 258.8 [M-18+H]⁺.

Step 6:

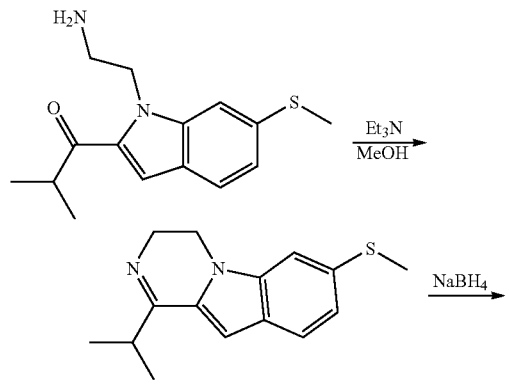

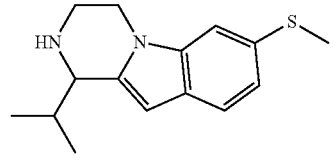

To a solution of 1-(1-(2-aminoethyl)-6-(methylthio)-1H-indol-2-yl)-2-methylpropan-1-one (200 mg, 0.724 mmol) in MeOH (5 mL) was added Et₃N (219.3 mg, 2.172 mmol). The reaction mixture was stirred at 60° C. for 1 h. NaBH₄ (82.53 mg, 2.172 mmol) was added. The mixture was stirred at 60° C. for 1 h. The mixture was concentrated, treated with water (10 mL) and extracted with EtOAc (20 mL×3). The combined organic layers were dried over anhydrous Na₂SO₄, filtered, concentrated and purified by preparative TLC on silica gel eluted with (petroleum ether/EtOAc 1:1) to afford 1-isopropyl-7-(methylthio)-1,2,3,4-tetrahydropyrazino[1,2-a]indole (80 mg, 42.46% yield, store at 0° C.) as a colorless oil.

LC-MS of 1-Isopropyl-7-methylsulfanyl-3,4-dihydropyrazino[1,2-a]indole MS (ESI) m/z 259.1 [M+H]⁺. LC-MS of 1-isopropyl-7-(methylthio)-1,2,3,4-tetrahydropyrazino[1,2-a]indole MS (ESI) m/z 261.2 [M+H]⁺. ¹H NMR (CDCl₃ 400 MHz): δ 7.41 (d, J=8.4 Hz, 1H), 7.20 (s, 1H), 7.05 (dd, J₁=8.4 Hz, J₂=1.6 Hz, 1H), 6.12 (s, 1H), 4.02-3.97 (m, 2H), 3.86-3.80 (m, 1H), 3.46-3.42 (m, 1H), 3.16-3.10 (m, 1H), 2.48 (s, 3H), 2.32-2.27 (m, 1H), 1.09 (d, J=6.8 Hz, 3H), 0.86 (d, J=6.8 Hz, 3H).

Step 7:

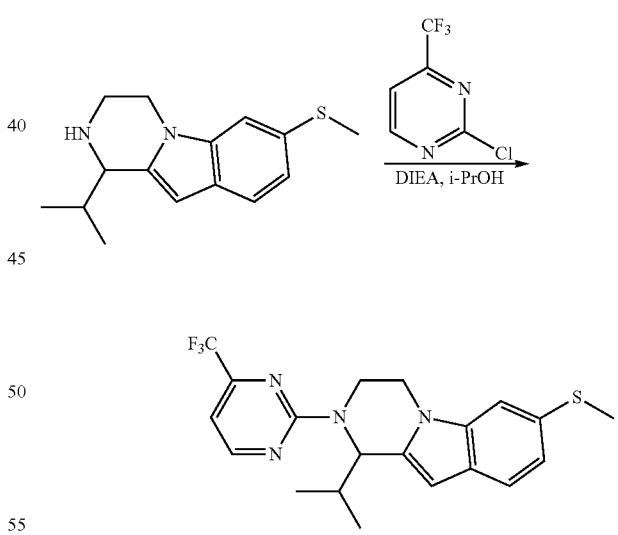

To a solution of 1-isopropyl-7-(methylthio)-1,2,3,4-tetrahydropyrazino[1,2-a]indole (50 mg, 0.19 mmol) in ⁱPrOH (2 mL) was added 2-chloro-4-(trifluoromethyl)pyrimidine (105 mg, 0.58 mmol) and DIEA (185 mg, 0.96 mmol). The mixture was stirred at 100° C. for 4 h. The mixture was concentrated under vacuum and the residue was purified by preparative TLC to afford 1-isopropyl-7-(methylthio)-2-(4-(trifluoromethyl)pyrimidin-2-yl)-1,2,3,4-tetrahydropyrazino[1,2-a]indole (45 mg, 57.7% yield) as a yellow oil. LC-MS MS (ESI) m/z 407.1 [M+H]⁺.

Step 8:

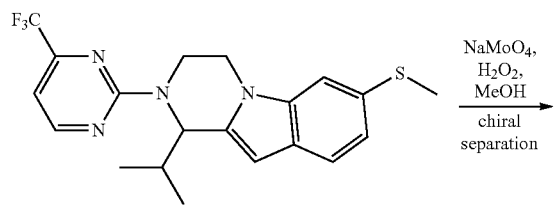

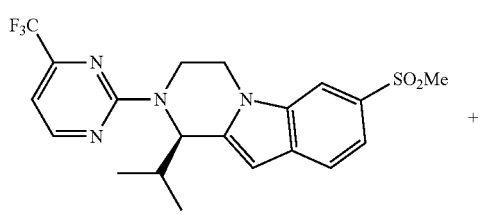

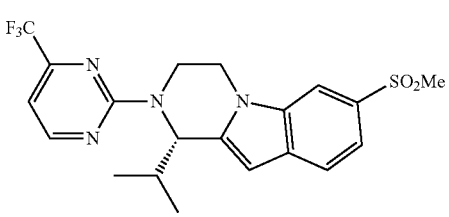

To a solution of 1-isopropyl-7-(methylthio)-1,2,3,4-tetrahydropyrazino[1,2-a]indole (45 mg, 0.11 mmol) in MeOH (1 mL). was added NaMoO$_4$-2H$_2$O (61 mg, 0.33 mmol) and 30% H$_2$O$_2$(67 mg, 0.55 mmol) at 0° C. The mixture was stirred at rt for 2 h. Sat. Na$_2$S$_2$O$_3$ (5 mL) was added and the mixture was concentrated under vacuum. The aqueous layer was extracted with EtOAc (3×10 mL). The combined organic layers were washed with brine, dried over anhydrous Na$_2$SO$_4$, filtered and concentrated under vacuum. The residue was purified by preparative TLC and SFC separation on a chiral column to afford isomer 1 (20.10 mg, 46.6% yield) as a white solid and isomer 2 (20.30 mg, 47.1% yield) as a white solid.

Isomer 1: Analytical chiral HPLC: t$_R$=6.64 min in 15 min chromatography (Method: AD-H_5_5_40_2.35 ML). LC-MS MS (ESI) m/z 439.0 [M+H]$^+$. $^1$H NMR (CD$_3$OD 300 MHz): δ 8.63 (d, J=4.8 Hz, 1H), 7.98 (s, 1H), 7.69 (d, J=8.4 Hz, 1H), 7.57 (dd, J=1.5 and 8.4 Hz, 1H), 6.94 (d, J=4.8 Hz, 1H), 6.50 (s, 1H), 5.88 (d, J=8.4 Hz, 1H), 5.11-5.07 (m, 1H), 4.45-4.38 (m, 1H), 4.05 (dt, J=4.8 and 11.4 Hz, 1H), 3.91-3.83 (m, 1H), 3.11 (s, 3H), 2.35-2.27 (m, 1H), 1.14 (d, J=6.6 Hz, 3H), 1.01 (d, J=6.6 Hz, 3H).

Isomer 2: Analytical chiral HPLC: t$_R$=7.37 min in 15 min chromatography (Method: AD-H_5_5_40_2.35 ML). LC-MS MS (ESI) m/z 439.0 [M+H]+, 461.0 [M+Na]$^+$. $^1$H NMR (CD$_3$OD 300 MHz): δ 8.63 (d, J=4.5 Hz, 1H), 7.98 (s, 1H), 7.68 (d, J=8.4 Hz, 1H), 7.57 (dd, J=1.5 and 8.4 Hz, 1H), 6.94 (d, J=4.8 Hz, 1H), 6.49 (s, 1H), 5.87 (d, J=8.1 Hz, 1H), 5.10-5.06 (m, 1H), 4.44-4.37 (m, 1H), 4.03 (dt, J=4.8 and 11.4 Hz, 1H), 3.90-3.80 (m, 1H), 3.11 (s, 3H), 2.34-2.26 (m, 1H), 1.14 (d, J=6.6 Hz, 3H), 1.00 (d, J=6.6 Hz, 3H).

Example 4

(R)-(1-isopropyl-7-(methylsulfonyl)-2-(4-(trifluoromethyl)pyrimidin-2-yl)-1,2,3,4-tetrahydropyrazino[1,2-a]indol-8-yl)methanol and (S)-(1-isopropyl-7-(methylsulfonyl)-2-(4-(trifluoromethyl)pyrimidin-2-yl)-1,2,3,4-tetrahydropyrazino[1,2-a]indol-8-yl)methanol

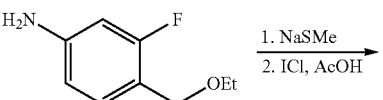

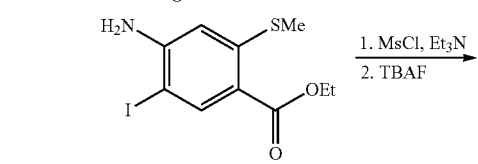

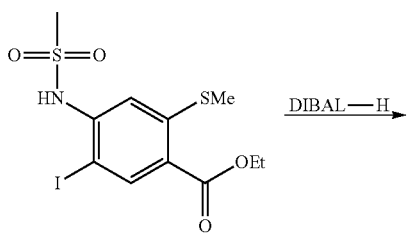

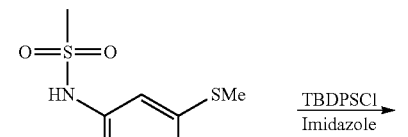

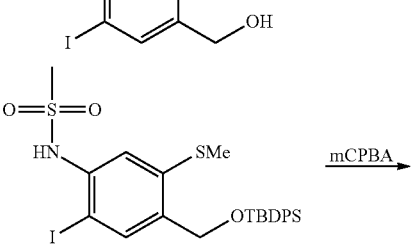

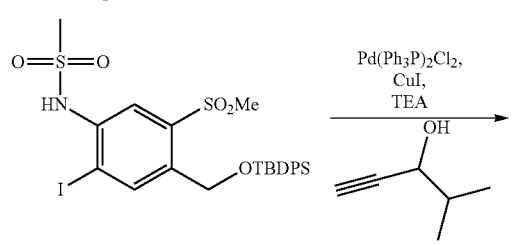

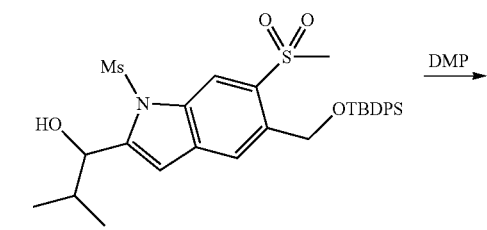

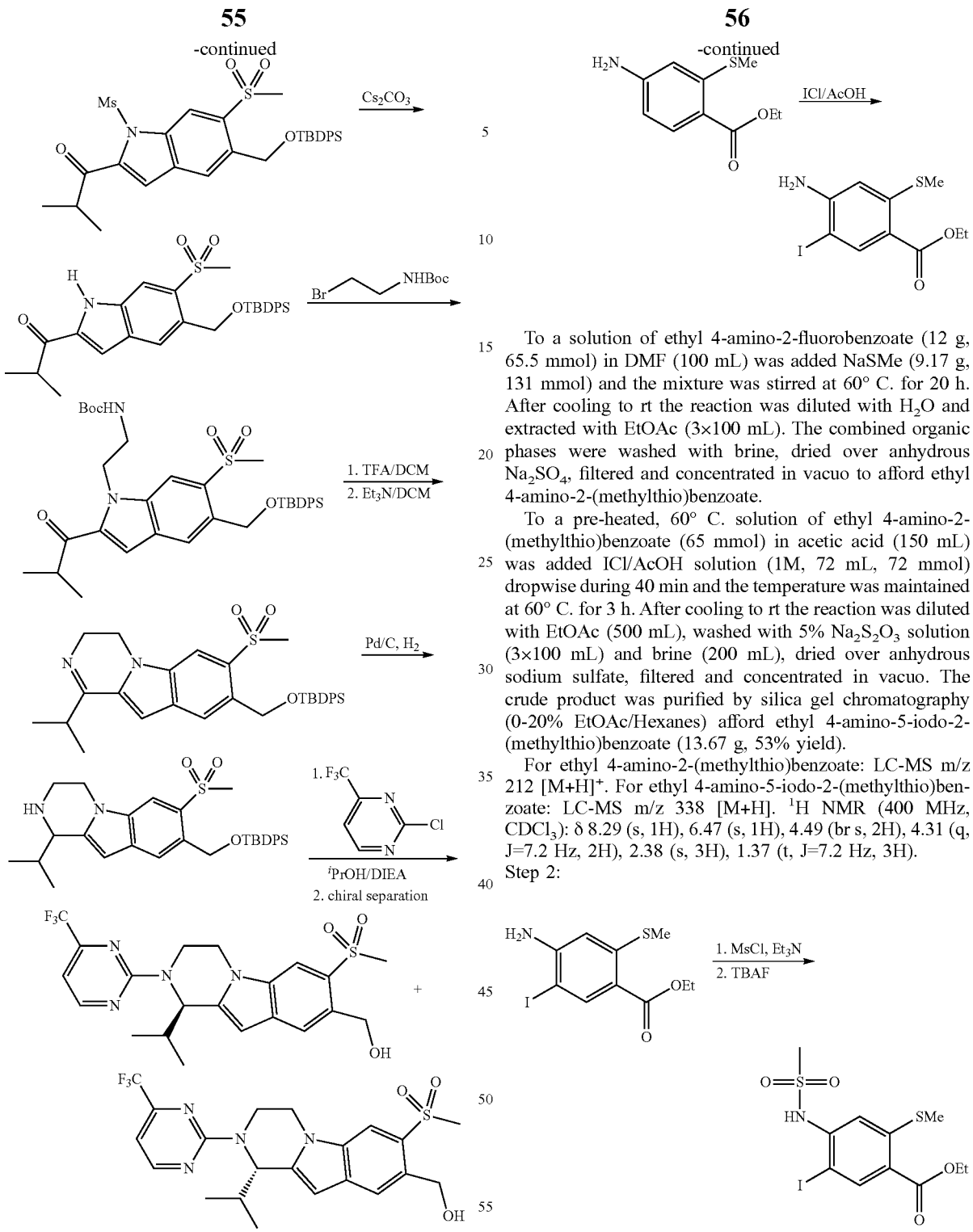

To a solution of ethyl 4-amino-2-fluorobenzoate (12 g, 65.5 mmol) in DMF (100 mL) was added NaSMe (9.17 g, 131 mmol) and the mixture was stirred at 60° C. for 20 h. After cooling to rt the reaction was diluted with H$_2$O and extracted with EtOAc (3×100 mL). The combined organic phases were washed with brine, dried over anhydrous Na$_2$SO$_4$, filtered and concentrated in vacuo to afford ethyl 4-amino-2-(methylthio)benzoate.

To a pre-heated, 60° C. solution of ethyl 4-amino-2-(methylthio)benzoate (65 mmol) in acetic acid (150 mL) was added ICl/AcOH solution (1M, 72 mL, 72 mmol) dropwise during 40 min and the temperature was maintained at 60° C. for 3 h. After cooling to rt the reaction was diluted with EtOAc (500 mL), washed with 5% Na$_2$S$_2$O$_3$ solution (3×100 mL) and brine (200 mL), dried over anhydrous sodium sulfate, filtered and concentrated in vacuo. The crude product was purified by silica gel chromatography (0-20% EtOAc/Hexanes) afford ethyl 4-amino-5-iodo-2-(methylthio)benzoate (13.67 g, 53% yield).

For ethyl 4-amino-2-(methylthio)benzoate: LC-MS m/z 212 [M+H]$^+$. For ethyl 4-amino-5-iodo-2-(methylthio)benzoate: LC-MS m/z 338 [M+H]. $^1$H NMR (400 MHz, CDCl$_3$): δ 8.29 (s, 1H), 6.47 (s, 1H), 4.49 (br s, 2H), 4.31 (q, J=7.2 Hz, 2H), 2.38 (s, 3H), 1.37 (t, J=7.2 Hz, 3H).

Step 2:

To a solution of ethyl 4-amino-5-iodo-2-(methylthio)benzoate (13.6 g, 40 mmol) in DCM (100 mL) was added Et$_3$N (13.8 mL, 100 mmol), followed by MsCl (7.7 mL, 100 mmol) at 0° C. After addition the mixture was stirred at rt for 2 h. 1N HCl solution (50 mL) was added to the mixture and the aqueous phase was extracted with DCM (1×100 mL). The organic solution was washed with brine, dried over anhydrous Na$_2$SO$_4$, filtered and concentrated in vacuo to give ethyl 5-iodo-4-(N-(methylsulfonyl)methylsulfonamido)-2-(methylthio)benzoate.

The crude reaction mixture above was dissolved into 100 mL THF. To this solution was added TBAF solution in THF (1 M, 100 mL) and the mixture was stirred at rt for 2 h. H₂O was added to the mixture and the aqueous phase was extracted with EtOAc (3×100 mL). The combined organic solution was washed with brine, dried over anhydrous Na₂SO₄, filtered and concentrated in vacuo to afford ethyl 5-iodo-4-(methylsulfonamido)-2-(methylthio)benzoate. It was used for next step without further purification. For ethyl 5-iodo-4-(N-(methylsulfonyl)methylsulfonamido)-2-(methylthio)benzoate: LC-MS m/z 494 [M+H]⁺. For ethyl 5-iodo-4-(methylsulfonamido)-2-(methylthio)benzoate: LC-MS m/z 415 [M+H]⁺.

Step 3:

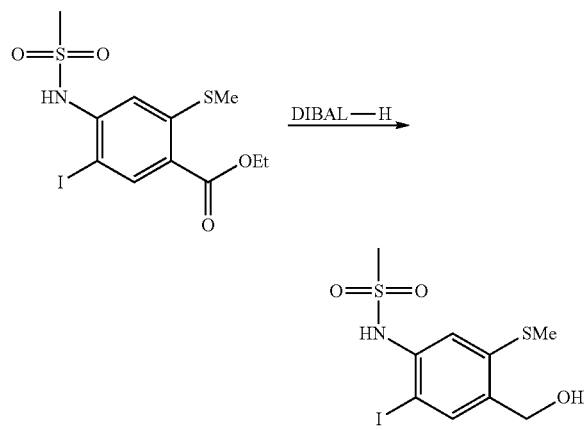

To a solution of ethyl 5-iodo-4-(methylsulfonamido)-2-(methylthio)benzoate (crude, from step 2) in dry toluene (200 mL) at 0° C. was added diisobutylaluminium hydride (1.0 M in toluene, 100 mL, 100 mmol) slowly. After addition, the mixture was stirred at 0° C. for 3 h and quenched with methanol/H₂O (1/1). The reaction mixture was poured into a vigorously stirred solution of potassium sodium tartrate (1M, 300 mL) and stirred vigorously for 2 h, after which time it settled to two clear phases. The organic layer was separated, and the aq layer was extracted with EtOAc (3×200 mL). The combined organic solution was washed with brine, dried over anhydrous sodium sulfate, filtered and concentrated in vacuo. The crude product was purified by silica gel chromatography (0-40% EtOAc/Hexanes) afford N-(4-(hydroxymethyl)-2-iodo-5-(methylthio)phenyl)methanesulfonamide (11.9 g, 80% yield for two steps). LC-MS m/z 356 [M+H]⁺. ¹H NMR (400 MHz, CDCl₃): δ 7.82 (s, 1H), 7.49 (s, 1H), 4.67 (s, 2H), 2.99 (s, 3H), 2.50 (s, 3H).

Step 4:

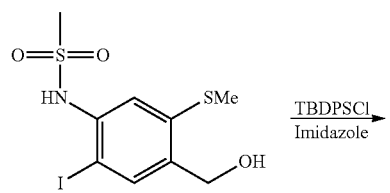

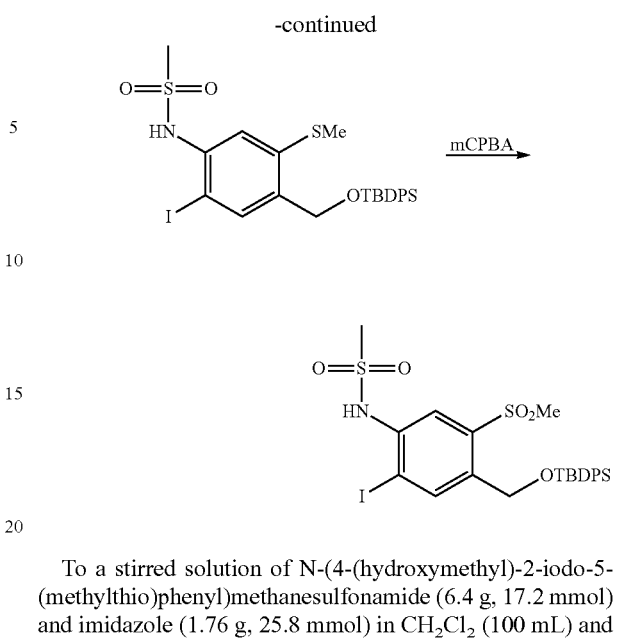

To a stirred solution of N-(4-(hydroxymethyl)-2-iodo-5-(methylthio)phenyl)methanesulfonamide (6.4 g, 17.2 mmol) and imidazole (1.76 g, 25.8 mmol) in CH₂Cl₂ (100 mL) and DMF (50 mL) at 0° C. was added tert-butyldiphenylsilyl chloride (5.8 mL, 22.4 mmol). The mixture was allowed to stir at rt overnight. The mixture was diluted with CH₂Cl₂ (100 mL), washed with 1N HCl solution, sat. aq. NaHCO₃ and brine, dried over anhydrous Na₂SO₄, filtered and concentrated in vacuo to afford N-(4-(((tert-butyldiphenylsilyl)oxy)methyl)-2-iodo-5-(methylthio)phenyl)methanesulfonamide. It was used for next step without further purification.

A suspension of crude N-(4-(((tert-butyldiphenylsilyl)oxy)methyl)-2-iodo-5-(methylthio)phenyl)methanesulfonamide and mCPBA (8.9 g, 51.6 mmol) in CH₂Cl₂ (100 mL) was stirred for 2 h at rt. Sat. aq. NaHCO₃ (50 mL) and Na₂S₂O₃ (50 mL) were added and the layers separated. The aqueous layer was extracted with CH₂Cl₂ (2×100 mL). The combined organic layers were dried over anhydrous Na₂SO₄, filtered and concentrated under reduced pressure. The residue was purified by flash chromatography over silica gel eluting with EtOAc/hexanes (3/7) to provide N-(4-(((tert-butyldiphenylsilyl)oxy)methyl)-2-iodo-5-(methylsulfonyl)phenyl)methanesulfonamide (8.8 g, 80% yield for two steps). For N-(4-(((tert-butyldiphenylsilyl)oxy)methyl)-2-iodo-5-(methylthio)phenyl)methanesulfonamide: LC-MS m/z 612 [M+H]⁺. For N-(4-(((tert-butyldiphenylsilyl)oxy)methyl)-2-iodo-5-(methylsulfonyl)phenyl)methanesulfonamide: LC-MS m/z 644 [M+H]⁺. ¹H NMR (400 MHz, CDCl₃): δ 8.25 (s, 1H), 8.08 (s, 1H), 7.67-7.65 (m, 4H), 7.46-7.37 (m, 6H), 6.77 (s, 1H), 5.05 (s, 2H), 3.11 (s, 3H), 2.83 (s, 3H), 1.12 (s, 9H).

Step 5:

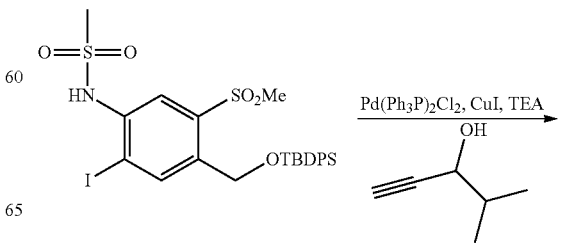

-continued

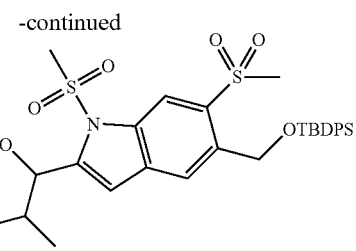

PdCl$_2$(PPh$_3$)$_2$ (277 mg, 0.38 mmol) and CuI (73 mg, 0.38 mmol) were added to a solution of N-(4-(((tert-butyldiphenylsilyl)oxy)methyl)-2-iodo-5-(methylsulfonyl)phenyl)methanesulfonamide (2.45 g, 3.8 mmol) in THF (20 mL) and Et$_3$N (10 mL). The mixture was purged with nitrogen for 10 min followed by addition of 4-methylpent-1-yn-3-ol (745 mg, 7.6 mmol) and stirred at 65° C. for 8 h. The reaction mixture was diluted with EtOAc (50 mL) and washed with 1N HCl (50 mL). The organic layer was separated, and the aq layer was extracted with EtOAc (3×50 mL). The combined organic solution was washed with brine, dried over anhydrous sodium sulfate, filtered and concentrated under reduced pressure. The residue was purified by flash chromatography over silica gel eluting with EtOAc/hexanes (3/7) to provide 1-(5-(((tert-butyldiphenylsilyl)oxy)methyl)-1,6-bis(methylsulfonyl)-1H-indol-2-yl)-2-methylpropan-1-ol (2.1 g, 90% yield). LC-MS m/z 614 [M+H]$^+$. $^1$H NMR (400 MHz, CDCl$_3$): δ 8.68 (s, 1H), 7.90 (s, 1H), 7.71-7.67 (s, 4H), 7.46-7.35 (m, 6H), 6.77 (s, 1H), 5.21 (d, J=3.2 Hz, 2H), 6.94 (t, J=6.8 Hz, 1H), 3.22 (s, 3H), 2.90 (s, 3H), 2.61 (d, J=6.8 Hz, 1H), 2.37-2.32 (m, 1H), 1.12 (s, 9H), 1.05 (d, J=6.8 Hz, 3H), 1.03 (d, J=6.8 Hz, 3H). $^{13}$C NMR (100 MHz, CDCl$_3$): δ 147.25, 135.54, 135.28, 135.00, 133.66, 133.00, 132.89, 129.96, 127.85, 121.68, 115.96, 108.69, 72.30, 62.98, 44.33, 41.59, 32.88, 26.89, 20.23, 19.30, 17.61.

Step 6:

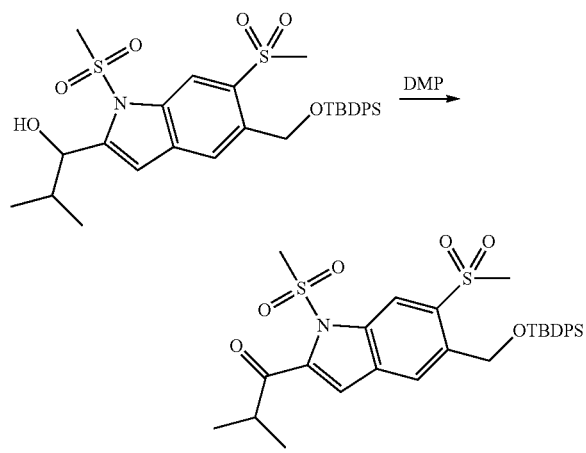

To a stirred solution of 1-(5-(((tert-butyldiphenylsilyeoxy)methyl)-1,6-bis(methylsulfonyl)-1H-indol-2-yl)-2-methylpropan-1-ol (2.3 g, 3.8 mmol) in dry CH$_2$Cl$_2$ (25 mL) was added Dess-Martin periodinane (1.94 g, 4.56 mmol) in one portion. The mixture was allowed to stir at rt for 2 h. The reaction was quenched with a solution of Na$_2$S$_2$O$_3$ (5 g in 30 mL H$_2$O) and sat. aq. NaHCO$_3$ (40 mL). The mixture was extracted with EtOAc (3 ×80 mL). The combined organic solution was washed with brine, dried over anhydrous Na$_2$SO$_4$, filtered and concentrated under reduced pressure.

The residue was purified by flash chromatography over silica gel eluting with EtOAc/hexanes (2/8) to provide 1-(5-(((tert-butyldiphenylsilyl)oxy)methyl)-1,6-bis(methylsulfonyl)-1H-indol-2-yl)-2-methylpropan-1-one (2.0 g, 86% yield). LC-MS m/z 612 [M+H]$^+$. $^1$H NMR (400 MHz, CDCl$_3$): δ 8.69 (s, 1H), 8.03 (s, 1H), 7.70-7.68 (m, 4H), 7.46-7.36 (m, 6H), 7.22 (s, 1H), 5.20 (s, 2H), 3.80 (s, 3H), 3.36 (m, 1H), 2.89 (s, 3H), 1.29 (d, J=6.8 Hz, 6H), 1.13 (s, 9H). $^{13}$C NMR (100 MHz, CDCl$_3$): 67 197.83, 141.53, 136.69, 136.05, 135.50, 135.04, 132.81, 131.14, 129.99, 127.88, 123.17, 117.12, 114.21, 62.87, 44.19, 44.03, 39.09, 26.88, 19.30, 18.41.

Step 7:

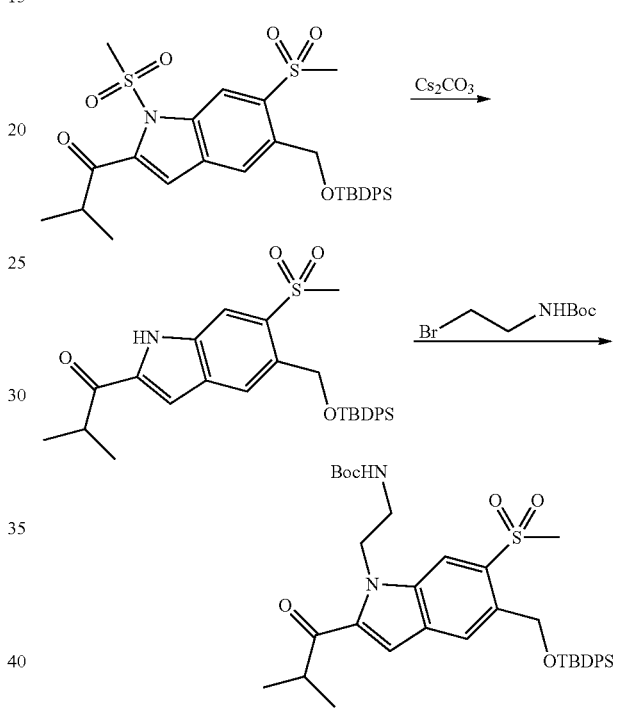

To a stirred solution of 1-(5-(((tert-butyldiphenylsilyl)oxy)methyl)-1,6-bis(methylsulfonyl)-1H-indol-2-yl)-2-methylpropan-1-one (780 mg, 1.27 mmol) in THF/methanol (15 mL/15 mL) was added Cs$_2$CO$_3$ (1.25 g, 3.83 mmol) in one portion. The mixture was allowed to stir at rt for 4 h and concentrated in vacuo to afford the crude product 1-(5-(((tert-butyldiphenylsilyl)oxy)methyl)-6-(methylsulfonyl)-1H-indol-2-yl)-2-methylpropan-1-one. It was used for the next step reaction without further purification. To a solution of crude 1-(5-(((tert-butyldiphenylsilyl)oxy)methyl)-6-(methylsulfonyl)-1H-indol-2-yl)-2-methylpropan-1-one, 2-(Boc-amino)ethyl bromide (2.8 g, 12 mmol), tetrabutylammonium iodide (235 mg, 0.63 mmol) in CH$_2$Cl$_2$/toluene (2 mL/4 mL) was added 40% NaOH aqueous solution (20 mL). The mixture was allowed to stir at rt for 20 h. The reaction mixture was diluted with CH$_2$Cl$_2$ (40 mL) and washed with H$_2$O (50 mL). The organic layer was separated, and the aqueous layer was extracted with CH$_2$Cl$_2$ (4×50 mL). The combined organic solution was washed with brine, dried over anhydrous sodium sulfate, filtered and concentrated under reduced pressure. The residue was purified by flash chromatography over silica gel eluting with CH$_2$Cl$_2$/Methanol (95/5) to provide tert-butyl (2-(5-(((tert-butyldiphenylsilyl)oxy)methyl)-2-isobutyryl-6-(methylsulfonyl)-1H-indol-1-yl)ethyl)carbamate (300 mg, 35% yield for two steps).

For 1-(5-(((tert-butyldiphenylsilyl)oxy)methyl)-6-(methylsulfonyl)-1H-indol-2-yl)-2-methylpropan-1-one: LC-MS m/z 556 [M+Na]+.

For tert-butyl (2-(5-(((tert-butyldiphenylsilyl)oxy)methyl)-2-isobutyryl-6-(methylsulfonyl)-1H-indol-1-yl)ethyl)carbamate: LC-MS m/z 699 [M+Na]+. $^1$H NMR (400 MHz, CDCl$_3$): δ 8.20 (s, 1H), 7.93 (s, 1H), 7.72 (dd, J$_1$=8.0 Hz, J$_2$=1.6 Hz, 4H), 7.47-7.35 (m, 7H), 5.21 (s, 2H), 4.72 (d, J=6.8 Hz, 2H), 3.55 (d, J=6.8 Hz, 2H), 3.33-3.26 (m, 1H), 3.00 (s, 3H), 1.46 (s, 9H), 1.30 (d, J=6.4 Hz, 3H), 1.28 (d, J=6.4 Hz, 3H), 1.11 (s, 9H).

Step 8:

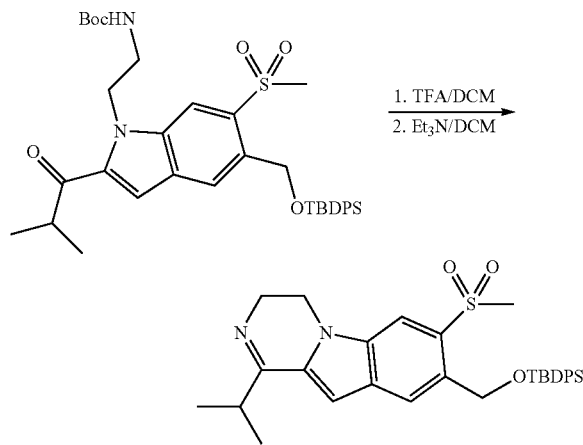

To a solution of tert-butyl (2-(5-(((tert-butyldiphenylsilyl)oxy)methyl)-2-isobutyryl-6-(methylsulfonyl)-1H-indol-1-yl)ethyl)carbamate (250 mg, 0.37 mmol) in CH$_2$Cl$_2$ (5.0 mL) was added trifluoroacetic acid (1.0 mL) and the mixture was allowed to stir at rt for 1 h. The excess amount of TFA was removed by azeotropic evaporation with toluene under reduced pressure. The residue was redissolved in CH$_2$Cl$_2$ (5 mL) and Et$_3$N (0.5 mL) was added. The reaction mixture was stirred at rt for 45 min and concentrated in vacuo. The residue was purified by flash chromatography over silica gel eluting with CH$_2$Cl$_2$/methanol (98/2) to provide 8-(((tert-butyldiphenylsilyl)oxy)methyl)-1-isopropyl-7-(methylsulfonyl)-3,4-dihydropyrazino[1,2-a]indole (135 mg, 65% yield). LC-MS m/z 559 [M+H]+.

Step 9:

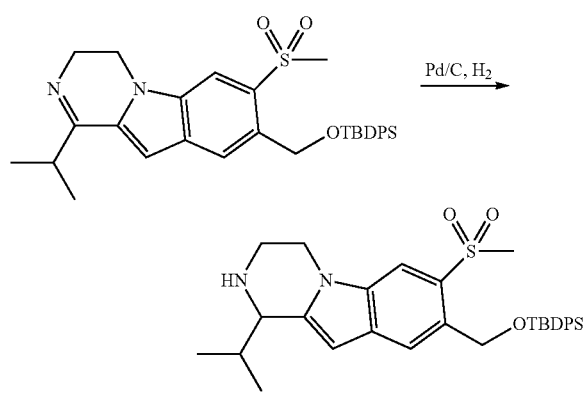

A solution of 8-(((tert-butyldiphenylsilyl)oxy)methyl)-1-isopropyl-7-(methylsulfonyl)-3,4-dihydropyrazino[1,2-a]indole (140 mg, 0.25 mmol), 10% palladium on charcoal (37 mg, 0.025 mmol), and methanol (5 mL) was stirred at rt under 1 atmosphere of hydrogen for 3 h. The mixture was filtered through Celite® and the Celite® was washed thoroughly with methanol. Combined solvent was removed under reduced pressure to afford 8-(((tert-butyldiphenylsilyl)oxy)methyl)-1-isopropyl-7-(methylsulfonyl)-1,2,3,4-tetrahydropyrazino[1,2-a]indole. It was used directly without further purification. A small portion of product was purified by chromatography for characterization. LC-MS m/z 561 [M+H]+. $^1$H NMR (400 MHz, CD$_3$OD): δ 8.00 (s, 1H), 7.73-7.70 (m, 5H), 7.47-7.40 (m, 6H), 6.36 (s, 1H), 5.20 (d, J=2.0 Hz, 2H), 4.24-4.19 (m, 1H), 4.11-4.00 (m, 2H), 3.52-3.47 (m, 1H), 3.20-3.13 (m, 1H), 3.03 (s, 3H), 2.47-2.39 (m, 1H), 1.18 (d, J=6.8 Hz, 3H), 1.09 (s, 9H), 0.96 (d, J=6.8 Hz, 3H). $^{13}$C NMR (100 MHz, CDCl$_3$): δ 143.06, 135.68, 134.04, 133.31, 131.52, 130.26, 129.79, 129.51, 127.77, 121.39, 111.22, 97.14, 63.76, 59.28, 45.00, 42.94, 42.47, 31.55, 26.94, 19.72, 19.31, 16.49.

Step 10:

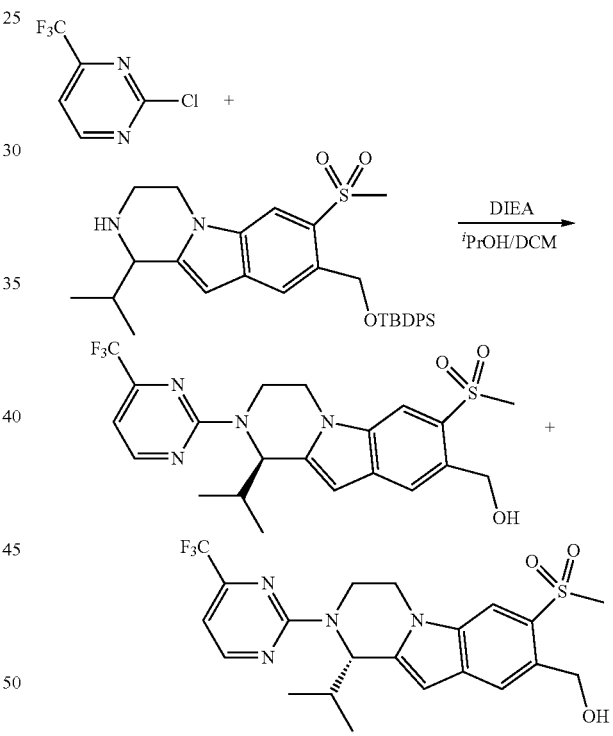

A mixture of 2-chloro-4-(trifluoromethyl)pyrimidine (80 mg, 0.44 mmol), 8-(((tert-butyldiphenylsilyl)oxy)methyl)-1-isopropyl-7-(methylsulfonyl)-1,2,3,4-tetrahydropyrazino[1,2-a]indole (crude, from step 9), and DIEA (115 µL, 0.66 mmol) in i-PrOH/CH$_2$Cl$_2$ (2 mL/1 mL) was stirred at 110° C. for 30 h. The solvent was removed under reduced pressure and the crude residue was purified by silica chromatography and SFC separation on a chiral column to give isomers of (1-isopropyl-7-(methylsulfonyl)-2-(4-(trifluoromethyl)pyrimidin-2-yl)-1,2,3,4-tetrahydropyrazino[1,2-a]indol-8-yl)methanol (75 mg, 72% yield for two steps).

Isomer 1: Analytical chiral HPLC: t$_R$=11.8 min in 15 min chromatography (Method: AD-H_5_5_40_2.35 ML). LC-MS m/z 469 [M+H]+. $^1$H NMR (400 MHz, CD$_3$OD): δ 8.65

(d, J=4.8 Hz, 1H), 8.10 (s, 1H), 7.78 (s, 1H), 6.95 (d, J=4.8 Hz, 1H), 6.52 (s, 1H), 5.91-5.89 (m, 1H), 5.14-5.09 (m, 1H), 5.06 (s, 2H), 4.47-4.42 (m, 1H), 4.12-4.05 (m, 1H), 3.94-3.86 (m, 1H), 3.26 (s, 3H), 2.37-2.29 (m, 1H), 1.17 (d, J=6.8 Hz, 3H), 1.03 (d, J=6.8 Hz, 3H).

Isomer 2: Analytical chiral HPLC: $t_R$=9.7 min in 15 min chromatography (Method: AD-H_5_5_40_2.35 ML). LC-MS m/z 469 [M+H]$^+$. $^1$H NMR (400 MHz, CD$_3$OD): δ 8.65 (d, J=4.8 Hz, 1H), 8.10 (s, 1H), 7.78 (s, 1H), 6.95 (d, J=4.8 Hz, 1H), 6.52 (s, 1H), 5.91-5.89 (m, 1H), 5.14-5.09 (m, 1H), 5.06 (s, 2H), 4.47-4.42 (m, 1H), 4.12-4.05 (m, 1H), 3.94-3.86 (m, 1H), 3.26 (s, 3H), 2.37-2.29 (m, 1H), 1.17 (d, J=6.8 Hz, 3H), 1.03 (d, J=6.8 Hz, 3H).

Example 5

LXR α/β Radioligand Binding Assay

Compounds of the invention were assessed in a competition binding assay where different concentrations of compounds were incubated with the LXR ligand binding domain (LBD) in the presence of radiolabeled LXR ligand [$^3$H] T0901317. The amount of the LXR-LBD that complexed with [$^3$H]T0901317 was measured by scintillation proximity assay (SPA) employing non-specific binding of LXR-LBD to poly-lysine coated Yttrium silicate beads. Partially purified LXR α or β LBD protein (15-45 nM) was incubated at rt for 30 min with 15 nM [$^3$H]T0901317 (25-40 Ci/mmol) and different concentrations of test compounds in 80 μL of phosphate buffered saline (PBS) buffer containing 2.5% DMSO, 1% glycerol, 2 mM EDTA, 2 mM CHAPS and 5 mM DTT in 96-well plates. Poly-lysine SPA beads (50 μg) were added to each well and the total volume was adjusted to 120 μL. The plates were shaken on an orbital shaker for 20 min and then allowed to settle for 10 more minutes at rt before a brief centrifugation at 2,000 rpm for 1 min. The SPA signal was measured on a MicroBeta® liquid scintillation counter (Perkin Elmer, Waltham, MA), and the results were used for calculating IC50 values based on the total binding (DMSO control) and non-specific binding (5 μM of unlabeled T0901317) controls. The $K_i$ values were calculated according to equation 1, where [RL] is the final concentration of [$^3$H]T0901317 in the assay, and the $K_d$ values of 20 nM and 10 nM of T0901317 for LBDs of LXRα and LXRβ, respectively, were determined by direct titration of the radioligand with these proteins.

$$Ki = \frac{IC50}{\left(1 + \frac{[RL]}{Kd}\right)} (1)$$

Example 6

LXR Luciferase Transcriptional Reporter Gene Assay

The LXR luciferase transcriptional reporter gene assay measures the ability of LXR ligands to promote transcriptional activation via the ligand binding domain (LBD) of LXR. HEK293 cells were grown in DMEM medium containing 10% FBS (Gibco®, #11995-065) and 1×PenStrep (Gibco®, #15140) at 37° C. in 5% CO$_2$ atmosphere. 90% confluent cells from a 150 mm dish were seeded in six 100 mm dishes. The cells were batch-transfected with an expression plasmid containing the Gal4 DNA binding domain fused to either the LBD of LXRα or LXRβ and a luciferase reporter plasmid pG5-Luc (Promega, Madison, WI), which has Gal4 response elements upstream of firefly luciferase gene (luc+). Transfection was accomplished with Lipofectamine™2000 (Gibco®) according to the manufacturer's suggested protocol. Five h following transfection, 15 mL of 10% charcoal-treated FBS (Hyclone, #SH30070.03) in DMEM were added to the transfected dishes without removing transfection media, and then incubate the cells at 37° C. overnight. The next day, the cells from the transfected dish were trypsinized, washed with PBS, resuspended in 10% charcoal-treated DMEM media and plated into 96-well plates with 60,000 cells/100 μL per well. The cells were incubated at 37° C. for ~4 h before addition of 100 μL of test compound or control ligand at different concentrations (final DMSO concentration at 0.2%). Following incubation of the cells for 16 h with substances, the culture media were dumped and Bright-Glo™ luciferase reagent (Promega, Cat. #E2610) was added to lyse the cells and initiate the luciferase reaction. Luminescence, as a measure of luciferase activity, was detected in a plate reader (Victor2, PE-Wallac). Transcriptional activation in the presence of a test substance was expressed as fold-change in luminescence compared to that of cells incubated in the absence of the substance. EC$_{50}$ values were calculated using the XLfit™ program (IDBS, Guildford, UK).

Example 7

Compounds of the invention were tested as described in Examples 5 and 6. The biological data are presented in the table below.

| Compound No. | Example No. | LXRα BINDING $K_i$ (nM) | LXRβ BINDING $K_i$ (nM) | LXRα CELL EC50 (nM) | LXRβ CELL EC50 (nM) |
|---|---|---|---|---|---|
| E1 | Example 1 | 1770 | 256 | 3370 | 313 |
| E2a | Example 2, isomer 1 | 318 | 20 | 340 | 13 |
| E2b | Example 2, isomer 2 | >3330 | >2500 | 17300 | 6940 |
| E3a | Example 3, isomer 1 | 398 | 27 | 1100 | 87 |
| E3b | Example 3, isomer 2 | >3330 | 1750 | >20000 | >20000 |
| E4a | Example 4, isomer 1 | 43 | 4 | 163 | 10 |
| E4b | Example 4, isomer 2 | >3330 | 846 | >20000 | >20000 |

What is claimed is:

1. A method of treating a subject with disease or disorder selected from common acne, comedones, polymorphs, rosacea, nodulocystic acne, acne conglobate, senile acne, secondary acne, solar acne, medicinal acne, occupational acne, ichthyosis, ichthyosiform conditions, Darier's disease, palmoplantar keratoderma, leukoplakia, leukoplakiform conditions, cutaneous or mucous lichen, cutaneous psoriasis, mucous psoriasis, ungual psoriasis, psoriatic rheumatism, cutaneous atopy, respiratory atopy, gingival hypertrophy, common warts, flat warts, epidermodysplasia verruciformis, oral or florid papillomatoses, T lymphoma, cutaneous T-cell lymphoma, basocellular epithelioma, spinocellular epithelioma, precancerous skin lesions, keratoacanthomas, immune bullous immune diseases, collagen diseases, scleroderma, keratosis, sebaceous function disorders, cicatrization disorders, stretch marks, pigmentation disorders, hyperpigmentation, melasma, hypopigmentation, vitiligo, and alopecia, comprising administering to the subject an effective amount of a compound represented by the following structural formula:

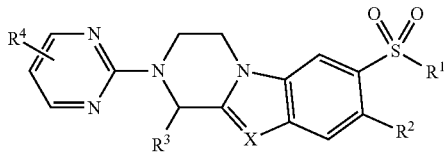

or a pharmaceutically acceptable salt thereof, wherein:
X is N or CR$^c$;
R$^1$ is alkyl or —NR$^a$R$^b$;
R$^2$ is H; halogen; —CN; —NRC(O)R; —C(O)OR; —C(O)NR$^a$R$^b$; monocyclic heteroaromatic optionally substituted with one or more groups selected from alkyl, —CN, —NRC(O)R, —C(O)OR, —C(O)NR$^a$R$^b$ and halogen; monocyclic non—aromatic heterocycle optionally substituted with one or more groups selected from alkyl, halogen, —CN and =O; or alkyl optionally substituted by one or more groups selected from halogen, hydroxy, alkoxy, —NR$^a$R$^b$, —NRC(O)R, —NRC(O)O(alkyl), —NRC(O)N(R)$_2$, —C(O)OR, thiol, alkylthiol, nitro, —CN, =O, —OC(O)H, —OC(O)(alkyl), —OC(O)O(alkyl), —OC(O)N(R)$_2$ and —C(O)NR$^a$R$^b$;
R$^3$ is alkyl, haloalkyl, hydroxyalkyl, alkoxyalkyl, cycloalkyl, monocyclic non-aromatic heterocycle, monocyclic heteroaromatic or phenyl, wherein the phenyl, monocyclic non-aromatic heterocycle, and monocyclic heteroaromatic group represented by R$^3$ are optionally substituted with one or more groups selected from alkyl, halogen, haloalkyl, alkoxy, haloalkoxy, nitro and —CN;
R$^4$ is halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl, monocyclic non—aromatic heterocycle, monocyclic heteroaromatic or alkyl, wherein the monocyclic non—aromatic heterocycle, monocyclic heteroaromatic and alkyl group represented by R$^4$ are optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$;
Each R independently is H or alkyl;
R$^a$ and R$^b$ are independently H, alkyl or R$^a$ and R$^b$ can be taken together with the nitrogen to which they are attached to form a monocyclic non-aromatic heterocycle; and
R$^c$ is H, alkyl, or halogen.
2. The method of claim 1, wherein:
R$^3$ is alkyl, haloalkyl, hydroxyalkyl, alkoxyalkyl, cycloalkyl or phenyl, wherein the phenyl represented by R$^3$ is optionally substituted with one or more groups selected from alkyl, halogen, haloalkyl, alkoxy, haloalkoxy, nitro and —CN;

R$^4$ is halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl or alkyl, wherein the alkyl group represented by R$^4$ is optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$.

3. The method of claim 1, wherein the compound is represented by the following structural formula:

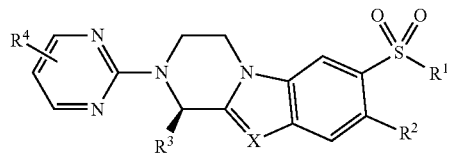

or a pharmaceutically acceptable salt thereof.

4. The method of claim 1, wherein the compound is represented by the following structural formula:

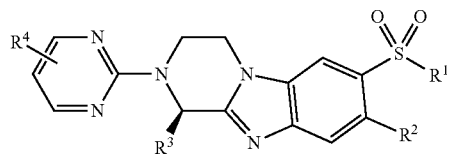

or a pharmaceutically acceptable salt thereof.

5. The method of claim 4, wherein the compound is represented by the following structural formula:

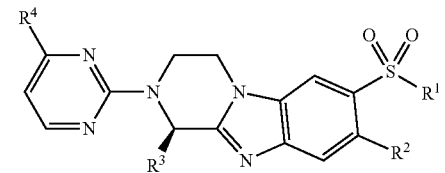

or a pharmaceutically acceptable salt thereof.

6. The method of claim 1, wherein the compound is represented by the following structural formula:

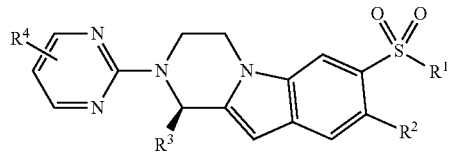

or a pharmaceutically acceptable salt thereof.

7. The method of claim 6, wherein the compound is represented by the following structural formula:

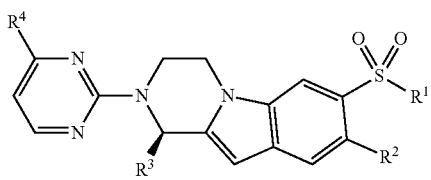

or a pharmaceutically acceptable salt thereof.

8. The method of claim 7, wherein:

$R^1$ is methyl or —$NH_2$;

$R^2$ is H or methyl, wherein the methyl group represented by $R^2$ is optionally substituted with one or more groups selected from halogen, hydroxy, alkoxy, —$NR^aR^b$, —NRC(O)R, —NRC(O)O(alkyl), —NRC(O)N(R)$_2$, —C(O)OR, thiol, alkylthiol, nitro, —CN, =O, —OC(O)H, —OC(O)(alkyl), —OC(O)O(alkyl), —C(O)NR$^a$R$^b$ and —OC(O)N(R)$_2$;

$R^3$ is methyl, ethyl, propyl, isopropyl, tent-butyl, sec-butyl, iso-butyl, —$CH_2CF_3$, —$CH(CH_2F)_2$, —CH$(CHF_2)_2$, —$CH(CF_3)_2$, —$CF(CH_3)_2$, —$CF_3$, cyclopropyl, cyclobutyl, cyclopentyl cyclohexyl, —C(OH)$(CH_3)_2$, —CH(OH)($CH_3$), or phenyl, wherein the phenyl group represented by $R^3$ is optionally substituted with one or more groups selected from alkyl, halogen, haloalkyl, alkoxy, haloalkoxy, nitro and —CN; and $R^c$, where present, is H.

9. The method of claim 8, wherein $R^2$ is H or —$CH_2OH$.

10. The method of claim 9, wherein $R^4$ is halogen, hydroxy, alkyl, cycloalkyl, cycloalkoxy, alkoxy, haloalkoxy, haloalkyl, —N(R)$_2$, —C(O)OH, —C(O)O(alkyl), —C(O)O(haloalkyl), —C(O)(alkyl), —C(O)N(R)$_2$, —NRC(O)R, —SO$_2$N(R)$_2$, —OC(O)N(R)$_2$, —CN, hydroxyalkyl or dihydroxyalkyl.

11. The method of claim 10, wherein $R^4$ is methyl, ethyl, hydroxy, $CF_3$, isopropyl, cyclopropyl, $CH_2OH$, —CH(OH)($CH_2$)(OH), —C(OH)($CH_3$)$_2$, —CH(OH)($CH_3$), —CH(OH)($CH_2$)($CH_3$), —CH(OH)($CH_2$)$_2$($CH_3$), —C(O)$NH_2$, C(O)N$(CH_3)_2$, —C(O)OH, —C(O)NH($CH_3$), C(O)$CH_3$, C(O)$CH_2CH_3$, C(O)O($CH_2$)($CH_3$), —C(O)O (tert-butyl), —C(O)O(C)($CH_3$)$_2$($CF_3$), —NHC(O)$CH_3$, —$OCHF_2$, —$OCF_3$, —$OCH_2CH_3$, —$OCH(CH_3)_2$ or —$OCH_3$.

12. The method of claim 11, wherein $R^4$ is alkyl, haloalkyl, cycloalkyl, alkoxy, or haloalkoxy.

13. The method of claim 12, wherein $R^4$ is methyl, halogenated methyl, cyclopropyl, —$OCHF_2$ or —$OCH_3$.

14. The method of claim 1, wherein the compound is represented by a structural formula selected from:

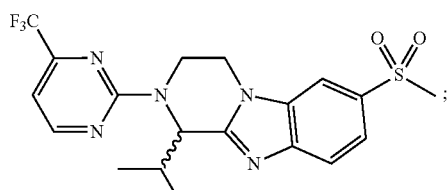

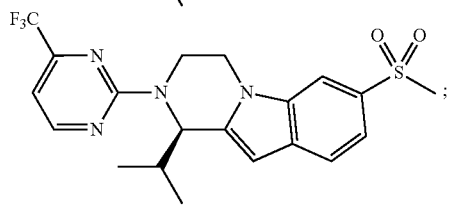

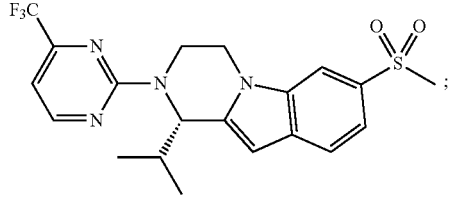

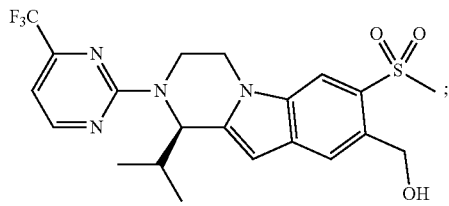

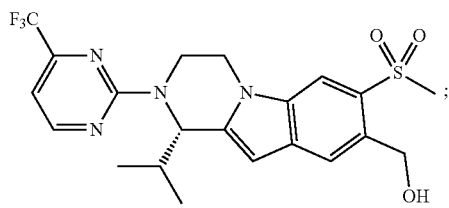

or a pharmaceutically acceptable salt of any of the foregoing.

15. A method of treating a subject with disease or disorder selected from common acne, comedones, polymorphs, rosacea, nodulocystic acne, acne conglobate, senile acne, secondary acne, solar acne, medicinal acne, occupational acne, ichthyosis, ichthyosiform conditions, Darier's disease, palmoplantar keratoderma, leukoplakia, leukoplakiform conditions, cutaneous or mucous lichen, cutaneous psoriasis, mucous psoriasis, ungual psoriasis, psoriatic rheumatism, cutaneous atopy, respiratory atopy, gingival hypertrophy, common warts, flat warts, epidermodysplasia verruciformis, oral or florid papillomatoses, T lymphoma, cutaneous T-cell lymphoma, basocellular epithelioma, spinocellular epithelioma, precancerous skin lesions, keratoacanthomas, immune bullous immune diseases, collagen diseases, scleroderma, keratosis, sebaceous function disorders, cicatrization disorders, stretch marks, pigmentation disorders, hyperpigmentation, melasma, hypopigmentation, vitiligo, and alopecia, comprising administering to the subject an effective amount of a compound of the formula:

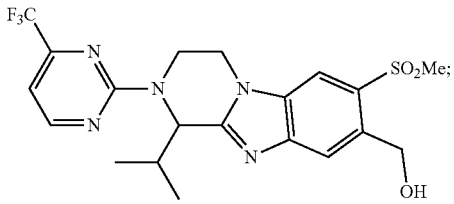 [SMILES: CC(C)C1c2nc3cc(CO)c(S(C)(=O)=O)cc3n2CCN1c1nccc(C(F)(F)F)n1]

or a pharmaceutically acceptable salt thereof.

16. The method of claim 15, wherein the compound is of the formula:

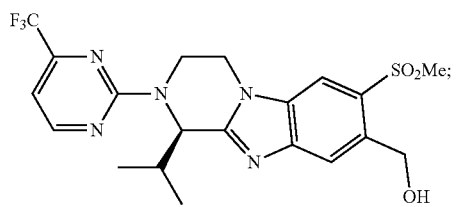 [SMILES: CC(C)[C@@H]1c2nc3cc(CO)c(S(C)(=O)=O)cc3n2CCN1c1nccc(C(F)(F)F)n1]
or a pharmaceutically acceptable salt thereof.
* * * * *

UNITED STATES PATENT AND TRADEMARK OFFICE
CERTIFICATE OF CORRECTION

PATENT NO. : 9,814,715 B2
APPLICATION NO. : 15/182749
DATED : November 14, 2017
INVENTOR(S) : Chengguo Dong et al.

Page 1 of 1

It is certified that error appears in the above-identified patent and that said Letters Patent is hereby corrected as shown below:

In the Claims

Column 67, Claim 8, Line 20, please replace "tent-butyl" with --tert-butyl--.

Signed and Sealed this
Fourteenth Day of May, 2019

Andrei Iancu
*Director of the United States Patent and Trademark Office*